US009899602B2

(12) United States Patent
Kawakami et al.

(10) Patent No.: US 9,899,602 B2
(45) Date of Patent: *Feb. 20, 2018

(54) SPIROFLUORENE DERIVATIVE, MATERIAL FOR LIGHT-EMITTING ELEMENT, LIGHT-EMITTING ELEMENT, LIGHT-EMITTING DEVICE, AND ELECTRONIC DEVICE

(71) Applicant: Semiconductor Energy Laboratory Co., Ltd., Atsugi-shi, Kanagawa-ken (JP)

(72) Inventors: Sachiko Kawakami, Isehara (JP); Harue Nakashima, Atsugi (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,331

(22) Filed: Jan. 12, 2017

(65) Prior Publication Data

US 2017/0125679 A1    May 4, 2017

Related U.S. Application Data

(60) Continuation of application No. 14/950,613, filed on Nov. 24, 2015, now Pat. No. 9,548,457, which is a
(Continued)

(30) Foreign Application Priority Data

Sep. 30, 2005 (JP) .................................. 2005-289418

(51) Int. Cl.
*H01L 51/50* (2006.01)
*H01L 51/00* (2006.01)
(Continued)

(52) U.S. Cl.
CPC .......... *H01L 51/006* (2013.01); *C07C 211/61* (2013.01); *H01L 27/3248* (2013.01);
(Continued)

(58) Field of Classification Search
CPC ............... H01L 51/006; H01L 27/3248; H01L 27/3262
See application file for complete search history.

(56) References Cited

U.S. PATENT DOCUMENTS

| 5,840,217 A | 11/1998 | Lupo et al. |
| 6,335,480 B1 | 1/2002 | Bach et al. |

(Continued)

FOREIGN PATENT DOCUMENTS

| JP | 11-273863 A | 10/1999 |
| JP | 2001-518913 | 10/2001 |

(Continued)

OTHER PUBLICATIONS

Vanslyke.S et al., "Organic Electroluminescent Devices With Improved Stability", Appl. Phys. Lett. (Applied Physics Letters), Oct. 7, 1996, vol. 69, No. 15, pp. 2160-2162.

(Continued)

*Primary Examiner* — Mark Tornow
(74) *Attorney, Agent, or Firm* — Robinson Intellectual Property Law Office; Eric J. Robinson

(57) ABSTRACT

It is an object of the present invention to provide a material having a high Tg and a wide energy gap. The present invention provides a spirofluorene derivative represented by General Formula 1. (In the formula, $R^1$ is any one of hydrogen, an alkyl group having 1 to 4 carbon atoms, or a group represented by General Formula 2. Each of $R^2$ and $R^3$ is either hydrogen or an alkyl group having 1 to 4 carbon atoms and may be identical or different. $R^4$ is an aryl group having 6 to 15 carbon atoms. Each of $R^5$ and $R^6$ is any one
(Continued)

of hydrogen, an alkyl group having 1 to 4 carbon atoms, or an aryl group having 6 to 15 carbon atoms and may be identical or different.)

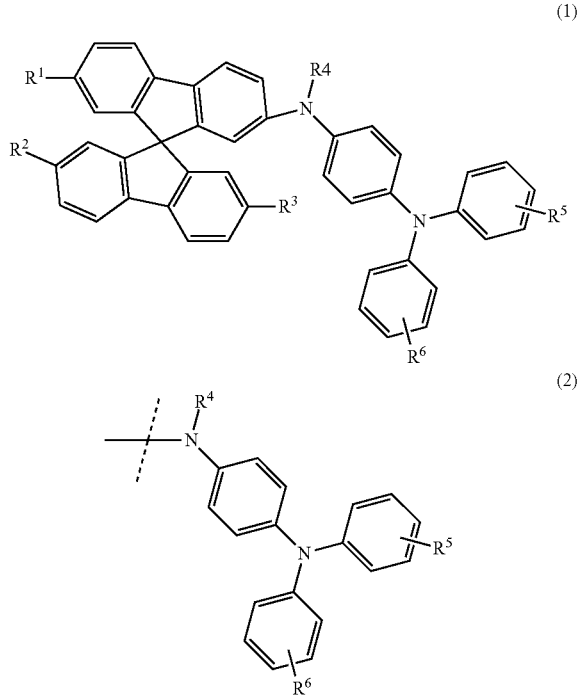

(1)

(2)

26 Claims, 51 Drawing Sheets

Related U.S. Application Data division of application No. 14/244,432, filed on Apr. 3, 2014, now Pat. No. 9,203,035, which is a division of application No. 13/035,256, filed on Feb. 25, 2011, now Pat. No. 8,704,212, which is a continuation of application No. 12/794,145, filed on Jun. 4, 2010, now Pat. No. 7,897,964, which is a division of application No. 11/526,874, filed on Sep. 26, 2006, now Pat. No. 7,816,668.

(51) Int. Cl.
  *H01L 51/52* (2006.01)
  *H01L 27/32* (2006.01)
  *H01L 29/49* (2006.01)
  *C07C 211/61* (2006.01)

(52) U.S. Cl.
  CPC ...... *H01L 27/3262* (2013.01); *H01L 29/4908* (2013.01); *H01L 51/0096* (2013.01); *H01L 51/5218* (2013.01); *H01L 51/5221* (2013.01); *C07C 2103/97* (2013.01); *H01L 51/0056* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 2251/301* (2013.01); *H01L 2251/308* (2013.01)

(56) References Cited

U.S. PATENT DOCUMENTS

| | | | |
|---|---|---|---|
| 6,664,071 | B1 | 12/2003 | Windhab et al. |
| 6,822,094 | B2 | 11/2004 | Salbeck et al. |
| 6,887,392 | B2 | 5/2005 | Ogino et al. |
| 7,208,869 | B2 | 4/2007 | Ogino et al. |
| 7,303,937 | B2 | 12/2007 | Chen et al. |
| 7,326,474 | B2 | 2/2008 | Kim |
| 7,510,781 | B2 | 3/2009 | Suzuki et al. |
| 7,540,978 | B2 | 6/2009 | Pfeiffer et al. |
| 7,547,562 | B2 | 6/2009 | Ogino |
| 7,550,173 | B2 | 6/2009 | Seo et al. |
| 7,816,668 | B2 | 10/2010 | Kawakami et al. |
| 7,897,964 | B2 | 3/2011 | Kawakami et al. |
| 8,704,212 | B2 * | 4/2014 | Kawakami ............ C07C 211/61 257/40 |
| 9,203,035 | B2 | 12/2015 | Kawakami et al. |
| 2002/0093283 | A1 | 7/2002 | Seo et al. |
| 2003/0227021 | A1 | 12/2003 | Yamazaki et al. |
| 2005/0189543 | A1 | 9/2005 | Yamazaki et al. |
| 2007/0116984 | A1 | 5/2007 | Park et al. |

FOREIGN PATENT DOCUMENTS

| | | |
|---|---|---|
| JP | 2001-525108 | 12/2001 |
| JP | 2002-506290 | 2/2002 |
| JP | 2004-087395 A | 3/2004 |
| WO | WO-2004/016709 | 2/2004 |
| WO | WO-2004/020373 | 3/2004 |
| WO | WO-2005/121064 | 12/2005 |
| WO | WO-2006/062218 | 6/2006 |

OTHER PUBLICATIONS

Shen.J et al., "High Tg blue emitting materials for electroluminescent devices", J. Mater. Chem. (Journal of Materials Chemistry), 2005, vol. 15, No. 25, pp. 2455-2463.
International Search Report (Application No. PCT/JP2006/319401) dated Dec. 12, 2006.
Written Opinion (Application No. PCT/JP2006/319401) dated Dec. 12, 2006.
Pudzich.R, "Synthese and Charakterisierung spiroverknupfter Emitter-und Ladungstransportmaterialien mit kombinierten Funktionalitaten", http://www.chemie.uni-kassel.de/mmc/pub/diss/pudzich/dissertation-pudzich.pdf, 2002.
Kafafi.Z, Organic Electroluminscence, 2005, pp. 152-161, Taylor & Francis.
Lewis.J et al., "Highly flexible transparent electrodes for organic light-emitting diode-based displays", Applied Physics Letters, Oct. 18, 2004, vol. 85, No. 16, pp. 3450-3452, The American Institute of Physics.
Zhu.R et al., "Electroluminescent Materials Based on Spirobifluorene", Chemistry Online 4th period, 2005, pp. 241-252.
Chinese Office Action (Application No. 201310493078.7) dated Nov. 15, 2014.
Taiwanese Office Action (Application No. 104105315) dated Aug. 18, 2015.
Chinese Office Action (Application No. 201410529614.9) dated Feb. 22, 2016.

* cited by examiner

SPIROFLUORENE DERIVATIVE, MATERIAL FOR LIGHT-EMITTING ELEMENT, LIGHT-EMITTING ELEMENT, LIGHT-EMITTING DEVICE, AND ELECTRONIC DEVICE

TECHNICAL FIELD

The present invention relates to a novel material. In particular, the present invention relates to a material which is ideal for use in a light-emitting element in which an organic compound is used in at least one part. In addition, the present invention relates to a light-emitting element, a light-emitting device, and an electronic device which include the material.

BACKGROUND ART

A light-emitting device using a light-emitting element which includes a layer containing an organic material between a pair of electrodes and emits light when current flows between the electrodes has been developed. Such a light-emitting device has the advantage of being thin and light, compared with other display devices which are now called thin display devices. Such a device also has high visibility since it is a self light-emitting element, and has a fast response speed. Therefore, this kind of light-emitting device has been actively developed as a next-generation display device, and has partly come into practical use.

The layer containing an organic compound provided between electrodes may have either a single layer structure including one light-emitting layer or a layered structure including layers having different functions from each other; however, the latter, a function-separated type layered structure, is often employed. As an example of the function-separated type layered structure, a structure where a hole injecting layer, a hole transporting layer, a light-emitting layer, an electron transporting layer, and an electron injecting layer are sequentially stacked over an electrode serving as an anode is typical, and each layer is formed using a material specific to each function. Note that a layer having two or more kinds of these functions such as a layer having both functions of a light-emitting layer and an electron transporting layer or a layer having another function such as a carrier blocking layer may be used.

Materials used for these functional layers are required to be materials specific to functions each layer serves and to have high heat resistance, since the heat resistance of the material itself greatly affects heat resistance of the light-emitting element. The materials are also required to be materials which do not adversely affect another layer when forming a layered structure, and research has been carried out to seek better materials. For example, because 4,4'-bis[N-(3-methylphenyl)-N-phenylamino]biphenyl (abbrev.: TPD) which is conventionally used as a hole injecting material or a hole transporting material has a low glass transition temperature (Tg) of 67° C. and has low heat resistance, 4,4'-bis[N-(1-naphthyl)-N-phenylamino]biphenyl (abbrev.: NPB), which is formed by substituting a methylphenyl group in TPD for a naphthyl group so as to increase the Tg to 96° C., has been proposed and is widely utilized (for example, Reference 1: S. A. Van Slyke, C. H. Chen, and C. W. Tang, "Organic electroluminescent devices with improved stability", Appl. Phys. Lett. 69 (15), 7 Oct. 1996).

However, while NPB has a higher glass transition temperature (Tg), its energy gap is lower. Accordingly, TPD emits light of the violet region, whereas NPB emits light of the blue region. In other words, NPB can be said to be a material that has gained a better Tg than TPD by sacrificing its energy gap. NPB and TPD are often used for a hole transporting layer, and in many cases are provided adjacent to a light-emitting layer. In such cases, if the energy gap of the hole transporting layer provided adjacently is small, there is a risk that excitation energy will be transferred to the hole transporting layer from a light-emitting material or a host material excited in the light-emitting layer. When excitation energy is transferred from the light-emitting layer to the adjacent layer, light-emitting efficiency of the light-emitting element is degraded, or color purity is reduced. Degradation of light-emitting efficiency and reduction of color purity in a light-emitting element cause increase of power consumption and degradation of display quality respectively, in a light-emitting device or an electronic device using the light-emitting element. Therefore, a layer in contact with a light-emitting layer desirably has as large an energy gap as possible.

DISCLOSURE OF INVENTION

In view of the above-described situation, it is an object of the present invention to provide a novel material having a sufficient glass transition temperature (Tg) and a sufficient band gap. It is another object of the present invention to provide a material for a light-emitting element, which has sufficient heat resistance and a sufficient band gap.

A material for forming a hole transporting layer which is often formed adjacent to a light-emitting layer as described above desirably has as high an energy gap as possible. However, few reports have been made on a material having a favorable hole transporting property, a high glass transition temperature (Tg), and moreover a large energy gap.

Therefore, it is an object of the present invention to provide a novel material having a sufficient hole transporting property, a sufficiently large energy gap, and a high glass transition temperature (Tg) as a material forming a hole transporting layer.

In addition, it is another object of the present invention to provide a material for a light-emitting element, which has a sufficient hole transporting property, a sufficiently large energy gap, and a high glass transition temperature (Tg) as a material forming a hole transporting layer.

It is another object of the present invention to provide a light-emitting element having high heat resistance. It is still another object of the present invention to provide a light-emitting element having high light-emitting efficiency.

It is another object of the present invention to provide a light-emitting device having high heat resistance. It is still another object of the present invention to provide a light-emitting device having small power consumption.

It is an object of the present invention to provide an electronic device having high heat resistance. It is still another object of the present invention to provide an electronic device having small power consumption. It is yet still another object of the present invention to provide an electronic device having high display quality.

One feature of the present invention is a spirofluorene derivative represented by General Formula 1. (In the formula, $R^1$ is any one of hydrogen, an alkyl group having 1 to 4 carbon atoms, or a group represented by General Formula 2. Each of $R^2$ and $R^3$ is hydrogen or an alkyl group having 1 to 4 carbon atoms and may be identical or different. $R^4$ is an aryl group having 6 to 15 carbon atoms. Each of $R^5$ and $R^6$ is any one of hydrogen, an alkyl group having 1 to 4 carbon atoms, or an aryl group having 6 to 15 carbon atoms and may be identical or different.)

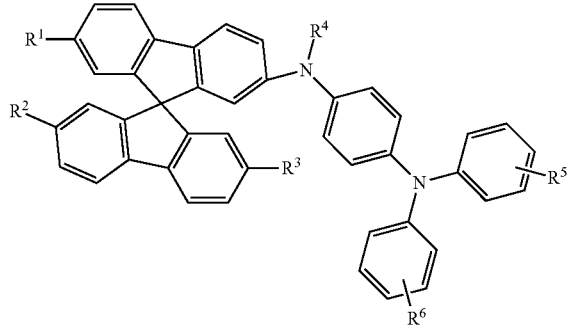

(1)

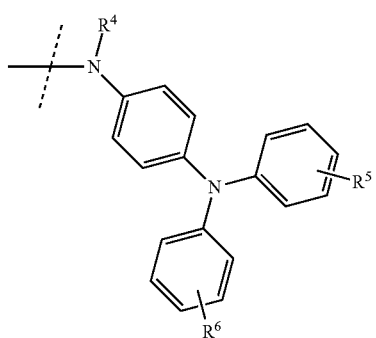

(2)

One feature of the present invention is a spirofluorene derivative represented by General Formula 3. (In the formula, $R^7$ is any one of hydrogen, an alkyl group having 1 to 4 carbon atoms, or a group represented by General Formula 4. Each of $R^1$ and $R^9$ is hydrogen or an alkyl group having 1 to 4 carbon atoms and may be identical or different. $R^{10}$ is an aryl group having 6 to 15 carbon atoms. Each of $R^{11}$ and $R^{12}$ is any one of hydrogen, an alkyl group having 1 to 4 carbon atoms, or an aryl group having 6 to 15 carbon atoms and may be identical or different.)

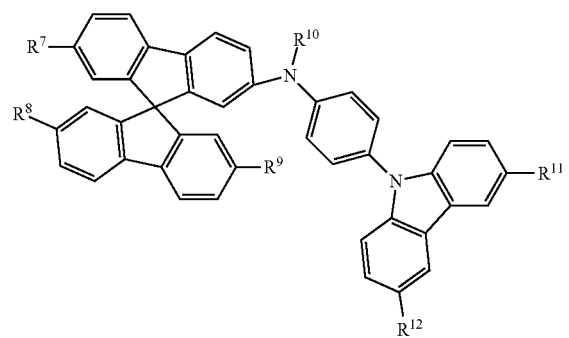

(3)

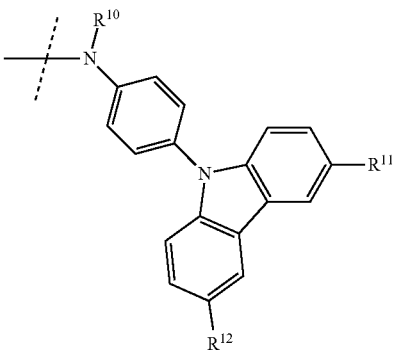

(4)

One feature of the present invention is a spirofluorene derivative represented by General Formula 5. (In the formula, $R^{13}$ is any one of hydrogen, an alkyl group having 1 to 4 carbon atoms, or a group represented by General Formula 6. Each of $R^{14}$ and $R^{15}$ is hydrogen or an alkyl group having 1 to 4 carbon atoms and may be identical or different. $R^1$ (is an aryl group having 6 to 15 carbon atoms. $R^{17}$ is any one of hydrogen, an alkyl group having 1 to 4 carbon atoms, or an aryl group having 6 to 15 carbon atoms. $R^{18}$ is an alkyl group having 1 to 4 carbon atoms or an aryl group having 6 to 15 carbon atoms.)

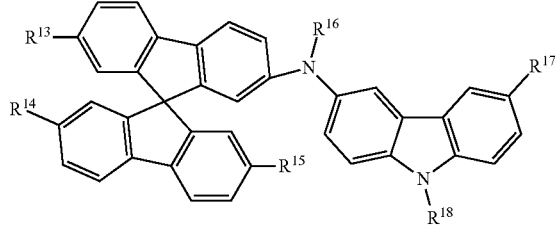

(5)

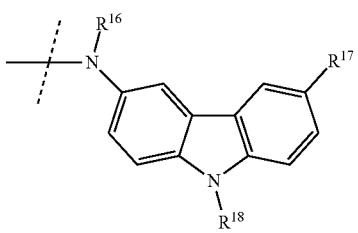

(6)

One feature of the present invention is a spirofluorene derivative represented by General Formula 7. (In the formula, $R^{19}$ is any one of hydrogen, an alkyl group having 1 to 4 carbon atoms, or a group represented by General Formula 8. Each of $R^{20}$ and $R^{21}$ is hydrogen or an alkyl group having 1 to 4 carbon atoms and may be identical or different. $R^{22}$ is any one of hydrogen, an alkyl group having 1 to 4 carbon atoms, or an aryl group having 6 to 15 carbon atoms. Each of $R^{23}$ and $R^{24}$ is any one of hydrogen, an alkyl group having 1 to 4 carbon atoms, or an aryl group having 6 to 15 carbon atoms and may be identical or different.)

(7)

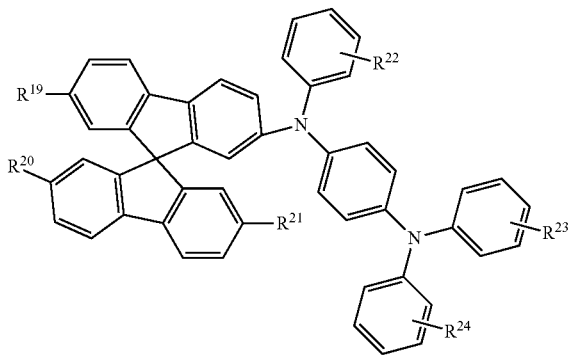

(8)

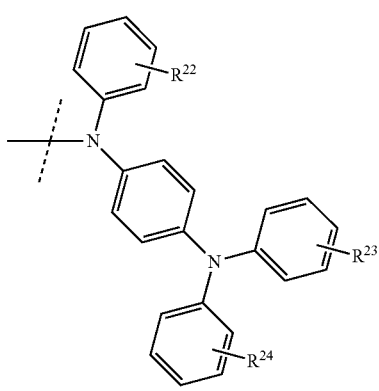

One feature of the present invention is a spirofluorene derivative represented by General Formula 9. (In the formula, $R^{25}$ is any one of hydrogen, an alkyl group having 1 to 4 carbon atoms, or a group represented by General Formula 10. Each of $R^{26}$ and $R^{27}$ is hydrogen or an alkyl group having 1 to 4 carbon atoms and may be identical or different. $R^{28}$ is any one of hydrogen, an alkyl group having 1 to 4 carbon atoms, or an aryl group having 6 to 15 carbon atoms. Each of $R^{29}$ and $R^{30}$ is any one of hydrogen, an alkyl group having 1 to 4 carbon atoms, or an aryl group having 6 to 15 carbon atoms and may be identical or different.)

(9)

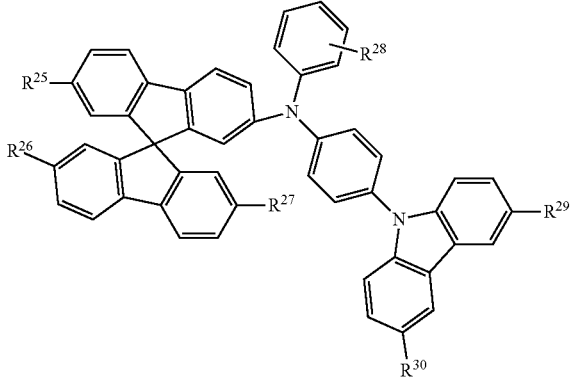

(10)

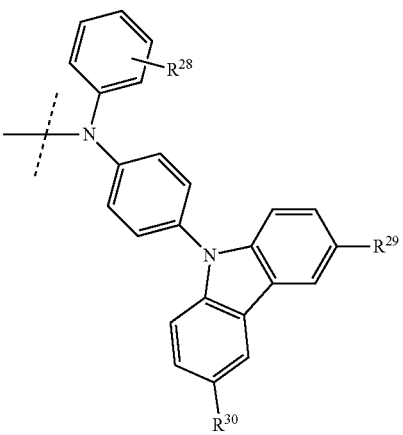

One feature of the present invention is a spirofluorene derivative represented by General Formula 11. (In the formula, $R^{31}$ is any one of hydrogen, an alkyl group having 1 to 4 carbon atoms, or a group represented by General Formula 12. Each of $R^{32}$ and $R^{33}$ is hydrogen or an alkyl group having 1 to 4 carbon atoms and may be identical or different. $R^{34}$ is any one of hydrogen, an alkyl group having 1 to 4 carbon atoms, or an aryl group having 6 to 15 carbon atoms. $R^{35}$ is any one of hydrogen, an alkyl group having 1 to 4 carbon atoms, or an aryl group having 6 to 15 carbon atoms. $R^{36}$ is any one of hydrogen, an alkyl group having 1 to 4 carbon atoms, or an aryl group having 6 to 15 carbon atoms.)

(11)

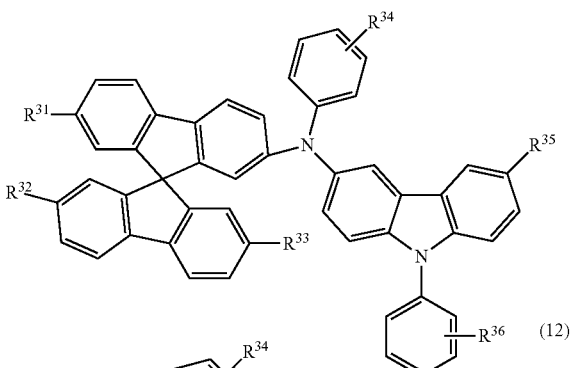

(12)

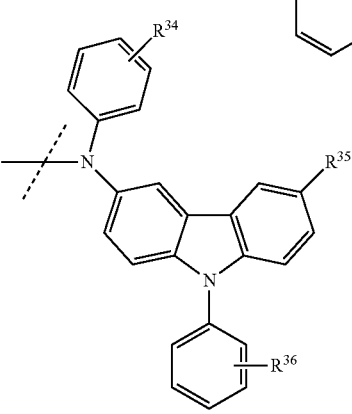

One feature of the present invention is a spirofluorene derivative represented by General Formula 13. (In the formula, $R^{37}$ is any one of hydrogen, an alkyl group having 1 to 4 carbon atoms, or a group represented by General Formula 14. Each of $R^{38}$ and $R^{39}$ is hydrogen or an alkyl group having 1 to 4 carbon atoms and may be identical or different.)

(13)

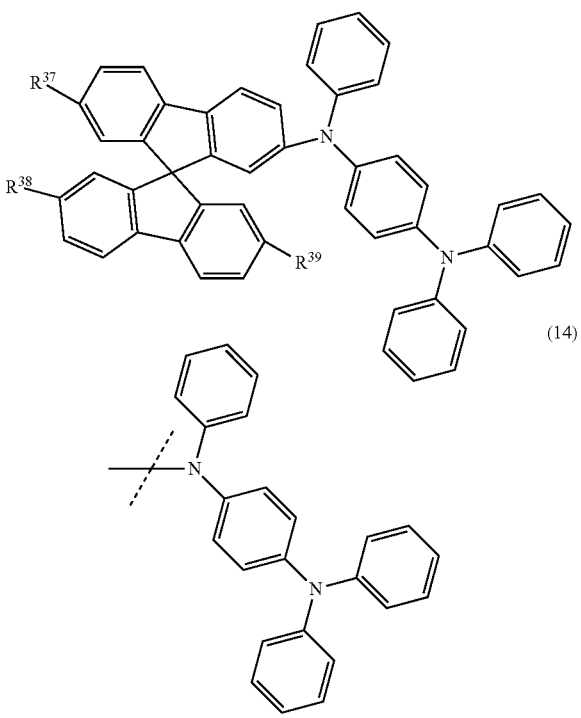

(14)

One feature of the present invention is a spirofluorene derivative represented by General Formula 15. (In the formula, $R^{40}$ is any one of hydrogen, an alkyl group having 1 to 4 carbon atoms, or a group represented by General Formula 16. Each of $R^{41}$ and $R^{42}$ is hydrogen or an alkyl group having 1 to 4 carbon atoms and may be identical or different.)

(15)

(16)

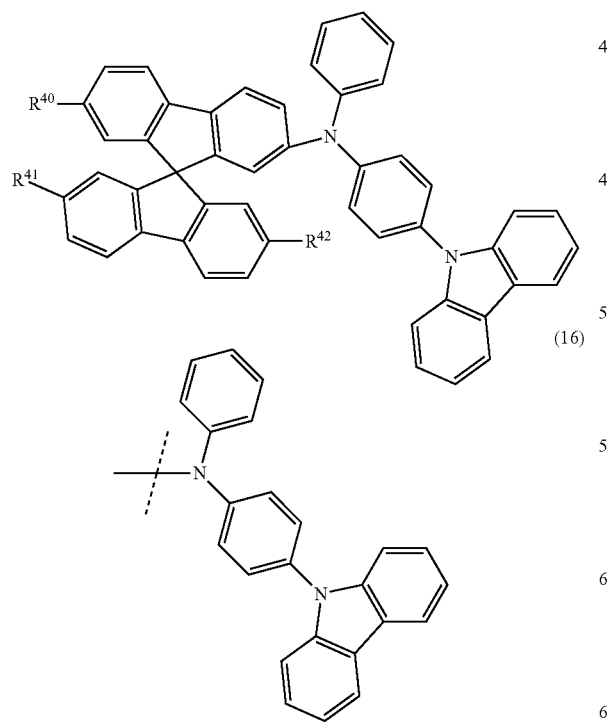

One feature of the present invention is a spirofluorene derivative represented by General Formula 17. (In the formula, $R^{43}$ is any one of hydrogen, an alkyl group having 1 to 4 carbon atoms, or a group represented by General Formula 18. Each of $R^{44}$ and $R^{45}$ is hydrogen or an alkyl group having 1 to 4 carbon atoms and may be identical or different.)

(17)

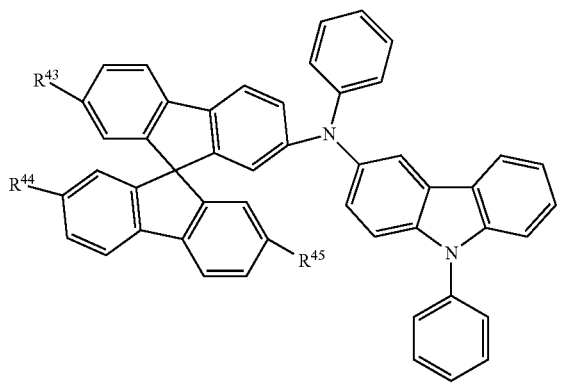

(18)

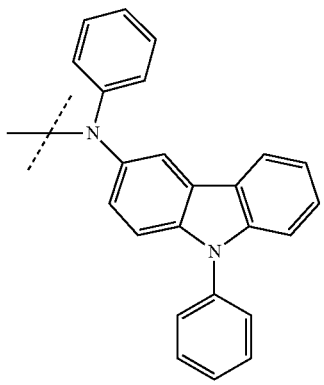

One feature of the present invention is a spirofluorene derivative represented by General Formula 19. (In the formula, each of $R^{46}$ and $R^{47}$ is hydrogen or an alkyl group having 1 to 4 carbon atoms and may be identical or different.)

(19)

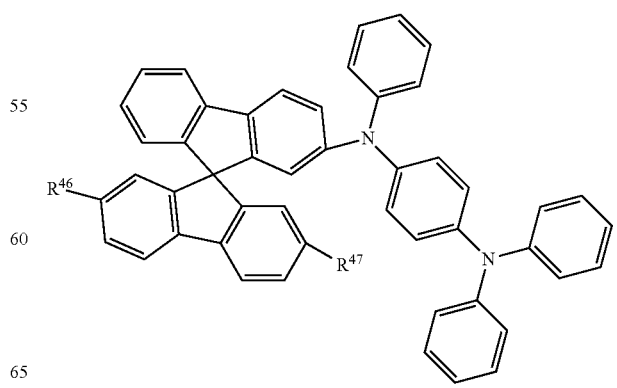

One feature of the present invention is a spirofluorene derivative represented by General Formula 20. (In the formula, each of $R^{48}$ and $R^{49}$ is hydrogen or an alkyl group having 1 to 4 carbon atoms and may be identical or different.)

(20)

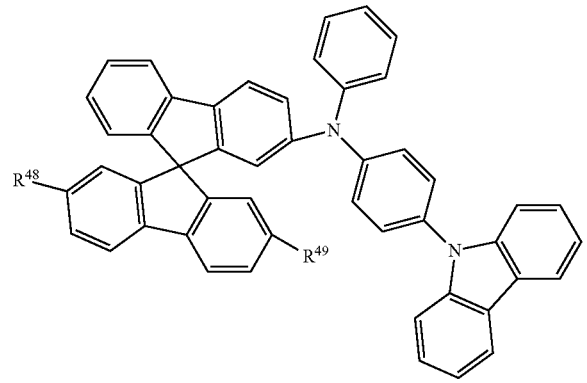

One feature of the present invention is a spirofluorene derivative represented by General Formula 21. (In the formula, each of $R^{50}$ and $R^{51}$ is hydrogen or an alkyl group having 1 to 4 carbon atoms and may be identical or different.)

(21)

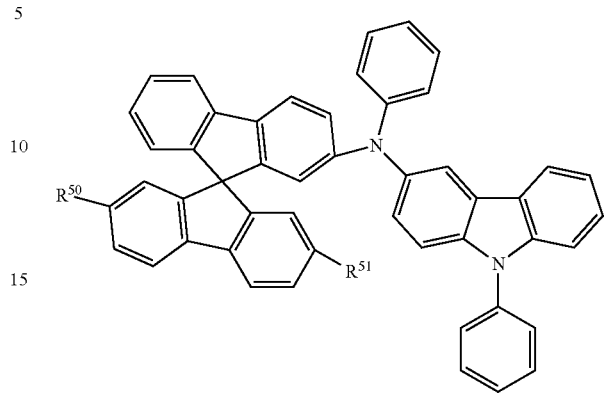

One feature of the present invention is a spirofluorene derivative represented by General Formula 22. (In the formula, each of $R^{52}$ and $R^{53}$ is hydrogen or an alkyl group having 1 to 4 carbon atoms and may be identical or different.)

(22)

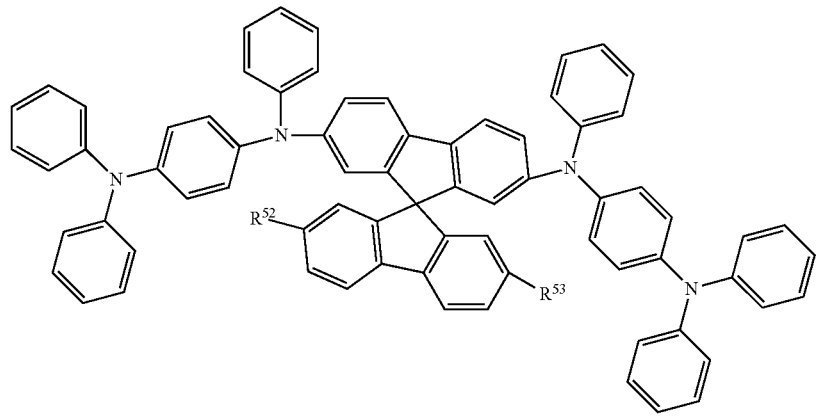

One feature of the present invention is a spirofluorene derivative represented by General Formula 23. (In the formula, each of $R^{54}$ and $R^{55}$ is hydrogen or an alkyl group having 1 to 4 carbon atoms and may be identical or different.)

(23)

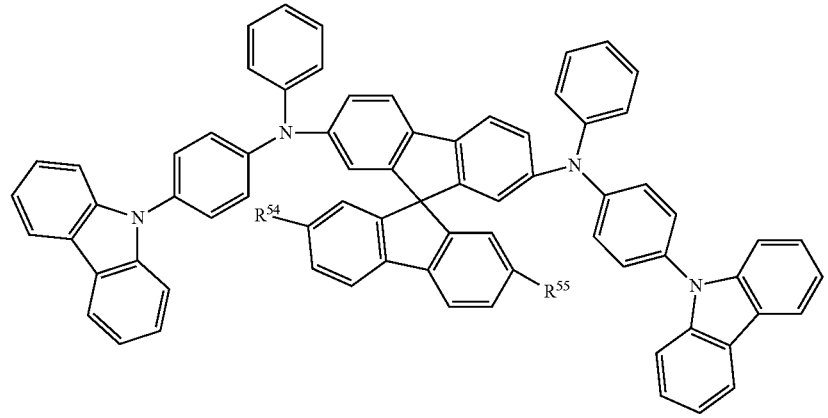

One feature of the present invention is a spirofluorene derivative represented by General Formula 24. (In the formula, each of $R^{56}$ and $R^{57}$ is hydrogen or an alkyl group having 1 to 4 carbon atoms and may be identical or different.)

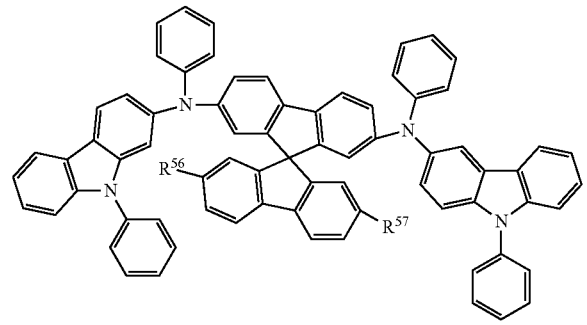

(24)

One feature of the present invention is a spirofluorene derivative represented by Structural Formula 25.

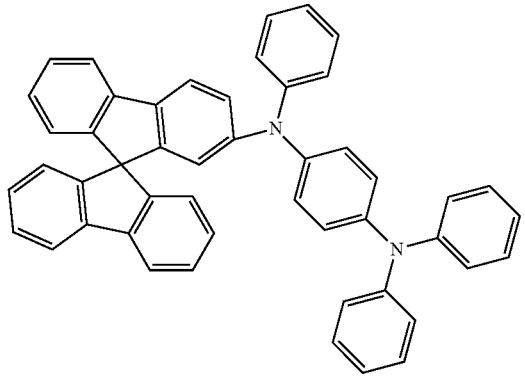

(25)

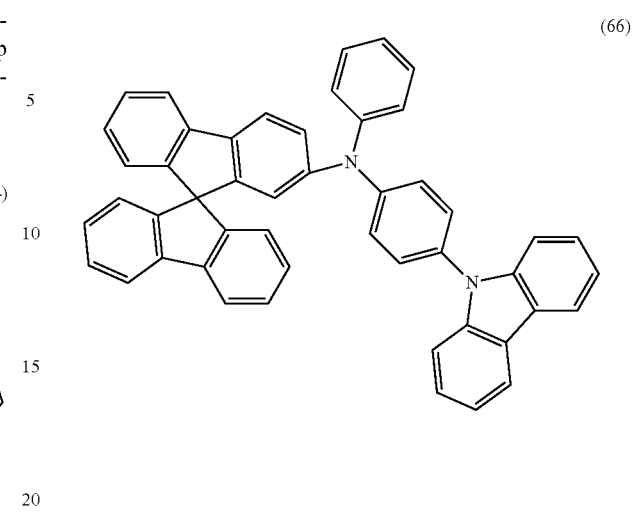

(66)

One feature of the present invention is a spirofluorene derivative represented by Structural Formula (35).

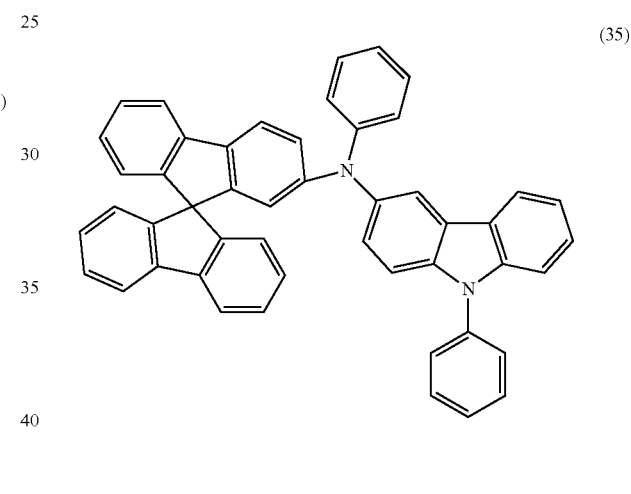

(35)

One feature of the present invention is a spirofluorene derivative represented by Structural Formula (26).

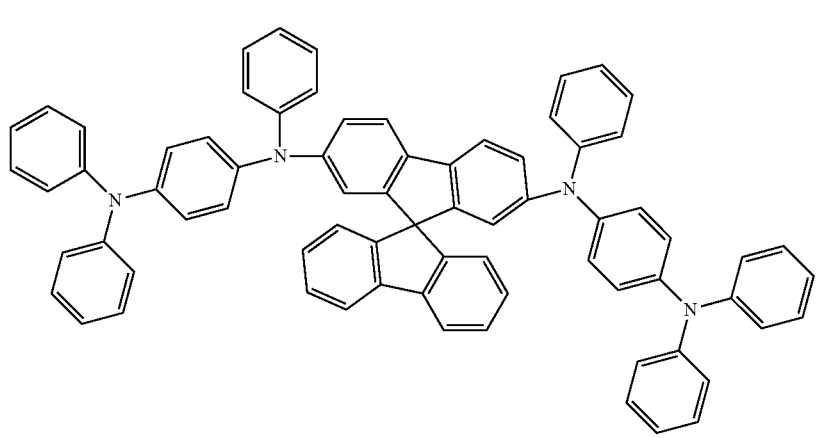

(26)

One feature of the present invention is a spirofluorene derivative represented by Structural Formula (66).

One feature of the present invention is a spirofluorene derivative represented by Structural Formula (67).

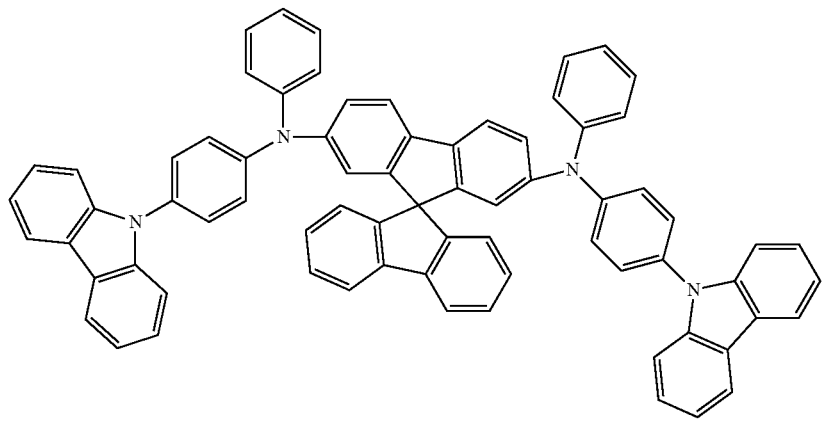

(67)

One feature of the present invention is a spirofluorene derivative represented by Structural Formula 30.

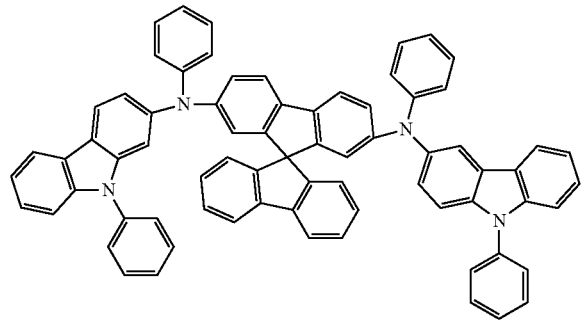

(30)

One feature of the present invention is a material for a light-emitting element containing any of the above-described spirofluorene derivatives.

One feature of the present invention is a light-emitting element containing any of the above-described spirofluorene derivatives.

One feature of the present invention is a light-emitting device including the above-described light-emitting element and a control circuit which controls light emission of the light-emitting element.

One feature of the present invention is an electronic device including a display portion using the above-described light-emitting element and a control circuit which controls the light-emitting element.

A spirofluorene derivative of the present invention is a novel material having a high glass transition temperature (Tg) and a wide energy gap. In addition, a spirofluorene derivative of the present invention is a material for a light-emitting element, which has a high Tg and a wide band gap.

A spirofluorene derivative of the present invention is a novel material having a sufficient hole transporting property, a sufficiently large energy gap, and a high glass transition temperature (Tg) as a material forming a hole transporting layer.

A spirofluorene derivative of the present invention is a material for a light-emitting element, which has a sufficient hole transporting property, a sufficiently large energy gap, and a high glass transition temperature (Tg) as a material forming a hole transporting layer.

A light-emitting element of the present invention is a light-emitting element having high heat resistance, and also a light-emitting element having high light-emitting efficiency.

A light-emitting device of the present invention is a light-emitting device having high heat resistance, and also a light-emitting device having small power consumption.

An electronic device of the present invention is an electronic device having high heat resistance, and also an electronic device having small power consumption.

BRIEF DESCRIPTION OF DRAWINGS

In the accompanying drawings:

FIGS. 9A to 9E show examples of an electronic device which the present invention can be applied to;

BEST MODE FOR CARRYING OUT THE INVENTION

Figure 1:
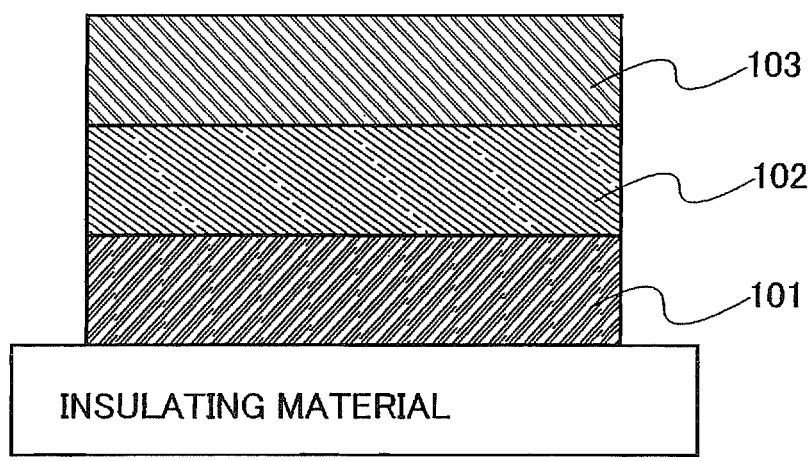
FIG. 1 shows a light-emitting element of the present invention.

Embodiment modes and examples of the present invention will be described with reference to the drawings. Note that it is easily understood by those skilled in the art that the invention is not limited to the following descriptions, and various changes may be made in forms and details without departing from the spirit and the scope of the invention. Therefore, the invention should not be limited to the descriptions of the embodiment modes and examples below.

Embodiment Mode 1

Embodiment Mode 1 will describe spirofluorene derivatives of the present invention.

A spirofluorene derivative of the present invention is shown in General Formula 1.

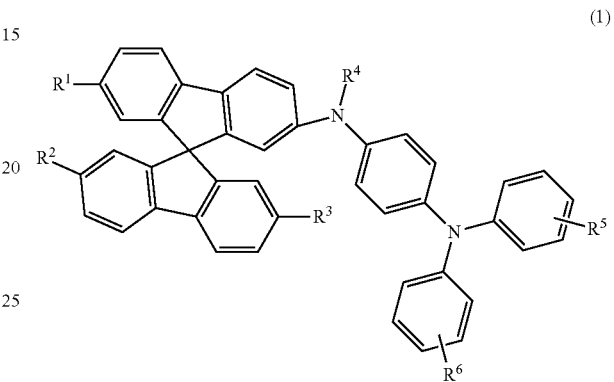

(1)

In the formula, $R^1$ is any one of hydrogen, an alkyl group having 1 to 4 carbon atoms, or a group represented by General Formula 2. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^1$, any one of hydrogen, a t-butyl group, or a group represented by General Formula 2 is particularly preferable.

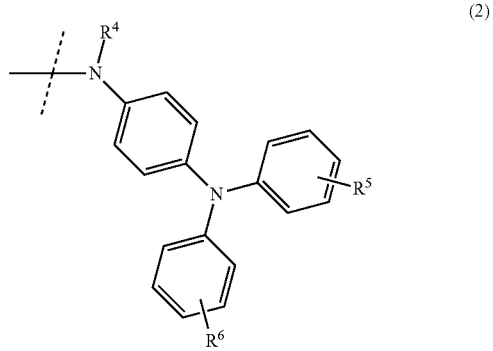

(2)

In the formula, each of $R^2$ and $R^3$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^2$ and $R^3$, hydrogen or a t-butyl group is particularly preferable. $R^2$ and $R^3$ may be identical or different.

$R^4$ is an aryl group having 6 to 15 carbon atoms. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 1 into a compound having a larger energy gap, $R^4$ is preferably a group which does not have a condensed ring skeleton, selected from among aryl groups having 6 to 15 carbon atoms. Each of the aryl groups having 6 to 15 carbon atoms may have a substituent, and an alkyl group having 1 to 4 carbon atoms or an aryl group having 6 to 15 carbon atoms can be used as the substituent. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^4$, an unsubstituted phenyl group is particularly preferable.

In the formula, each of $R^5$ and $R^6$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^5$ and $R^6$, hydrogen is particularly preferable. Note that $R^5$ and $R^6$ may be identical or different and may have a substituent or no substituent.

A spirofluorene derivative of the present invention is shown in General Formula 3.

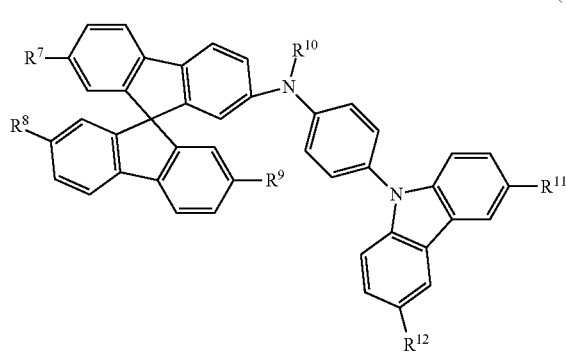

(3)

In the formula, $R^7$ is any one of hydrogen, an alkyl group having 1 to 4 carbon atoms, or a group represented by General Formula 4. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^7$, any one of hydrogen, a t-butyl group, or a group represented by General Formula 4 is particularly preferable.

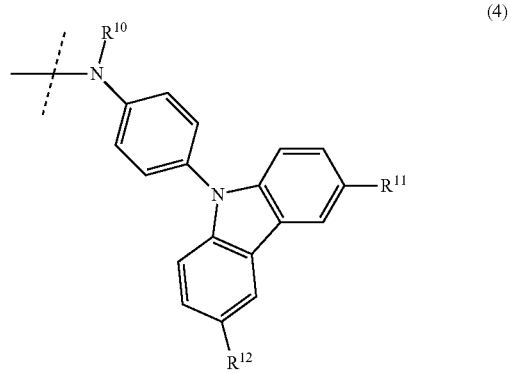

(4)

In the formula, each of $R^8$ and $R^9$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^8$ and $R^9$, hydrogen or a t-butyl group is particularly preferable. Note that $R^8$ and $R^9$ may be identical or different.

$R^{10}$ is an aryl group having 6 to 15 carbon atoms. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 3 into a compound having a larger energy gap, $R^{10}$ is preferably a group which does not have a condensed ring skeleton. Each of the aryl groups having 6 to 15 carbon atoms may have a substituent, and an alkyl group having 1 to 4 carbon atoms or an aryl group having 6 to 15 carbon atoms can be used as the substituent. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{10}$, an unsubstituted phenyl group is particularly preferable.

In the formula, each of $R^{11}$ and $R^{12}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{11}$ and $R^{12}$, hydrogen is particularly preferable. Note that $R^{11}$ and $R^{12}$ may be identical or different and may have a substituent or no substituent.

A spirofluorene derivative of the present invention is represented by General Formula 5.

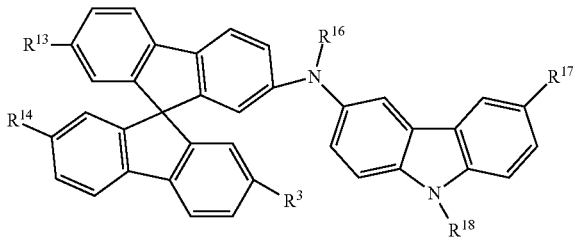

(5)

In the formula, $R^{13}$ is any one of hydrogen, an alkyl group having 1 to 4 carbon atoms, or a group represented by General Formula 6. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{13}$, any one of hydrogen, a t-butyl group, or a group represented by General Formula 6 is particularly preferable.

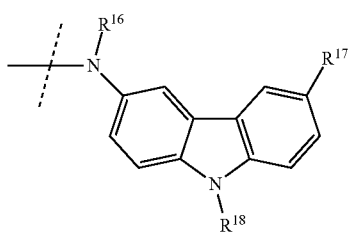

(6)

In the formula, each of $R^{14}$ and $R^{15}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{14}$ and $R^{15}$, hydrogen or a t-butyl group is particularly preferable. Note that $R^{14}$ and $R^{15}$ may be identical or different.

$R^{16}$ is an aryl group having 6 to 15 carbon atoms. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 5 into a compound having a larger energy gap, $R^{16}$ is preferably a group which does not have a condensed ring skeleton. Each of the aryl groups having 6 to 15 carbon atoms may have a substituent, and an alkyl group having 1 to 4 carbon atoms or an aryl group having 6 to 15 carbon atoms can be used as the substituent. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{16}$, an unsubstituted phenyl group is particularly preferable.

In the formula, $R^{17}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{17}$, hydrogen is particularly preferable. Note that $R^{17}$ may have a substituent or no substituent.

In the formula, $R^{18}$ is either an alkyl group having 1 to 4 carbon atoms or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 5 into a compound having a larger energy gap, $R^{18}$ is preferably a group which does not have a condensed ring skeleton, which is selected from among alkyl groups having 1 to 4 carbon atoms and aryl groups having 6 to 15 carbon atoms. Each of the aryl groups having 6 to 15 carbon atoms may have a substituent, and an alkyl group having 1 to 4 carbon atoms or an aryl group having 6 to 15 carbon atoms can be used as the substituent. As the alkyl group having 1 to 4 carbon atoms serving as a substituent, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{18}$, an unsubstituted phenyl group is particularly preferable.

A spirofluorene derivative of the present invention is represented by General Formula 7.

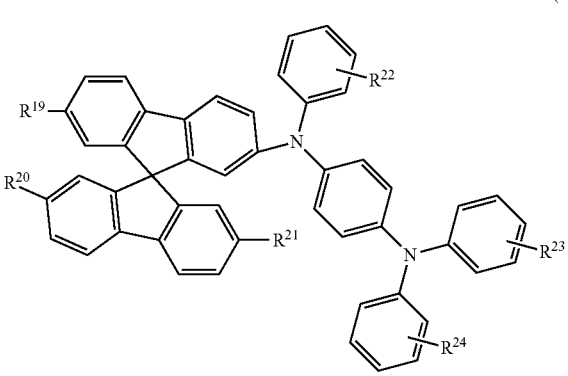

(7)

In the formula, $R^{19}$ is any one of hydrogen, an alkyl group having 1 to 4 carbon atoms, or a group represented by General Formula 8. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{19}$, any one of hydrogen, a t-butyl group, or a group represented by General Formula 8 is particularly preferable.

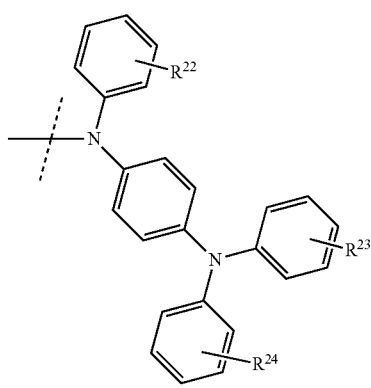

(8)

In the formula, each of $R^{20}$ and $R^{21}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{20}$ and $R^{21}$, hydrogen or a t-butyl group is particularly preferable. Note that $R^{20}$ and $R^{21}$ may be identical or different.

$R^{22}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 7 into a compound having a larger energy gap, $R^{22}$ is preferably a group which does not have a condensed ring skeleton. As $R^{22}$, hydrogen is particularly preferable.

In the formula, each of $R^{23}$ and $R^{24}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{23}$ and $R^{24}$, hydrogen is particularly preferable. Note that $R^{23}$ and $R^{24}$ may be identical or different and may have a substituent or no substituent.

A spirofluorene derivative of the present invention is represented by General Formula 9.

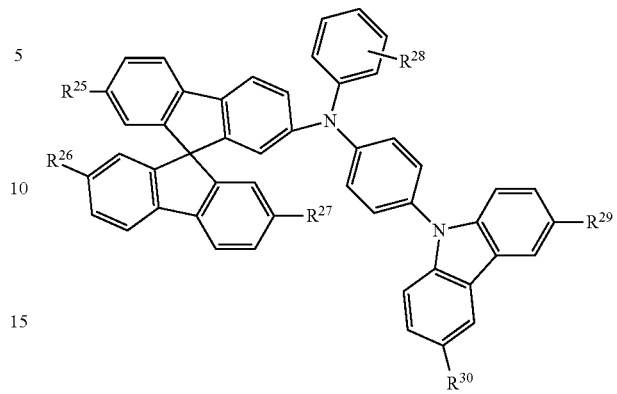

(9)

In the formula, $R^{25}$ is any one of hydrogen, an alkyl group having 1 to 4 carbon atoms, or a group represented by General Formula 10. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{25}$, any one of hydrogen, a t-butyl group, or a group represented by General Formula 10 is particularly preferable.

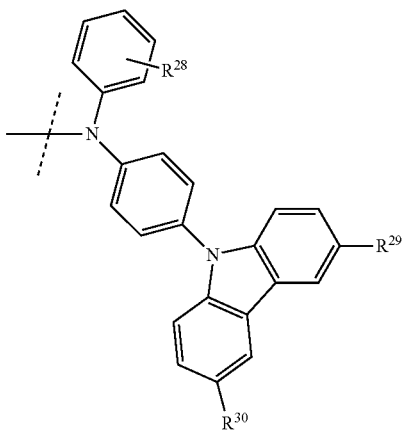

(10)

In the formula, each of $R^{26}$ and $R^{27}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{26}$ and $R^{27}$, hydrogen or a t-butyl group is particularly preferable. Note that $R^{26}$ and $R^{27}$ may be identical or different.

$R^{28}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 9 into a compound having a larger energy gap, $R^{28}$ is preferably a group which does not have a condensed ring skeleton. As $R^{28}$, hydrogen is particularly preferable.

In the formula, each of $R^{29}$ and $R^{30}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{29}$ and $R^{30}$, hydrogen is particularly preferable. Note that $R^{29}$ and $R^{30}$ may be identical or different and may have a substituent or no substituent.

A spirofluorene derivative of the present invention is represented by General Formula 11.

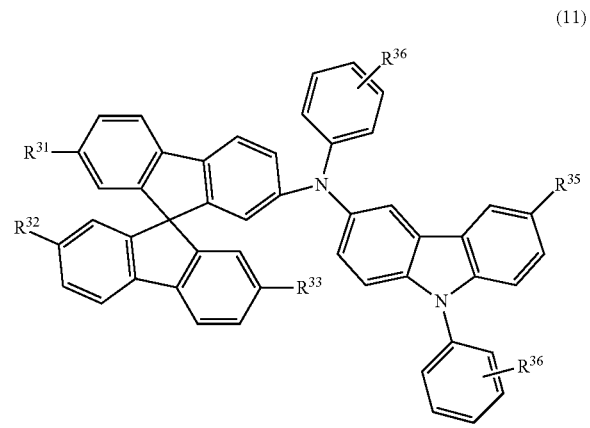

(11)

In the formula, $R^{31}$ is any one of hydrogen, an alkyl group having 1 to 4 carbon atoms, or a group represented by General Formula 12. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{31}$, any one of hydrogen, a t-butyl group, or a group represented by General Formula 12 is particularly preferable.

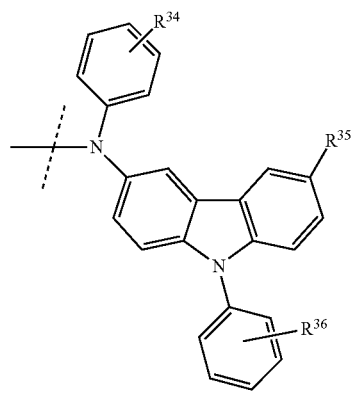

(12)

In the formula, each of $R^{32}$ and $R^{33}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{32}$ and $R^{33}$, hydrogen or a t-butyl group is particularly preferable. Note that $R^{32}$ and $R^{33}$ may be identical or different.

$R^{34}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 11 into a compound having a larger energy gap, $R^{34}$ is preferably a group which does not have a condensed ring skeleton. As $R^{34}$, hydrogen is particularly preferable.

In the formula, $R^{35}$ is any one of hydrogen, an alkyl group having 1 to 4 carbon atoms, or an aryl group having 6 to 15 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, a phenyl group, an o-biphenyl group, an m-biphenyl group, a p-biphenyl group, a fluorene-2-yl group, a 9,9-dimethylfluorene-2-yl group, a naphthyl group, or the like can be used. As $R^{35}$, hydrogen is particularly preferable. Note that $R^{35}$ may have a substituent or no substituent.

In the formula, $R^{36}$ is any one of hydrogen, an alkyl group having 1 to 4 carbon atoms, or an aryl group having 6 to 15 carbon atoms. As the alkyl group having 1 to 4 carbon atoms serving as a substituent, specifically, a methyl group, an ethyl group, an n-propyl group, an iso-propyl group, an n-butyl group, an iso-butyl group, a sec-butyl group, a t-butyl group, or the like can be used. As the aryl group having 6 to 15 carbon atoms, specifically, a phenyl group, an o-biphenyl group, an m-biphenyl group, a p-biphenyl group, a fluorene-2-yl group, a 9,9-dimethylfluorene-2-yl group, a naphthyl group, or the like can be used. In order to make the spirofluorene derivative represented by General Formula 11 into a compound having a larger energy gap, $R^{36}$ is preferably a group which does not have a condensed ring skeleton. As $R^{36}$, hydrogen is particularly preferable.

A spirofluorene derivative of the present invention is represented by General Formula 13.

(13)

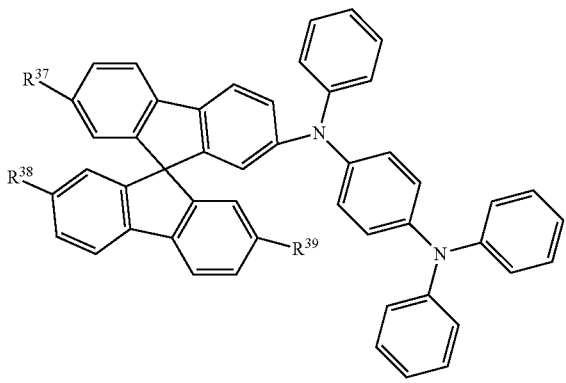

In the formula, $R^{37}$ is any one of hydrogen, an alkyl group having 1 to 4 carbon atoms, or a group represented by General Formula 14 (N-{4-(N',N'-diphenyl)anilino}aniline). As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{37}$, any one of hydrogen, a t-butyl group, or a group represented by General Formula 14 is particularly preferable.

(9)

In the formula, $R^{40}$ is any one of hydrogen, an alkyl group having 1 to 4 carbon atoms, or a group represented by General Formula 16 (a {4-(9-carbazolyl)phenyl}phenylamino group). As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{40}$, any one of hydrogen, a t-butyl group, or a group represented by General Formula 16 is particularly preferable.

(14)

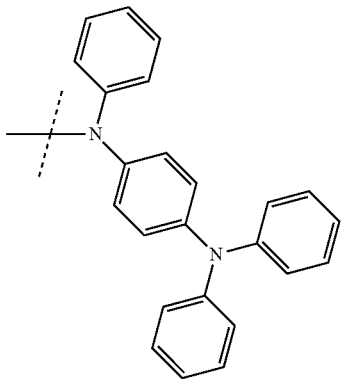

(16)

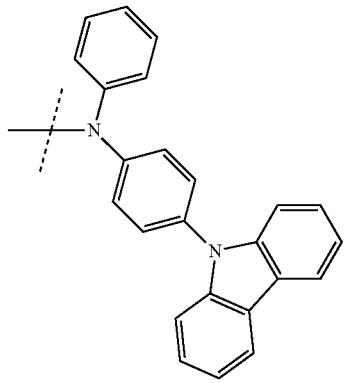

In the formula, each of $R^{38}$ and $R^{39}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{38}$ and $R^{39}$, hydrogen or a t-butyl group is particularly preferable. Note that $R^{38}$ and $R^{39}$ may be identical or different.

A spirofluorene derivative of the present invention is represented by General Formula 15.

In the formula, each of $R^{41}$ and $R^{42}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{41}$ and $R^{42}$, hydrogen or a t-butyl group is particularly preferable. Note that $R^{41}$ and $R^{42}$ may be identical or different.

A spirofluorene derivative of the present invention is represented by General Formula 17.

(17)

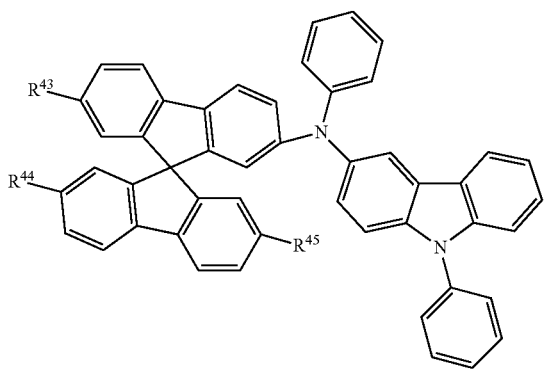

In the formula, $R^{43}$ is any one of hydrogen, an alkyl group having 1 to 4 carbon atoms, or a group represented by General Formula 18 (a [3-(9-phenylcarbazolyl)]phenylamino group). As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{43}$, any one of hydrogen, a t-butyl group, or a group represented by General Formula 18 is particularly preferable.

(18)

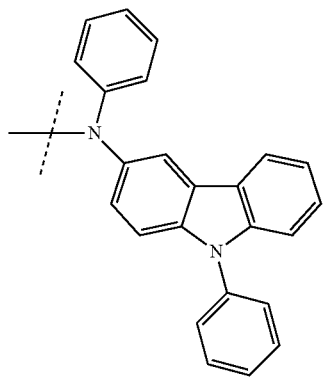

In the formula, each of $R^{44}$ and $R^{45}$ is either hydrogen or an alkyl group having 0.1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{44}$ and $R^{45}$, hydrogen or a t-butyl group is particularly preferable. Note that $R^{44}$ and $R^{45}$ may be identical or different.

A spirofluorene derivative of the present invention is represented by General Formula 19.

(19)

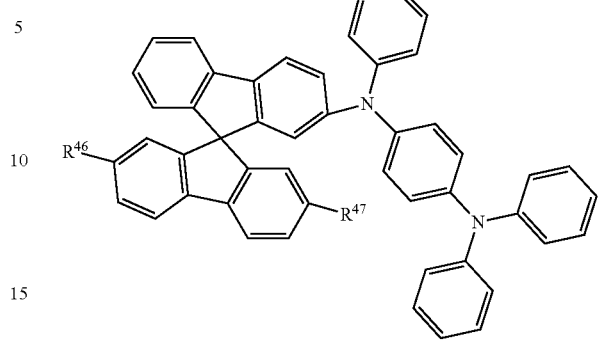

In the formula, each of $R^{46}$ and $R^{47}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{46}$ and $R^{47}$, hydrogen or a t-butyl group is particularly preferable. Note that $R^{46}$ and $R^{47}$ may be identical or different.

A spirofluorene derivative of the present invention is represented by General Formula 20.

(20)

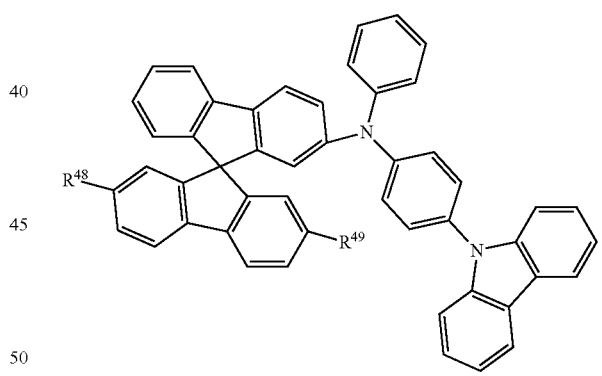

In the formula, each of $R^{48}$ and $R^{49}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{48}$ and $R^{49}$, hydrogen or a t-butyl group is particularly preferable. Note that $R^{48}$ and $R^{49}$ may be identical or different.

A spirofluorene derivative of the present invention is represented by General Formula 21.

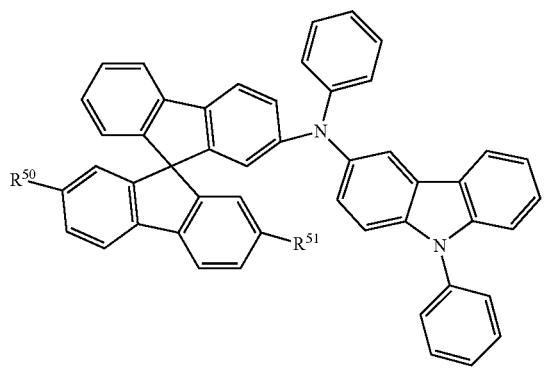

(21)

In the formula, each of $R^{50}$ and $R^{51}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{50}$ and $R^{51}$, hydrogen or a t-butyl group is particularly preferable. Note that $R^{50}$ and $R^{51}$ may be identical or different.

A spirofluorene derivative of the present invention is represented by General Formula 22.

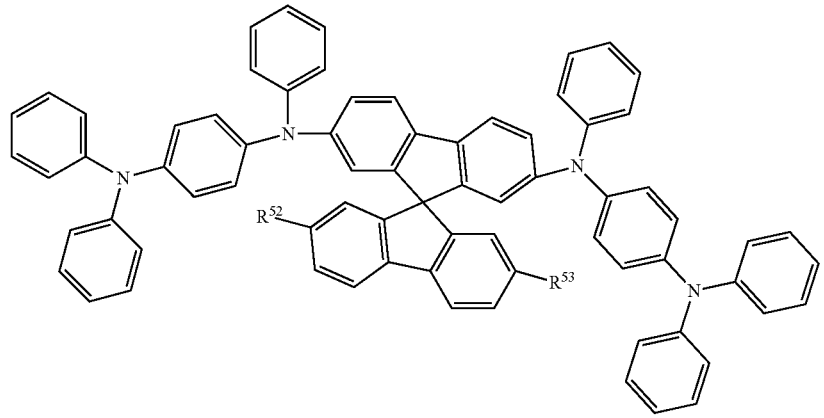

(22)

In the formula, each of $R^{52}$ and $R^{53}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{52}$ and $R^{53}$, hydrogen or a t-butyl group is particularly preferable. Note that $R^{52}$ and $R^{53}$ may be identical or different.

A spirofluorene derivative of the present invention is represented by General Formula 23.

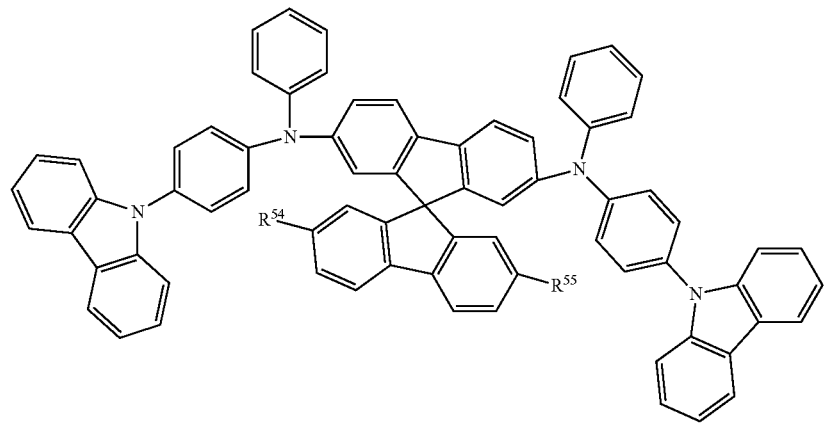

(23)

In the formula, each of $R^{54}$ and $R^{55}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{54}$ and $R^{55}$, hydrogen or a t-butyl group is particularly preferable. Note that $R^{54}$ and $R^{55}$ may be identical or different.

A spirofluorene derivative of the present invention is represented by General Formula 24.

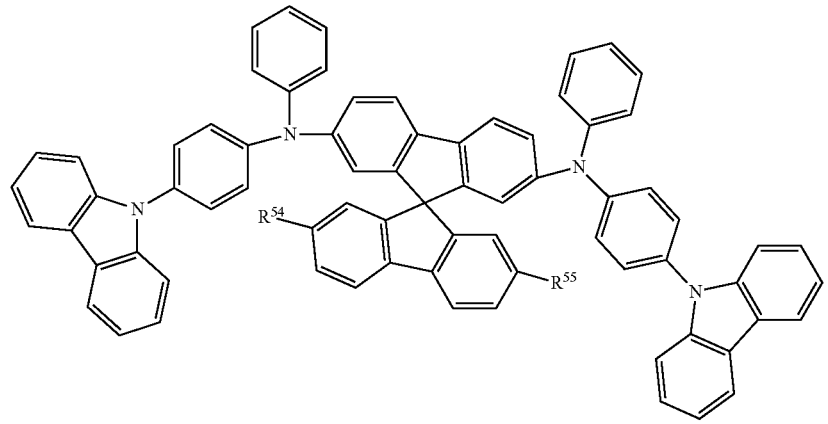

(24)

In the formula, each of $R^{56}$ and $R^{57}$ is either hydrogen or an alkyl group having 1 to 4 carbon atoms. As the alkyl group having 1 to 4 carbon atoms, specifically, a methyl group, an ethyl group, an n-propyl group, an iso-propyl group, an n-butyl group, an iso-butyl group, a sec-butyl group, a t-butyl group, or the like can be used. As $R^{56}$ and $R^{57}$, hydrogen or a t-butyl group is particularly preferable. Note that $R^{56}$ and $R^{57}$ may be identical or different.

As a spirofluorene derivative of the present invention, spirofluorene derivatives represented by Structural Formulas 25 to 110 can be used. In the formulas, Me indicates a methyl group; Et, an ethyl group; i-Pro, an iso-propyl group; n-Pro, an n-propyl group; n-Bu, an n-butyl group; i-Bu, an iso-butyl group; s-Bu, a sec-butyl group; and t-Bu, a t-butyl group. Note that a spirofluorene derivative of the present invention is not limited thereto.

(25)

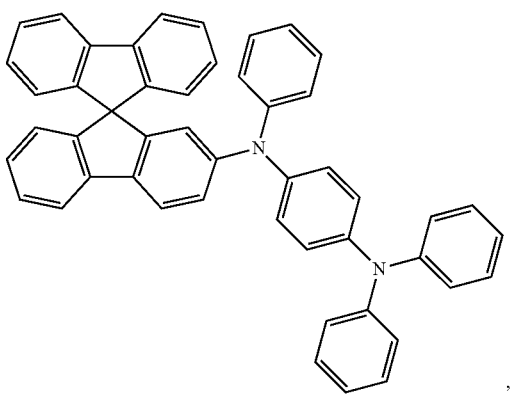

-continued (26)

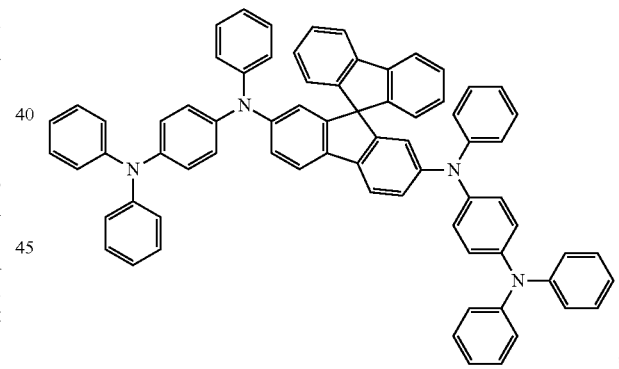

, (27)

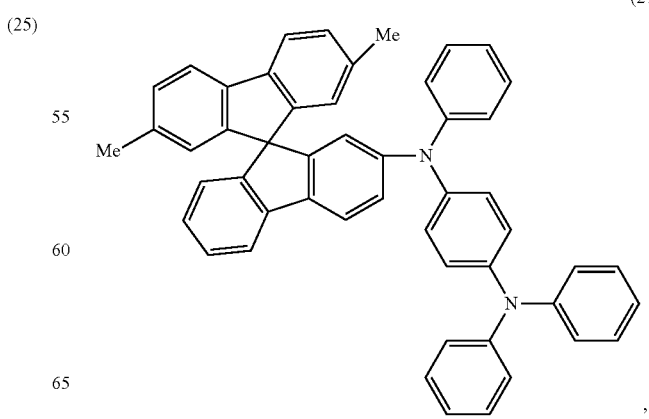

,

(28)
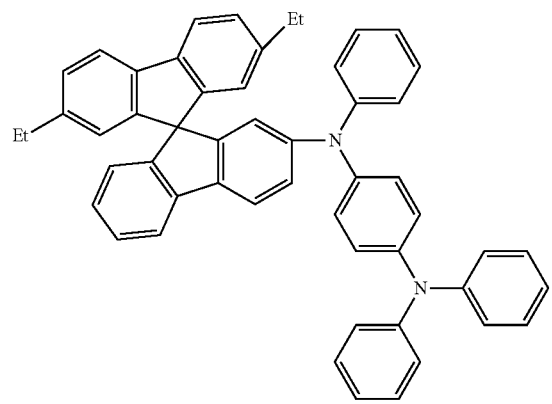
,
(29)
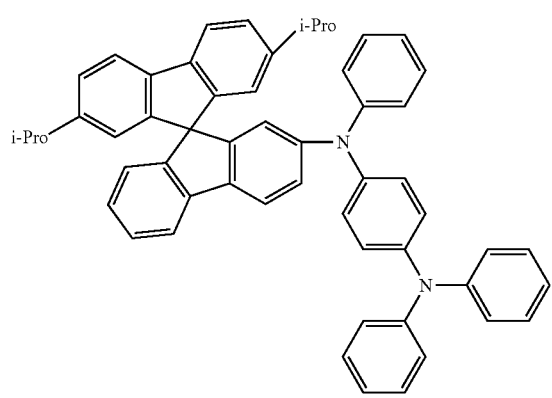
,
(30)
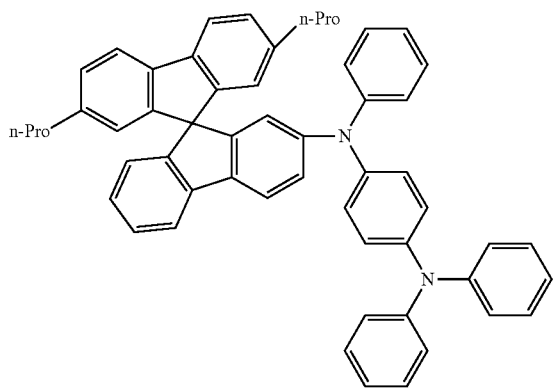
,
(31)
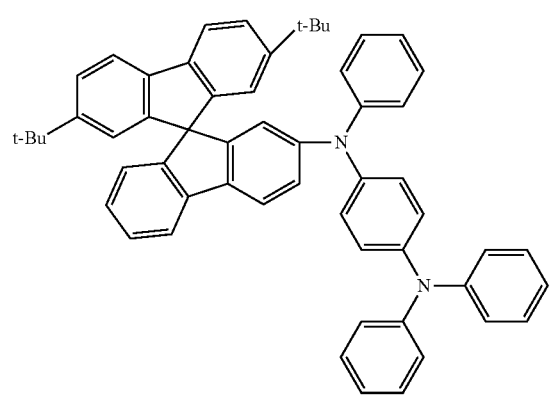
,
(32)
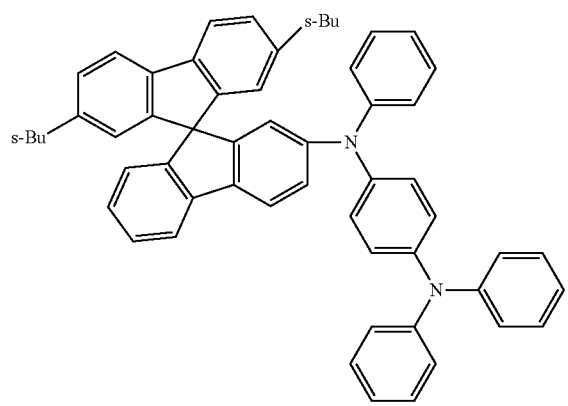
,
(33)
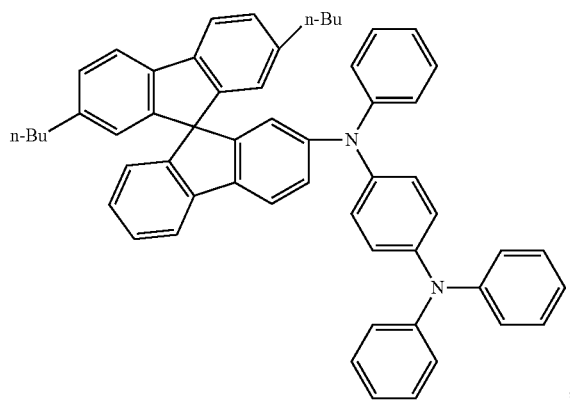
,
(34)
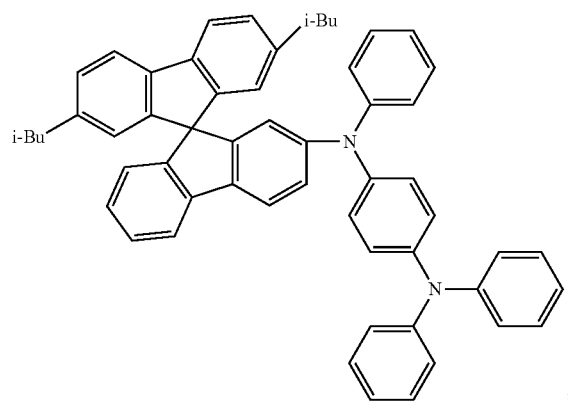
,
(35)
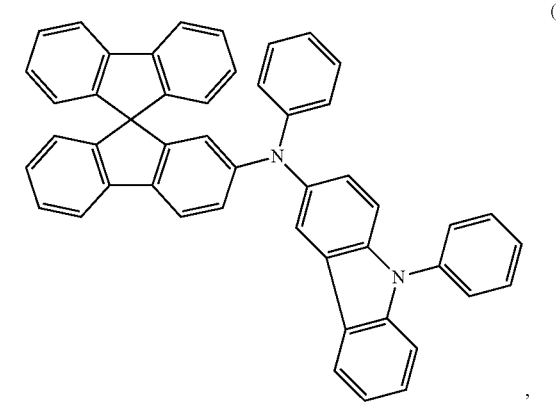
,

(36)
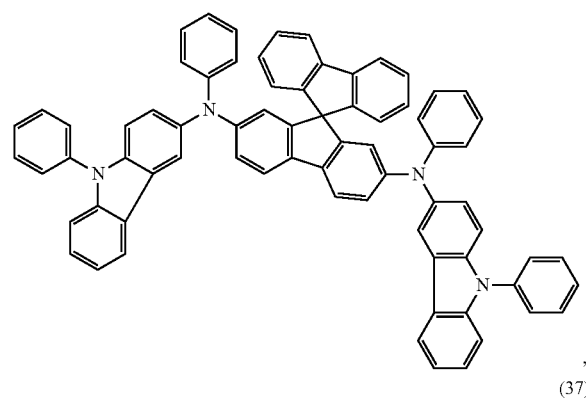
,
(37)
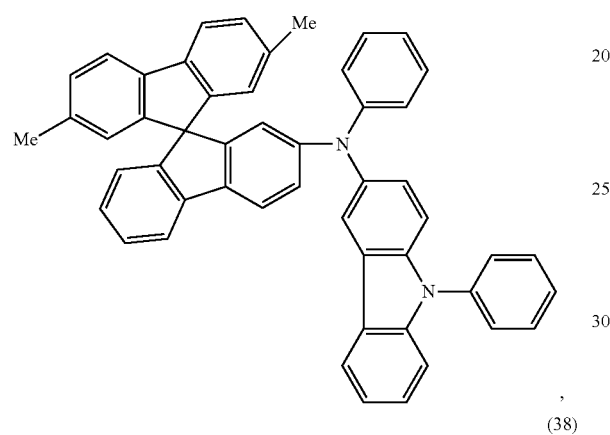
,
(38)
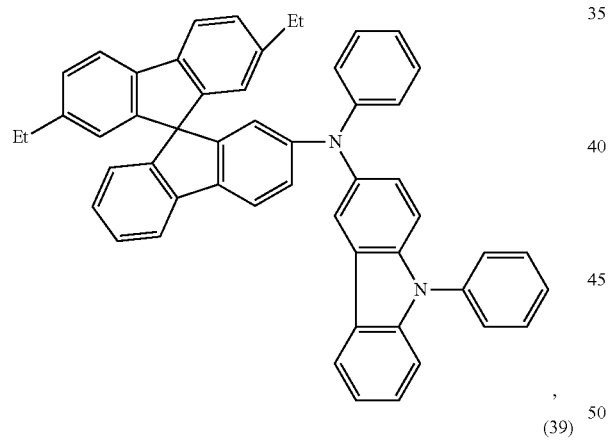
,
(39)
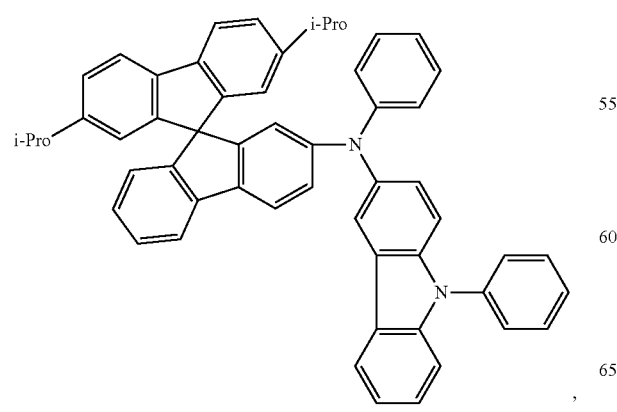
,
(40)
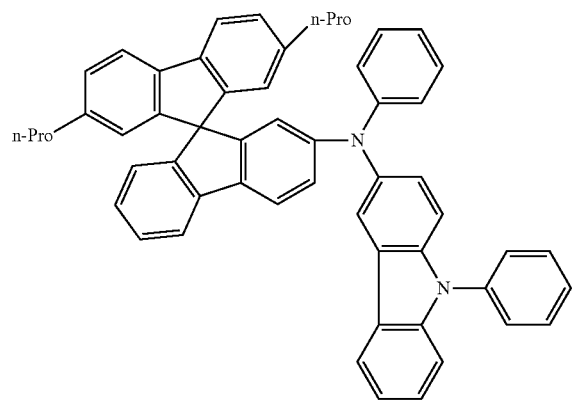
,
(41)
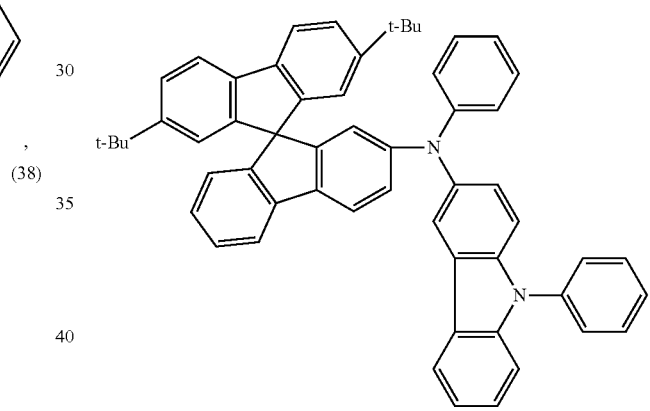
,
(42)
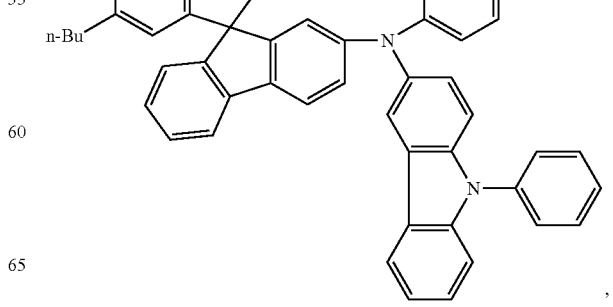
,

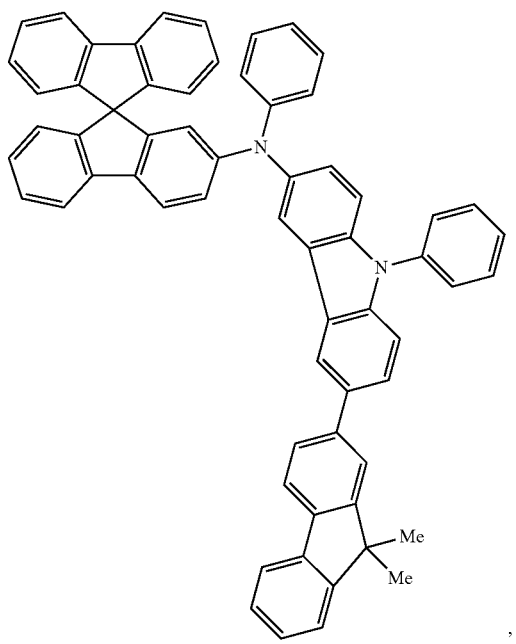
(43)
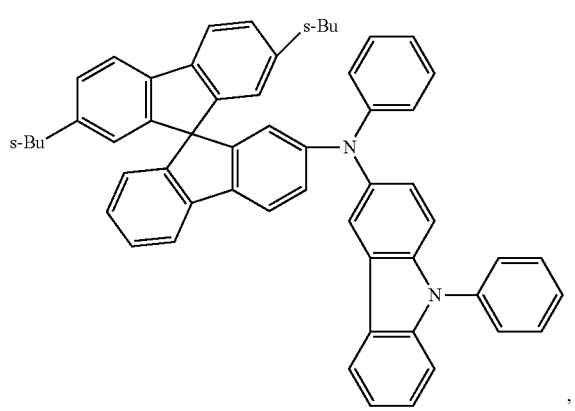
(44)
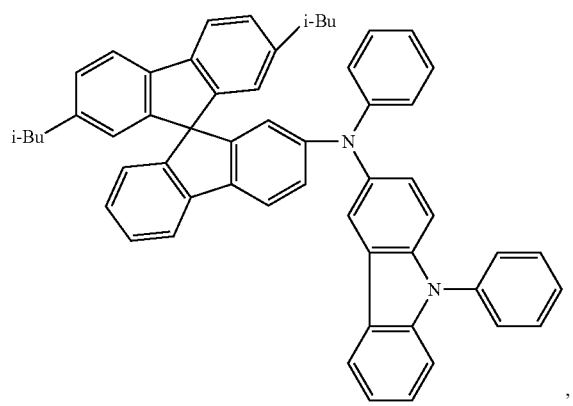
(45)
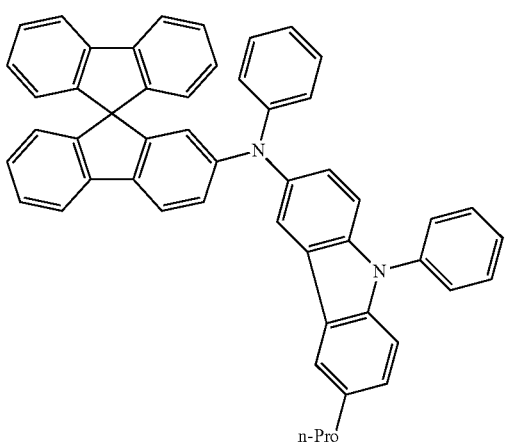
(46)
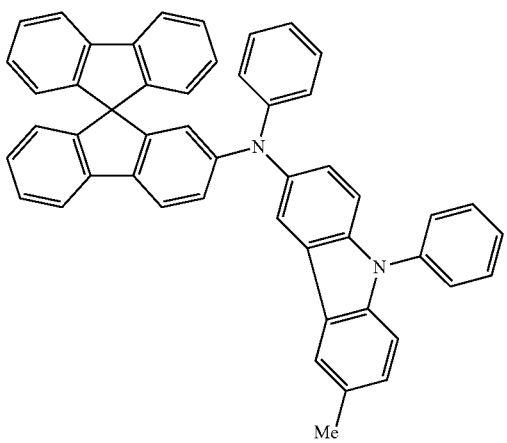
(47)
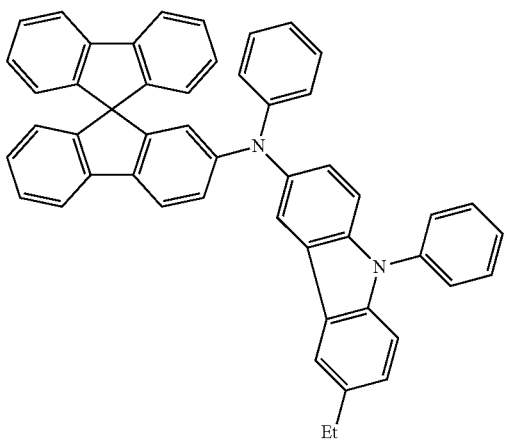
(48)

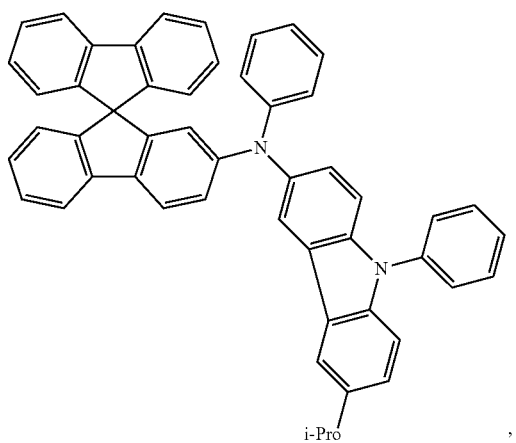
(49)
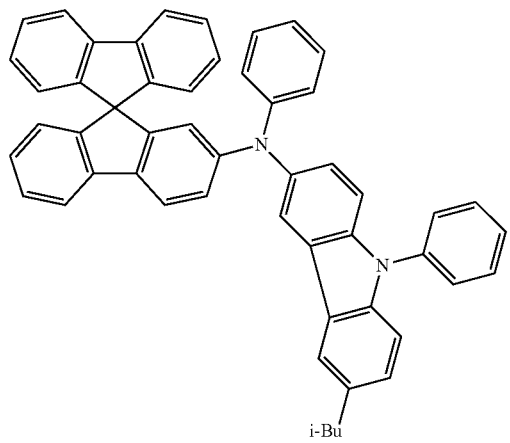
(52)
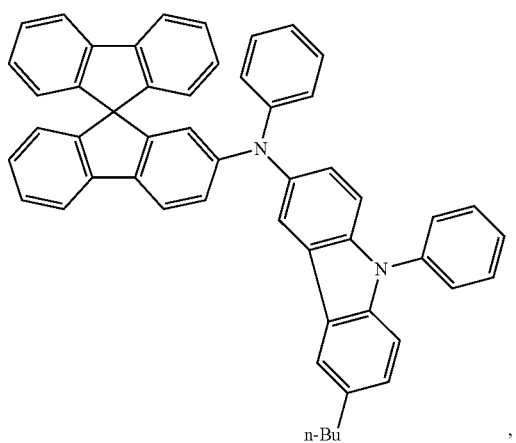
(50)
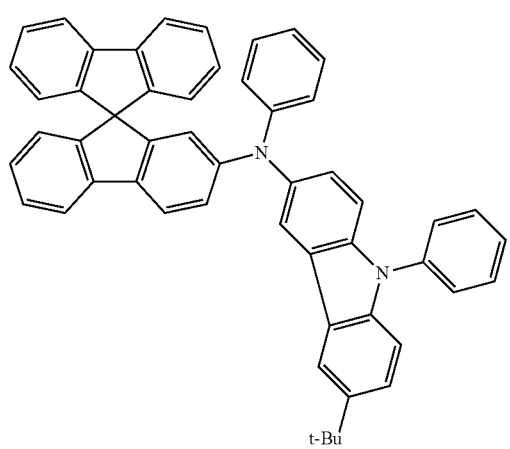
(53)
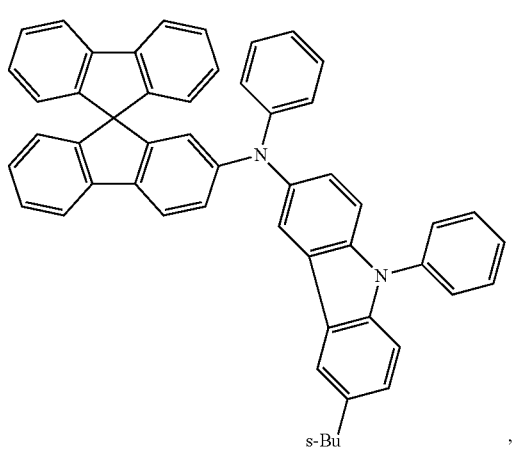
(51)
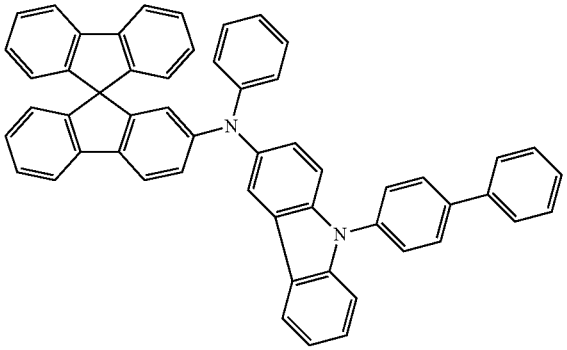
(54)

(55)
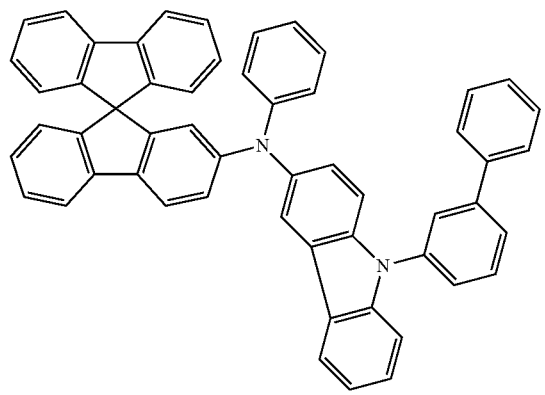
,
(56)
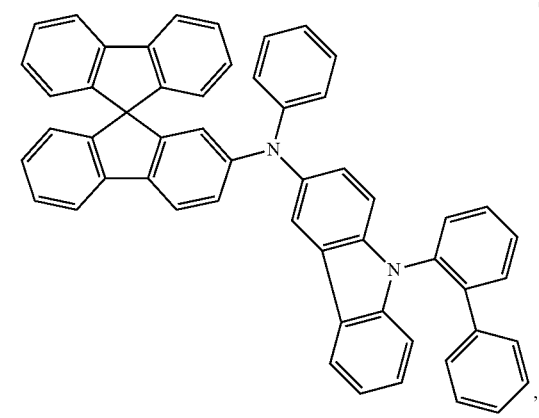
,
(57)
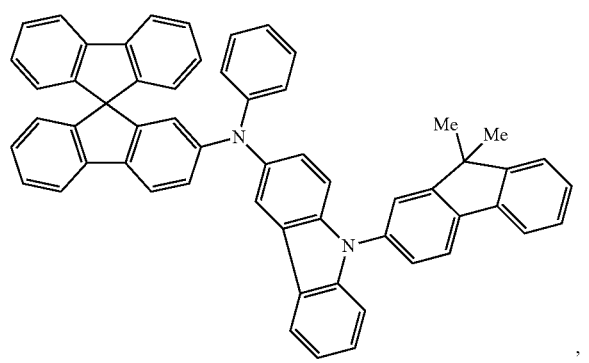
,
(58)
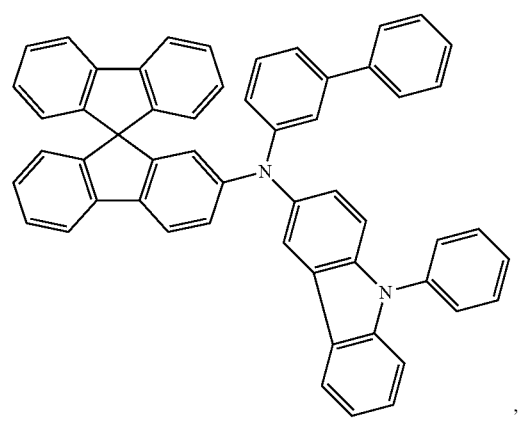
,
(59)
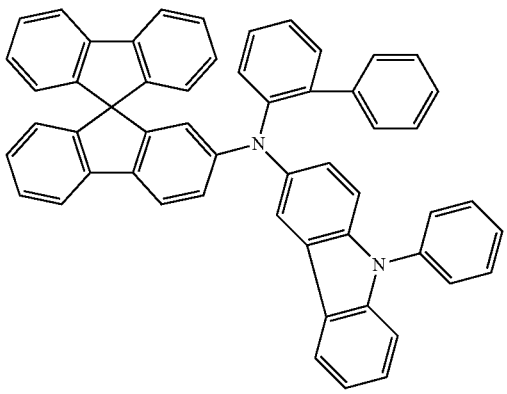
,
(60)
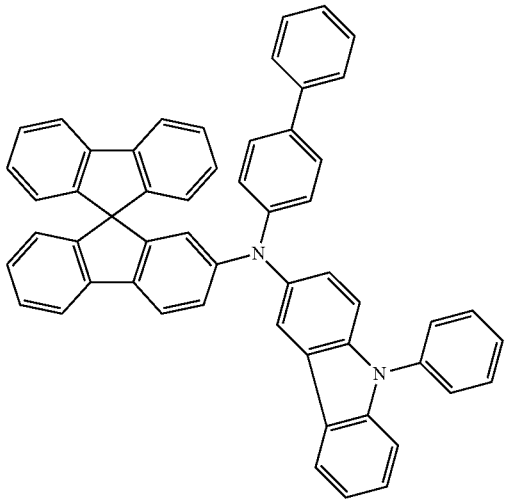
,
(61)
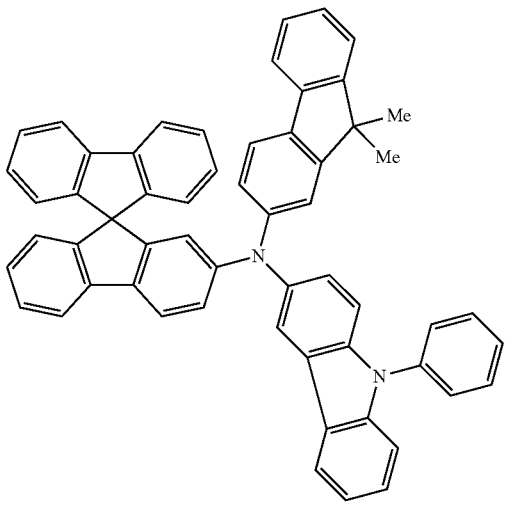
,

(62)
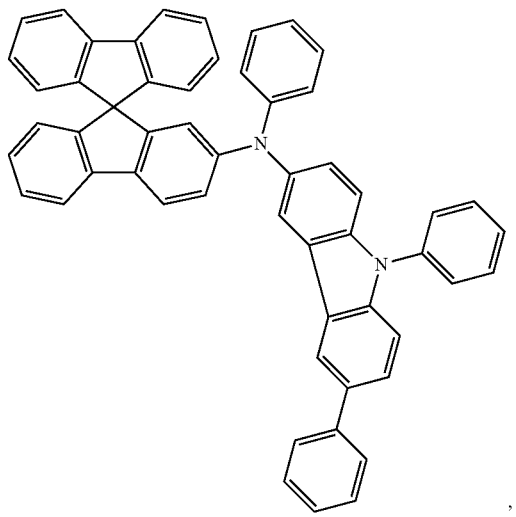
(64)
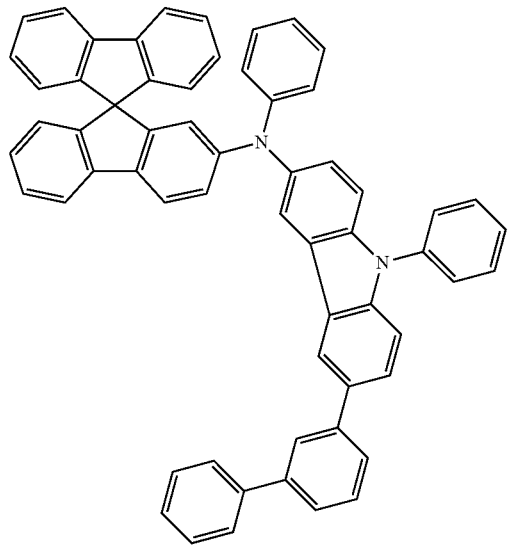
(65)
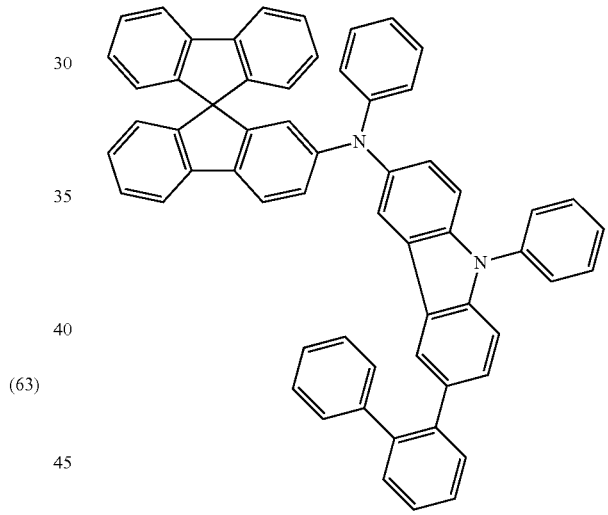
(63)
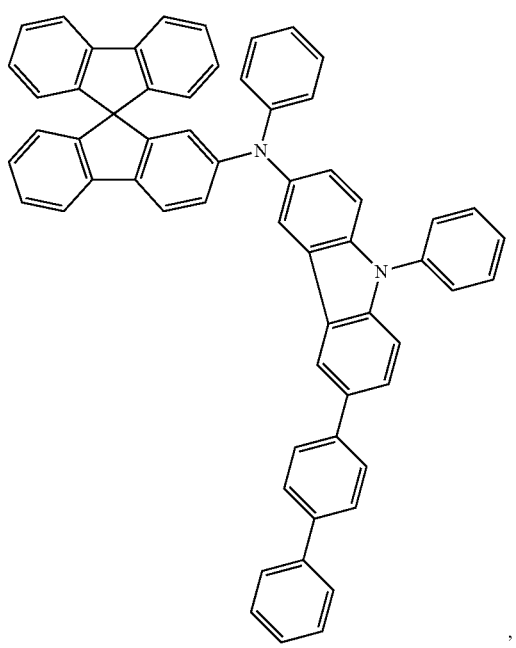
(66)
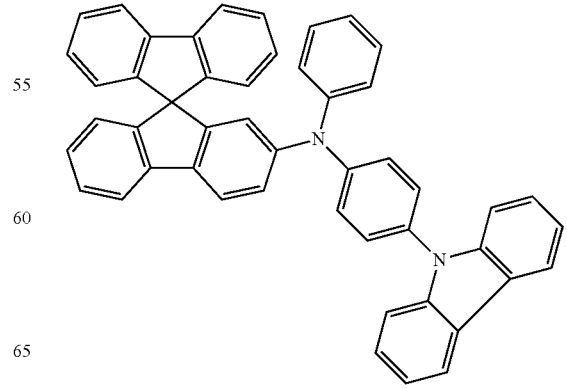

(67)
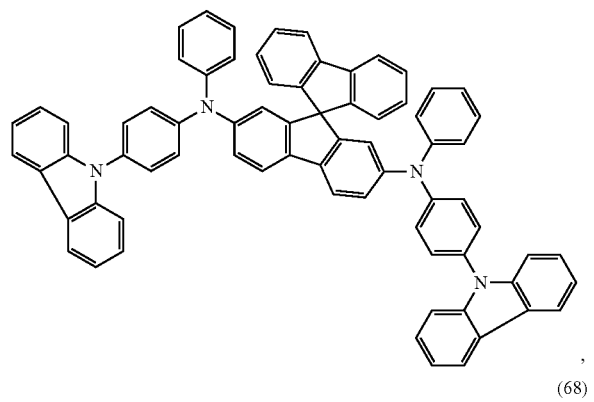
,
(68)
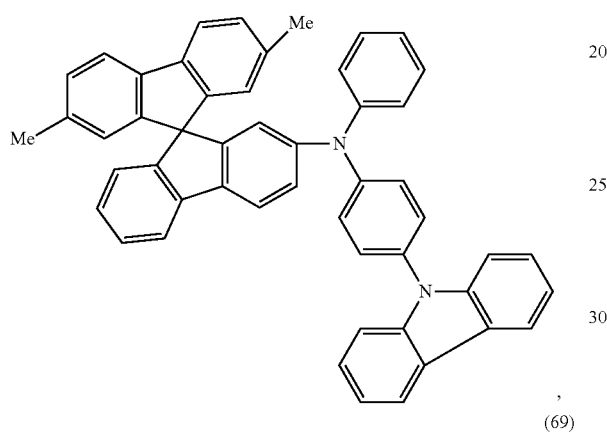
,
(69)
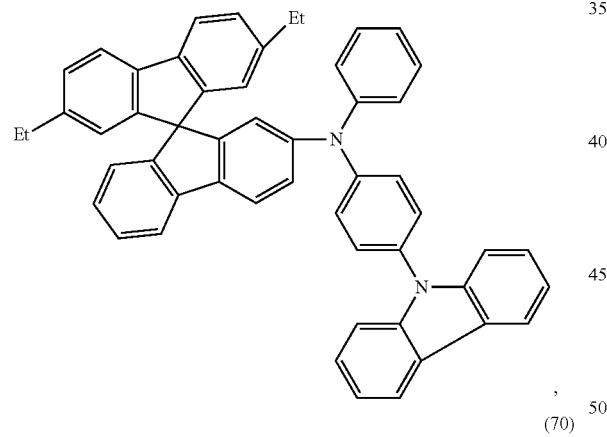
,
(70)
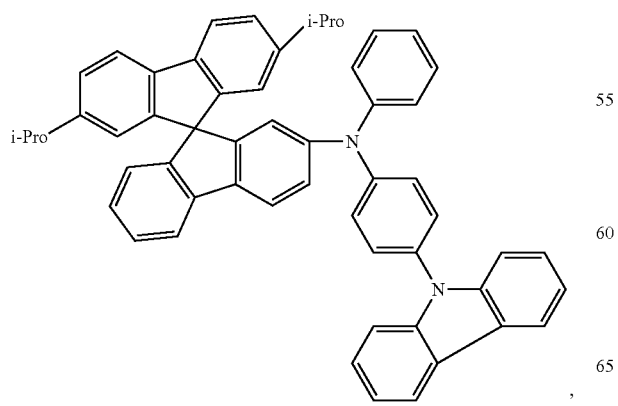
,
(71)
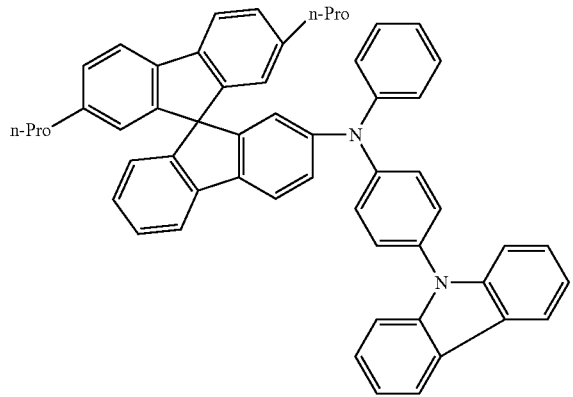
,
(72)
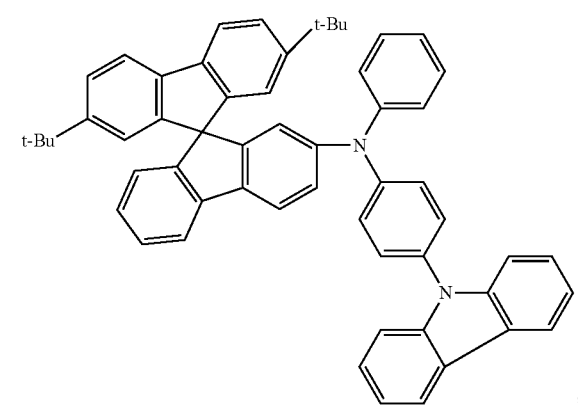
,
(73)
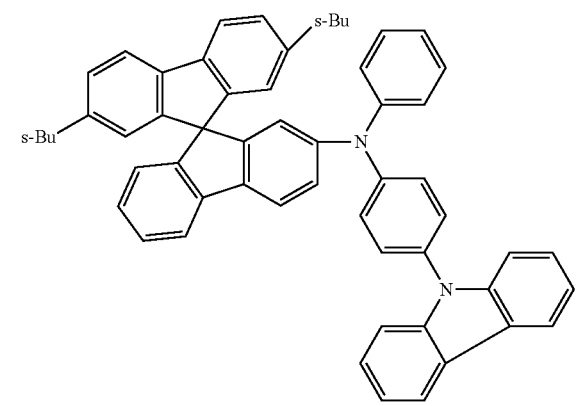
,

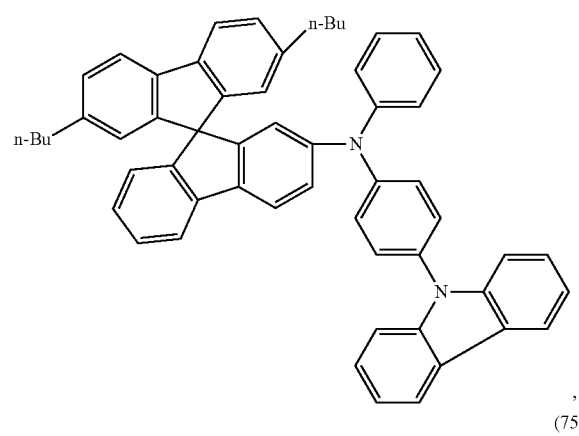
(74)
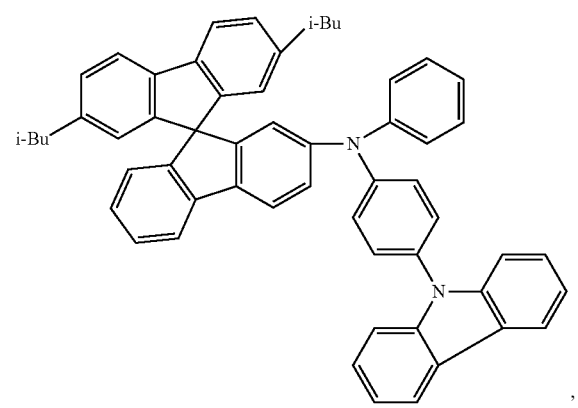
(75)
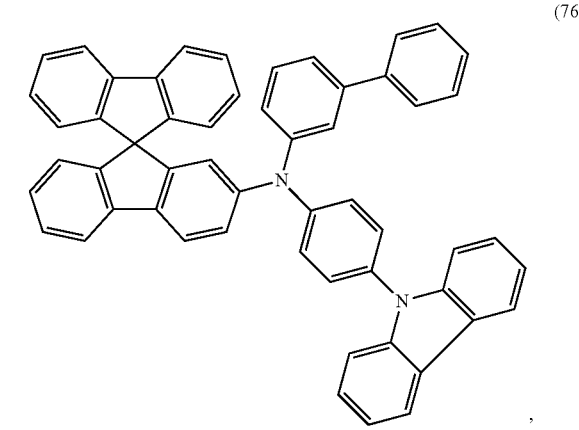
(76)
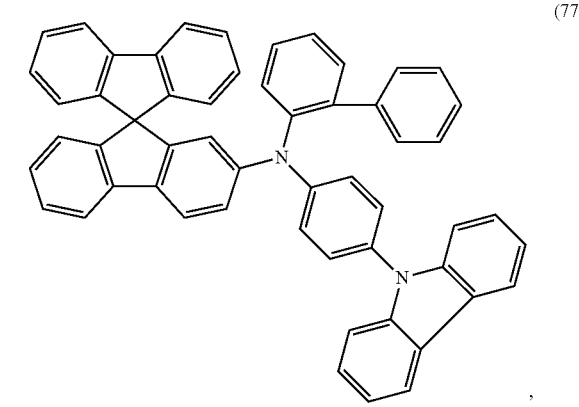
(77)
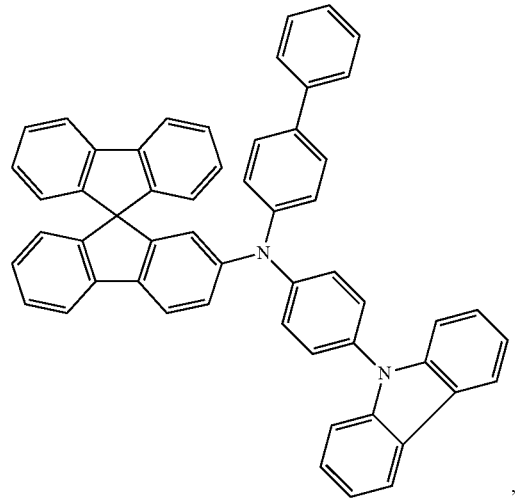
(78)
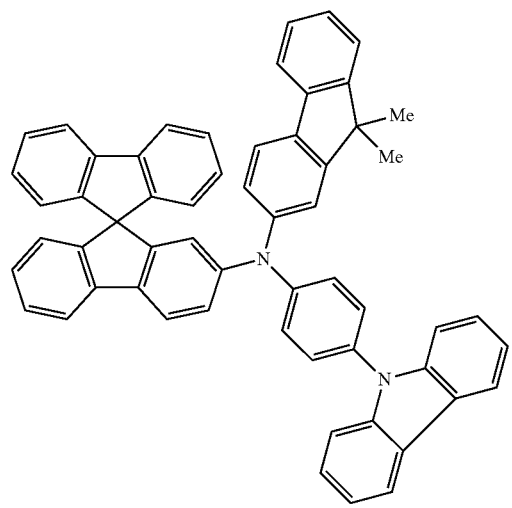
(79)
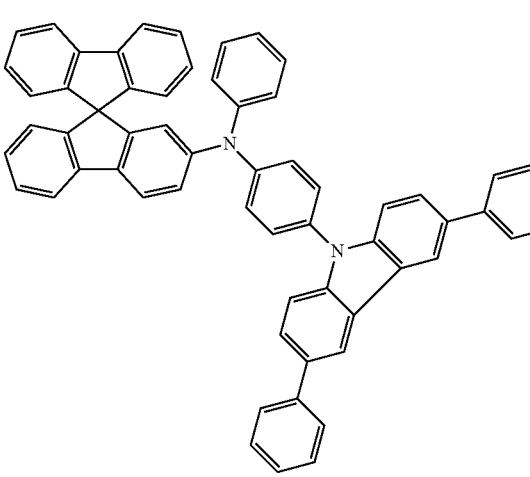
(80)

(81)
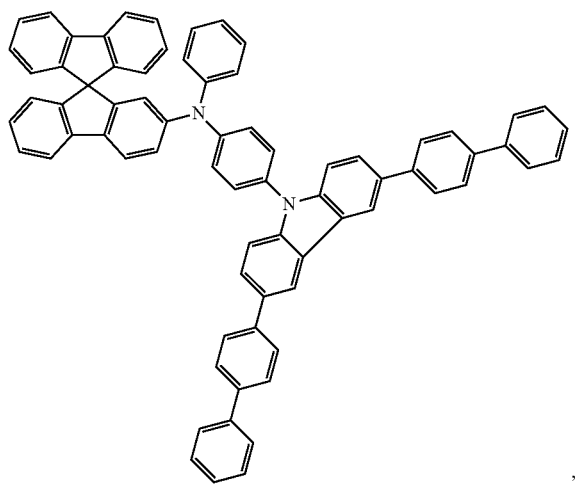
(82)
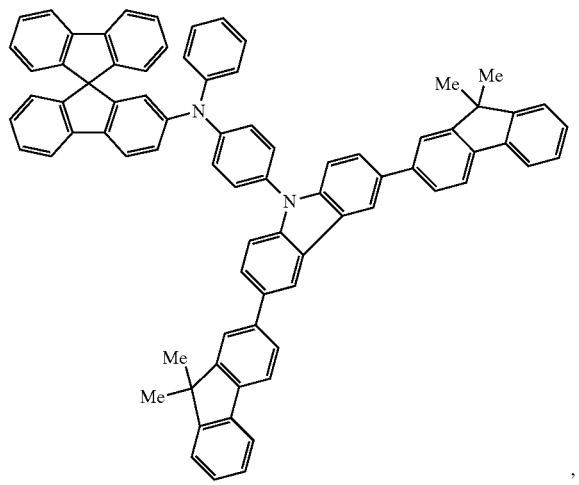
(83)
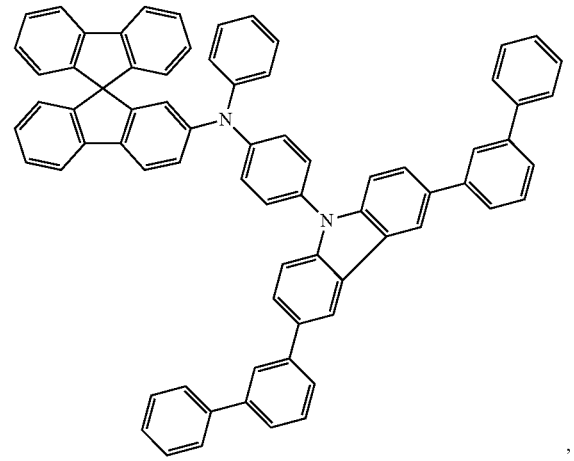
(84)
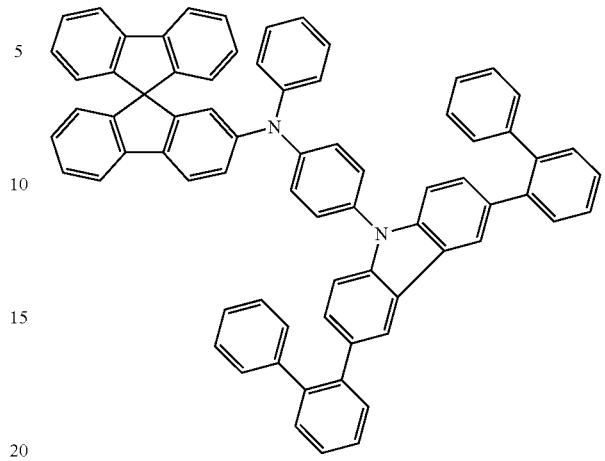
(85)
(86)
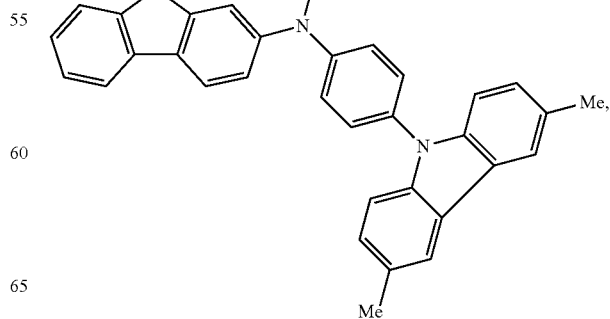

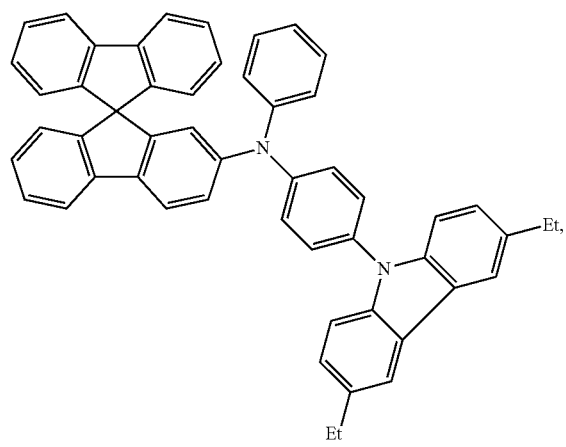
(87)
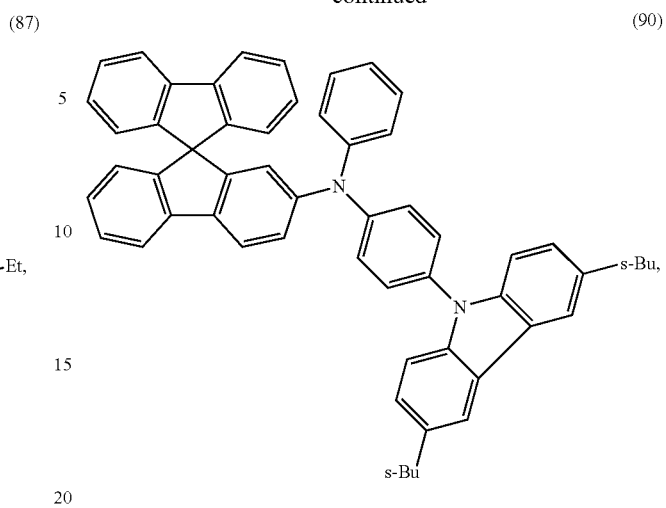
(90)
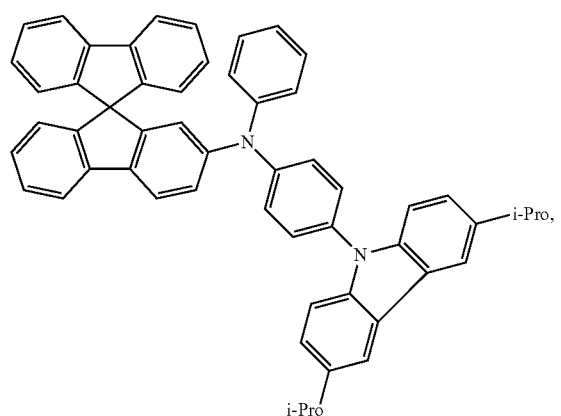
(88)
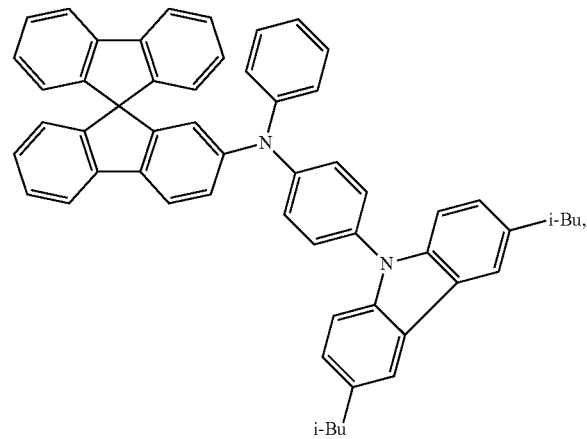
(91)
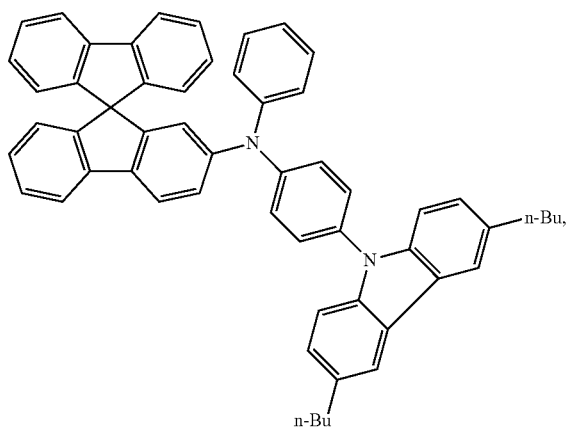
(89)
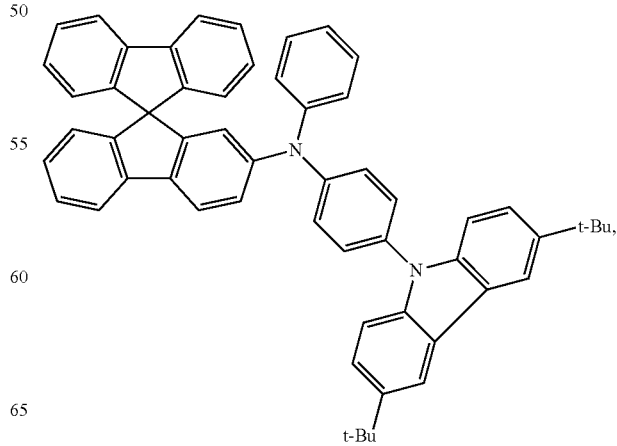
(92)

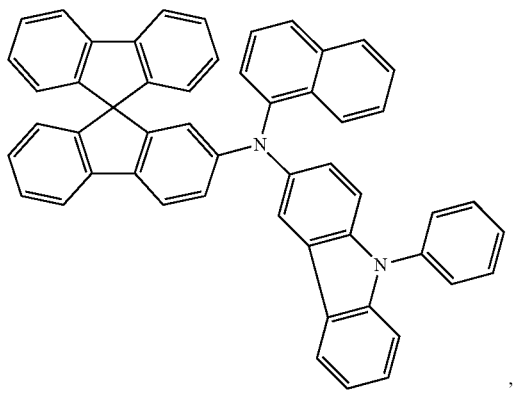
(93)
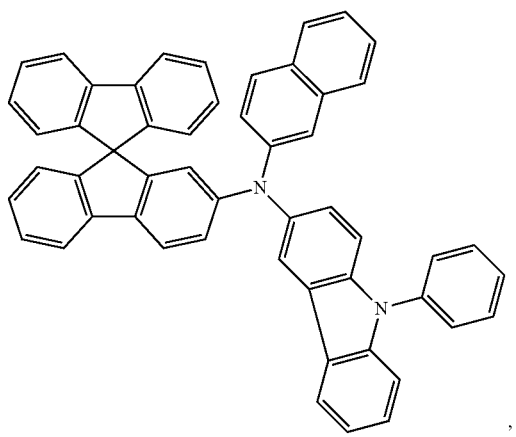
(94)
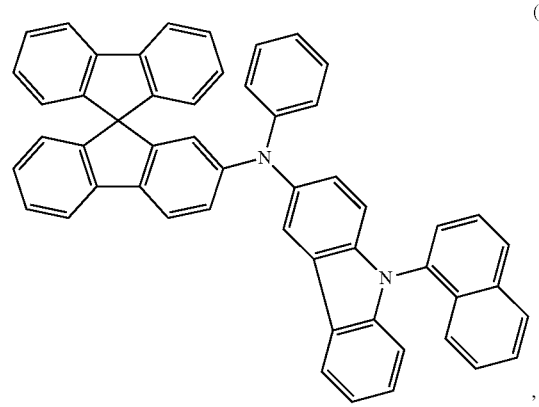
(95)
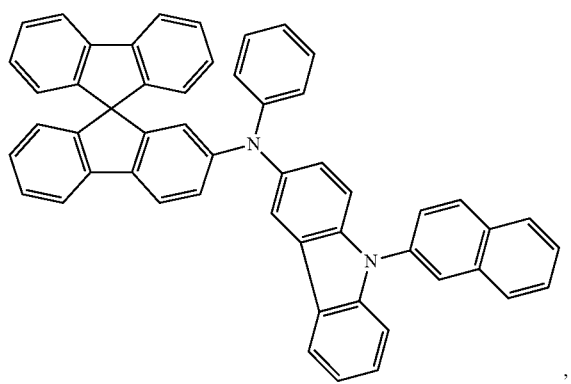
(96)
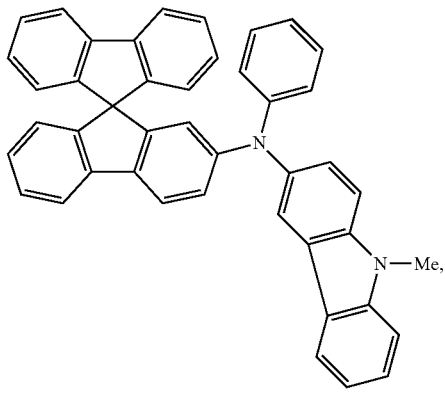
(97)
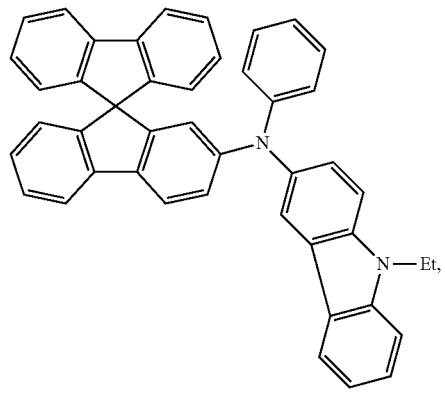
(98)
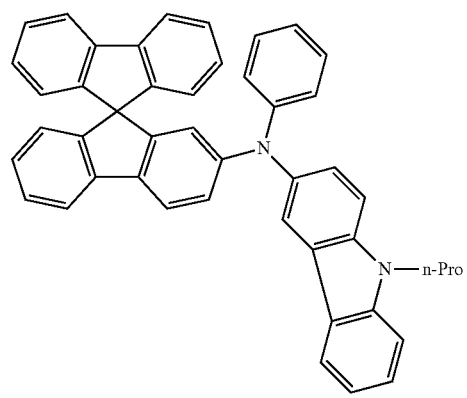
(99)
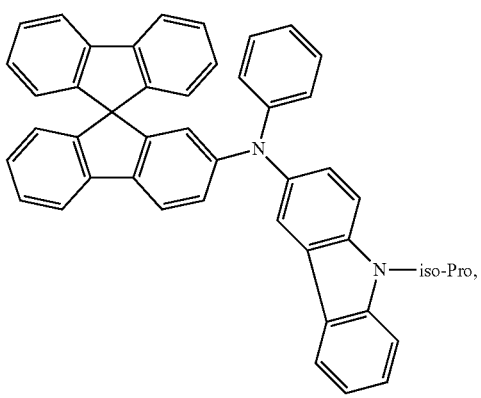
(100)

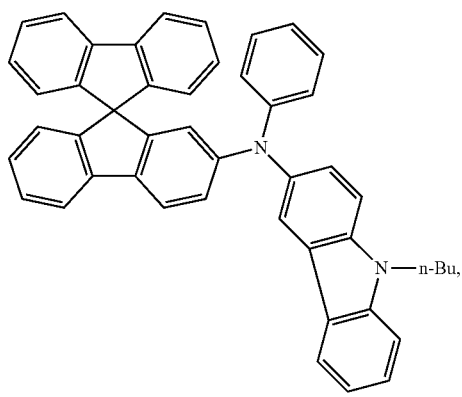
(101)
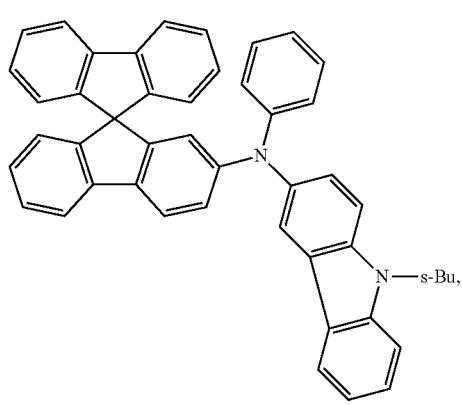
(102)
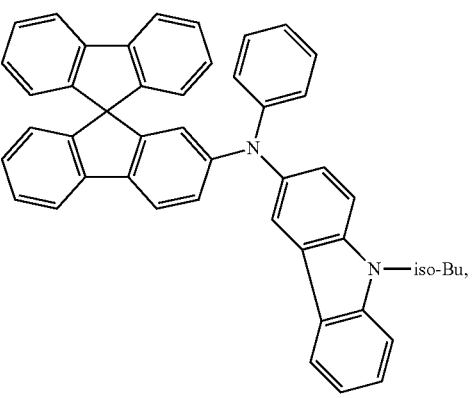
(103)
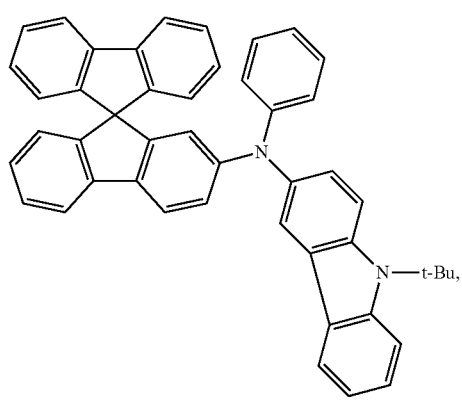
(104)
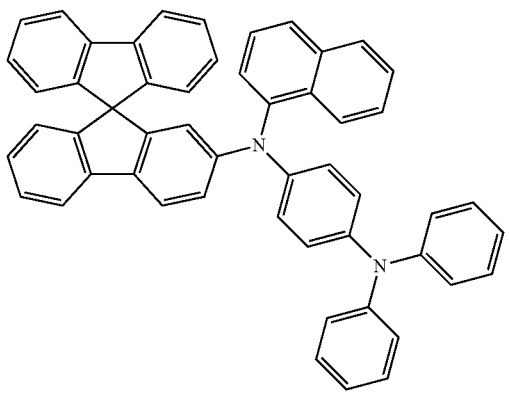
(105)
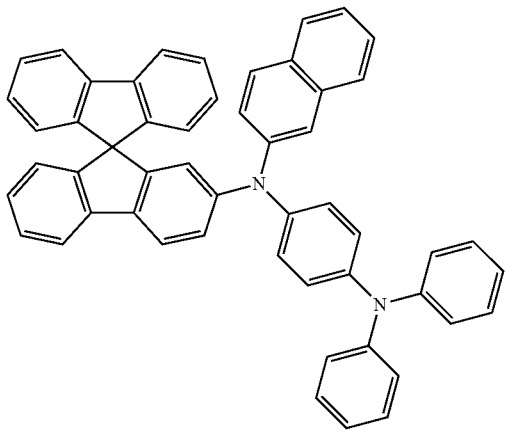
(106)
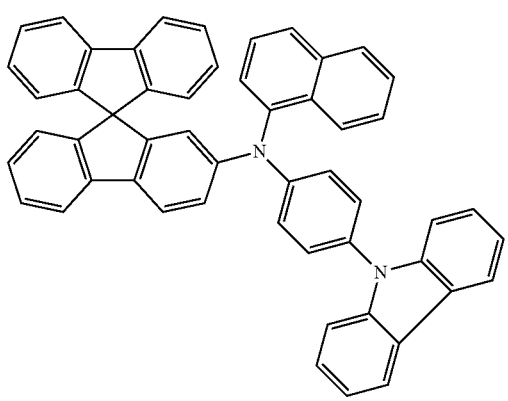
(107)

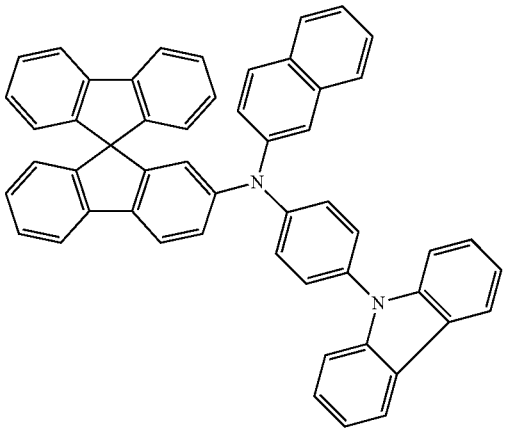

(108)

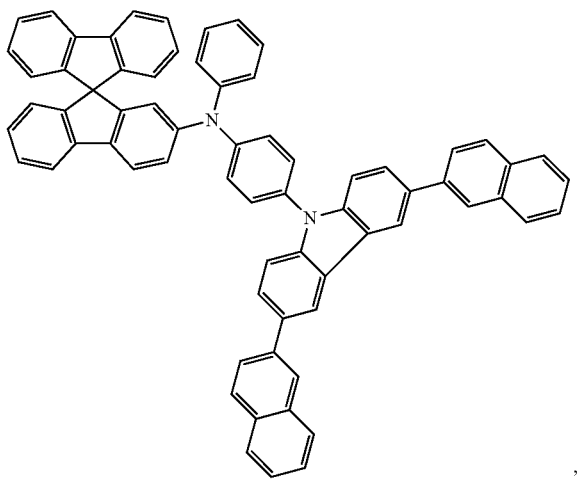

(109)

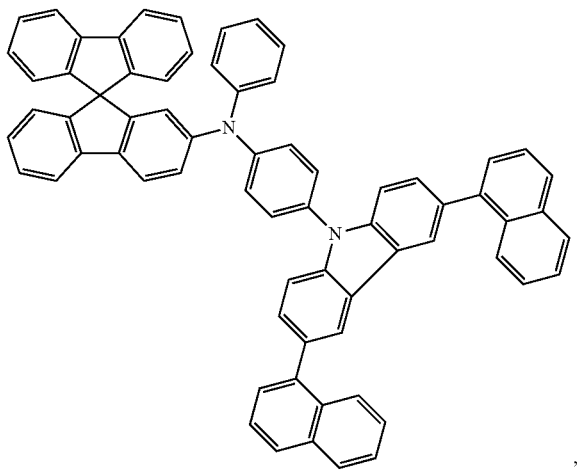

(110)

A spirofluorene derivative of the present invention having any of the above-described structures is a novel material having a high glass transition temperature (Tg). In addition, a spirofluorene derivative of the present invention having any of the above-described structures is a novel material having a wide energy gap. Further, a spirofluorene derivative of the present invention having any of the above-described structures is a novel material having a high Tg and a wide band gap.

Since a spirofluorene derivative of the present invention having any of the above-described structures has a low HOMO (Highest Occupied Molecular Orbital) level, it has' a sufficient hole transporting property capable of being used for a hole transporting layer of a light-emitting element in which a layer containing an organic compound is interposed between a pair of electrodes and which emits light by being applied with current. Accordingly, a spirofluorene derivative of the present invention having any of the above-described structures can be favorably used as a material for a light-emitting element.

In addition, since a spirofluorene derivative of the present invention having any of the above-described structures has a high LUMO (Lowest Unoccupied Molecular Orbital) level, it has a sufficient hole injecting property capable of being used for a hole injecting layer of a light-emitting element in which a layer containing an organic compound is interposed between a pair of electrodes and which emits light by being applied with current. Accordingly, a spirofluorene derivative of the present invention having any of the above-described structures can be favorably used as a material for a light-emitting element.

The spirofluorene derivatives described in Embodiment Mode 1 are electrochemically stable materials, since they have tolerance to a cycle of oxidation and reduction subsequent to the oxidation.

Embodiment Mode 2

Embodiment Mode 2 will describe a light-emitting element which uses a spirofluorene derivative described in Embodiment Mode 1.

A structure of a light-emitting element in the present invention is such that a layer containing an organic compound is interposed between a pair of electrodes. Note that the element structure is not particularly limited and can be selected as appropriate in accordance with its purposes.

FIG. 1 schematically shows an example of the element structure of a light-emitting element of the present invention. The light-emitting element shown in FIG. 1 has a structure where a layer containing an organic compound 102 is interposed between a first electrode 101 and a second electrode 103. The layer containing an organic compound 102 contains a compound into which a spirofluorene derivative described in Embodiment Mode 1 is introduced as a substituent. Note that an anode in the present invention refers to an electrode for injecting holes into a layer containing a light-emitting material. Note also that a cathode in the present invention refers to an electrode for injecting electrons into the layer containing a light-emitting material. Either of the first electrode 101 and the second electrode 103 serves as an anode, and the other serves as a cathode.

For the anode, a metal, an alloy, a conductive compound, a mixture thereof, or the like having a high work function (specifically, of 4.0 eV or higher) is preferably used. Specifically, indium tin oxide (hereinafter referred to as TO), indium tin oxide containing silicon, indium oxide containing zinc oxide (ZnO), or the like can be used. A film of these conductive metal oxides is generally formed by sputtering, but may be formed by a sol-gel method or the like. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (for example, titanium nitride (TIN)), or the like can be used.

On the other hand, for the cathode, a metal, an alloy, a conductive compound, a mixture thereof, or the like having a low work function (specifically, of 3.8 eV or lower) is preferably used. Specifically, a metal belonging to Group 1 or 2 of the periodic table, that is, an alkali metal such as lithium (Li) or cesium (Cs); an alkaline earth metal such as magnesium (Mg), calcium (Ca), or strontium (Sr); an alloy containing these (such as MgAg or AlLi); a rare-earth metal such as europium (Er) or ytterbium (Yb); an alloy containing these; or the like can be used. Note that when using an electron injecting layer having a high electron injecting property, the cathode can also be formed using a material having a high work function, that is, a material generally used for the anode. For example, the cathode can be formed of a metal such as Al or Ag or of a conductive inorganic compound such as ITO.

The layer containing an organic compound 102 can be formed using either a low molecular material or a high molecular material. In addition, the material forming the layer containing an organic compound 102 is not limited to a material containing only an organic compound material, and may partially contain an inorganic compound material. A layer containing an organic compound is generally formed by appropriately combining functional layers having respective functions such as a hole injecting layer, a hole transporting layer, a hole blocking layer, a light-emitting layer, an electron transporting layer, and an electron injecting layer; however, the layer containing an organic compound may include a layer having two or more functions of the above-described functional layers. In this embodiment mode, a layered structure including a hole injecting layer, a hole transporting layer, a light-emitting layer, an electron transporting layer, and an electron injecting layer is employed for the layer containing an organic compound.

In addition, the layer containing an organic compound 102 can be formed by either a wet method or a dry method, such as an evaporation method, an ink-jet method, a spin coating method, or a dip coating method.

The spirofluorene derivative described in Embodiment Mode 1 is a material having a high glass transition temperature (Tg) and high heat resistance. Since the layer containing an organic compound 102 of a light-emitting element of the present invention contains the spirofluorene derivative described in Embodiment Mode 1, the light-emitting element can have high heat resistance. In addition, since the spirofluorene derivative described in Embodiment Mode 1 has a wide energy gap, it is difficult for energy to transfer from another layer, and a light-emitting element having high light-emitting efficiency and color purity can be obtained. In a light emitting layer of a light-emitting element exhibiting blue light emission, since an energy gap of a host material in a light-emitting layer is slightly larger than that of blue light emitting material, energy transfer to a layer adjacent to the light-emitting layer has been a severe problem. However, since the spirofluorene derivative described in Embodiment Mode 1 has a wide energy gap, even in a blue light-emitting element, excitation energy transfer from a light-emitting layer is not a concern. The spirofluorene derivative described in Embodiment Mode 1 can also be favorably used for a light-emitting element emitting another color such as red or green.

Since the spirofluorene derivative described in Embodiment Mode 1 has a relatively low HOMO (Highest Occupied Molecular Orbital) level and a sufficient hole transporting property, it is suitable as a material for a hole transporting layer. In addition, since the spirofluorene derivative described in Embodiment Mode 1 has a sufficient hole transporting property and a wide energy gap, it can be particularly favorably used as a material for a hole transporting layer which is often formed adjacent to a light-emitting layer. Further, since the spirofluorene derivative described in Embodiment Mode 1 can be favorably used as a host material which disperses a light-emitting material in a light-emitting layer and has a wide band gap, it can be favorably used as a host material which disperses a blue light-emitting material having a relatively wide band gap. The spirofluorene derivative described in Embodiment Mode 1 can also be favorably used for a light-emitting element emitting another color such as red or green.

A light-emitting element of the present invention in this embodiment mode uses a spirofluorene derivative described in Embodiment Mode 1 for a hole transporting layer. There is no particular limitation on other functional layers in the layer containing an organic compound 102. In addition, since the spirofluorene derivative described in Embodiment Mode 1 has a high LUMO (Lowest Unoccupied Molecular Orbital) level, the passing-through of electrons can be prevented. Due to this, by using a spirofluorene derivative for a hole transporting layer which is in contact with a light-emitting layer, electrons and holes can efficiently be recombined in the light-emitting layer, which improves light-emitting efficiency.

The hole injecting layer can be formed using a metal oxide such as vanadium oxide, molybdenum oxide, ruthenium oxide, or aluminum oxide, or a mixture in which such a metal oxide is mixed with an appropriate organic compound. Alternatively, if using an organic compound, a porphyrin-based compound is effective, and phthalocyanine (abbrev.: H$_2$Pc), copper phthalocyanine (abbrev.: CuPc), or the like can be used. Further, a chemically-doped conductive high molecular compound can be used, such as polyethylene dioxythiophene (abbrev.: PEDOT) doped with polystyrene sulfonate (abbrev.: PSS), or polyaniline (abbrev.: PAni). The hole injecting layer is formed in contact with an anode. By using the hole injecting layer, a carrier injection barrier is reduced, and carriers are efficiently injected to a light-emitting layer, which results in reduction of driving voltage.

For the hole injecting layer, the spirofluorene derivative described in Embodiment Mode 1 can also be favorably used.

A composite material containing the spirofluorene derivative described in Embodiment Mode 1 and a metal oxide can be used for the hole injecting layer. As the metal oxide, an oxide of a transition metal is desirable, and oxide of a metal that belongs to any of Groups 4 to 8 of the periodic table is particularly desirable. Specifically, vanadium oxide, tantalum oxide, molybdenum oxide, tungsten oxide, rhenium oxide, and ruthenium oxide are preferable. In such composite materials, electrons are transferred between the spirofluorene derivative described in Embodiment Mode 1 and the metal oxide; accordingly, carrier density in the material is increased and beneficial effects such as an improvement in a hole injecting property can be obtained. Also, even when film thickness is increased, there is only a small increase in driving voltage. Even when a film thickness of this composite material is increased, the increase of driving voltage is small. Therefore, by adjusting the film thickness of a layer formed by using the composite material, a light-emitting element can be optically designed using a microcavity phenomenon or the like.

The hole transporting layer is formed using the spirofluorene derivative described in Embodiment Mode 1. The hole transporting layer is provided between the hole injecting layer and the light-emitting layer. Note that one hole transporting layer formed by using the spirofluorene derivative described in Embodiment Mode 1 may be formed such that the hole transporting layer has both functions of a hole injecting layer and a hole transporting layer. In this case, the hole injecting layer is not provided.

The light-emitting layer is formed using only a light-emitting material or using a host material into which a light-emitting material is dispersed. A substance which has favorable light-emitting efficiency and can emit light with a desired emission wavelength may be used as the light-emitting material. For example, in order to obtain red light emission, a substance which exhibits light emission having a peak of an emission spectrum at 600 nm to 680 nm can be used, such as 4-dicyanomethylene-2-isopropyl-6-[2-(1,1,7,7-tetramethyljulolidine-9-yl)ethenyl]-4H-pyran (abbrev.: DCJTI), 4-dicyanomethylene-2-methyl-6-[2-(1,1,7,7-tetramethyl-9-julolidine-9-yl)ethenyl]-4H-pyran (abbrev.: DCTI), 4-dicyanomethylene-2-tert-butyl-6-[2-(1,1,7,7-tetramethyljulolidine-9-yl)ethenyl]-4H-pyran (abbrev.: DCJTB), periflanthene, or 2,5-dicyano-1,4-bis[2-(10-methoxy-1,1,7,7-tetramethyljulolidine-9-yl)ethenyl]benzene. In order to obtain green light emission, a substance which exhibits light emission having a peak of an emission spectrum at 500 nm to 550 nm can be used, such as N,N'-dimethylquinacridon (abbrev.: DMQd), coumarin 6, coumarin 545T, or tris(8-quinolinolato)aluminum (abbrev.: Alq$_3$). In order to obtain blue light emission, a substance which exhibits light emission having a peak of an emission spectrum at 420 nm to 500 nm can be used, such as 9,10-bis(2-naphthyl)-tert-butylanthracene (abbrev.: t-BuDNA), 9,9'-bianthryl, 9,10-diphenylanthracene (abbrev.: DPA), 9,10-bis(2-naphthyl)anthracene (abbrev.: DNA), bis(2-methyl-8-quinolinolato)-4-phenylphenolato-gallium (abbrev.: BGaq), or bis(2-methyl-8-quinolinolato)-4-phenylphenolato-aluminum (abbrev.: BAlq). In addition to the material which generates fluorescence as described above, a material which generates phosphorescence can also be used as a light-emitting material, such as bis[2-(3,5-bis(trifluoromethyl)phenyl)pyridinato-N,C$^{2'}$]iridium(III)picolinate (abbrev.: Ir(CF$_3$ppy)$_2$(pic)), bis[2-(4,6-difluorophenyl)pyridinato-N,C$^{2'}$]iridium(III)acetylacetonate (abbrev.: FIr(acac)), bis[2-(4,6-difluorophenyl)pyridinato-N,C$^2$]iridium(III)picolinate (FIr(pic)), or tris(2-phenylpyridinato-N,C$^2$ iridium (abbrev.: Ir(ppy)$_3$). In addition, as the host material, an anthracene derivative such as 9,10-di(2-naphthyl)-2-tert-butylanthracene (abbrev.: t-BuDNA), a carbazole derivative such as 4,4'-di(N-carbazolyl)biphenyl (abbrev.: CBP), a metal complex such as bis[2-(2-hydroxyphenyl)pyridinato] zinc (abbrev.: Znpp$_2$) or bis[2-(2-hydroxyphenyl)benzoxazolato]zinc (abbrev.: ZnBOX), or the like can be used. In the case where the light-emitting layer is formed using the host material into which the light-emitting material is dispersed, the light-emitting layer can be formed by adding the light-emitting material to the host material in a proportion of 0.001 wt % to 50 wt %, preferably, 0.03 wt % to 20 wt %. Note that in this case, it is preferable to combine materials such that an energy gap of the host material is larger than that of the light-emitting material.

In the case where the electron transporting layer is used, it is provided between the light-emitting layer and the electron injecting layer. An appropriate material is a typical metal complex such as tris(8-quinolinolato)aluminum (abbrev.: Alq$_3$), tris(4-methyl-8-quinolinolato)aluminum (abbrev.: Almq$_3$), bis(10-hydroxybenzo[h]-quinolinato)beryllium (abbrev.: BeBq$_2$), bis(2-methyl-8-quinolinolato)-(4-hydroxy-biphenylyl)-aluminum (abbrev.: BAlq), bis[2-(2-hydroxyphenyl)-benzoxazolato]zinc (abbrev.: Zn(BOX)$_2$), or bis[2-(2-hydroxyphenyl)-benzothiazolato]zinc (abbrev.: Zn(BTZ)$_2$). Alternatively, a hydrocarbon-based compound such as 9,10-diphenylanthracene or 4,4'-bis(2,2-diphenylethenyl)biphenyl, or the like is preferable. Further alternatively, a triazole derivative such as 3-(4-tert-butylphenyl)-4-(4-ethylphenyl)-5-(4-biphenylyl)-1,2,4-triazole or a phenanthroline derivative such as bathophenanthroline or bathocuproin may be used.

There is no particular limitation on what electron injecting material is used for forming the electron injecting layer. Specifically, an alkali metal salt such as lithium fluoride, lithium oxide, or lithium chloride, an alkaline earth metal salt such as calcium fluoride, or the like is preferable. Alternatively, a layer in which a donor compound such as lithium is added to a so-called electron transporting material such as tris(8-quinolinolato)aluminum (abbrev.: Alq$_3$) or bathocuproin (abbrev.: BCP) can be used. The electron injecting layer is formed in contact with the cathode. By using the electron injecting layer, a carrier injection barrier is reduced, and carriers are efficiently injected to a light-emitting layer, which results in reduction of driving voltage.

In the case where the spirofluorene derivative described in Embodiment Mode 1 is used as a host material of the hole injecting layer or the light-emitting layer and another material is used for forming the hole transporting layer, there is no particular limitation on what material is used for the hole transporting layer, and 4,4'-bis[N-(1-naphthyl)-N-phenylamino]biphenyl (abbrev.: NPB), 4,4'-bis[N-(3-methylphenyl)-N-phenylamino]biphenyl (abbrev.: TPD), 4,4',4"-tris(N,N-diphenylamino)triphenylamine (abbrev.: TDATA), 4,4',4"-tris[N-(3-methylphenyl)-N-phenylamino]triphenylamine (abbrev.: MTDATA), 4,4'-bis{N-[4-(N,N-di-m-tol-phenyo)phenyl]-N-phenylamino}biphenyl (abbrev.: DNTPD), 1,3,5-tris[N,N-di(m-tolyl)amino]benzene (abbrev.: m-MTDAB), 4,4',4"-tris(N-carbazolyl)triphenylamine (abbrev.: TCTA), phthalocyanine (abbrev.: H$_2$Pc), copper phthalocyanine (abbrev.: CuPc), vanadyl phthalocyanine (abbrev.: VOPc), or the like can be used. The hole transporting layer may be formed by combining two or more layers of layers using the above-described materials or may be a layer having a multilayer structure in which a layer containing the spirofluorene derivative described in Embodiment Mode 1 and a layer using the above-described material are combined.

Although this embodiment describes a structure of a light-emitting element which provides light emission only from the light-emitting layer, a light-emitting element may be designed so as to provide light emission from not only a light-emitting layer but also another layer such as an electron transporting layer or a hole transporting layer. For example, light emission can be obtained from not only a light-emitting layer but also a transporting layer by adding a dopant which contributes to light emission to an electron transporting layer or a hole transporting layer. When light-emitting materials used for a light-emitting layer and a transporting layer have different light emission colors, a spectrum with emission colors thereof overlapped with each other can be obtained. If emission colors of the light-emitting layer and the transporting layer have the relationship of complementary colors, white light emission can be obtained.

Note that a light-emitting element of this embodiment mode has many variations obtained by changing a material for the first electrode 101 and a material for the second electrode 103 of FIG. 1. When a light transmitting material is used for the first electrode 101, light can be emitted from the first electrode 101 side. When a light blocking (particularly, a reflective) material is used for the first electrode 101 and a light transmitting material is used for the second electrode 103, light can be emitted from the second electrode 103 side. Furthermore, when a light transmitting material is used for both the first electrode 101 and the second electrode 103, light can be emitted from both the first electrode 101 side and the second electrode 103 side.

Embodiment Mode 3

A light-emitting device of the present invention and a method for manufacturing thereof will be described in this embodiment mode, with reference to FIGS. 2A to 2E and 3A to 3C. Note that an example of manufacturing an active matrix light-emitting device will be described in this embodiment mode; however, the present invention may of course also be applied to a passive matrix light-emitting device.

Figure 2A:
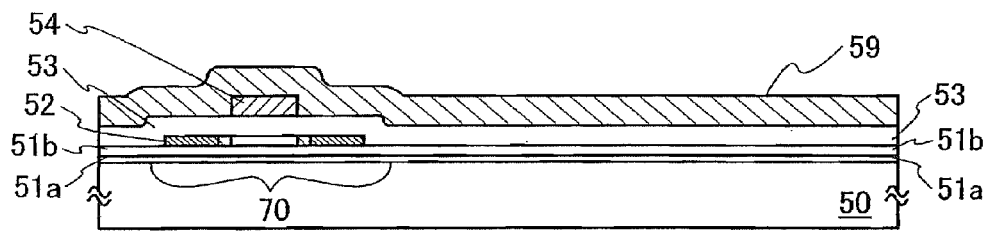
FIGS. 2A to 2E are cross sectional views showing a manufacturing method of an active matrix light-emitting device of the present invention.

First, a first base insulating layer 51a and a second base insulating layer 51b are formed over a substrate 50. Then, a semiconductor layer 52 is formed over the second base insulating layer 51b (FIG. 2A).

As a material for the substrate 50, glass, quartz, plastic (such as polyimide, acrylic, polyethylene terephthalate, polycarbonate, polyacrylate, or polyether sulfone), or the like can be used. A substrate made from such a material may be used after being polished with CMP or the like, if necessary. In this embodiment mode, a glass substrate is used.

Providing the first base insulating layer 51a and the second base insulating layer 51b can prevent an element in the substrate 50 which adversely affects a characteristic of a semiconductor film, such as an alkali metal or an alkaline earth metal, from diffusing into the semiconductor layer. As materials for the first base insulating layer 51a and the second base insulating layer 51b, silicon oxide, silicon nitride, silicon oxide containing nitrogen, silicon nitride containing oxygen, or the like can be used. In this embodiment mode, the first base insulating layer 51a is formed using silicon nitride and the second base insulating layer 51b is formed using silicon oxide. Although a base insulating film is formed using the first base insulating layer 51a and the second base insulating layer 51b in this embodiment mode, the base insulating film may be formed using a single layer or two or more layers. Further, when diffusion of an impurity from the substrate does not cause a problem, it is not necessary to provide a base insulating film.

In this embodiment mode, the semiconductor layer formed after the formation of the first and the second base insulating layers is obtained by crystallizing an amorphous silicon film by irradiation with a laser beam. Specifically, an amorphous silicon film is formed over the second base insulating layer 51b to have a thickness of 25 to 100 nm (preferably, 30 to 60 nm). As a method for forming the amorphous silicon film, a method such as sputtering, reduced pressure CVD, or plasma CVD can be used. Then, heat treatment is conducted at 500° C. for 1 hour to dehydrogenate the film.

Next, the amorphous silicon film is crystallized by using a laser irradiation apparatus to form a crystalline silicon film. In the laser crystallization of this embodiment mode, an excimer laser is used, and a laser beam oscillated from the excimer laser is processed into a linear beam spot using an optical system. Then, the amorphous silicon film is irradiated with the linear beam spot so as to obtain the crystalline silicon film. This crystalline silicon film is used as a semiconductor layer. Note that the amorphous silicon film may also be used as is as a semiconductor layer.

Other methods of crystallizing an amorphous silicon film include a crystallization method using only heat treatment, and a crystallization method performing heat treatment by using a catalytic element for accelerating crystallization. As an element for accelerating crystallization, nickel, iron, palladium, tin, lead, cobalt, platinum, copper, gold, and the like can be given as examples. Compared to a case where crystallization is performed by only heat treatment, when crystallization is performed using this kind of element for accelerating crystallization, crystallization is performed at a lower temperature for a shorter time, so damage to the glass substrate and the like is small. When crystallization is performed by heat treatment only, a quartz substrate or the like which is resistant to heat may be used as the substrate 50.

Next, in order to control a threshold value, a minute amount of an impurity is added to the semiconductor layer, if necessary. That is, channel doping is performed. To obtain a required threshold value, an impurity (such as phosphorous or boron) having an N-type conductivity or a P-type conductivity is added to the semiconductor layer by ion doping or the like.

Then, the semiconductor layer is patterned into a prescribed shape, as shown in FIG. 2A, to obtain an island-like semiconductor layer 52. The patterning is performed by applying a photoresist to the semiconductor layer, exposing a predetermined mask shape, baking the shaped photoresist to form a resist mask over the semiconductor layer, and etching the semiconductor layer using the resist mask.

Next, a gate insulating layer 53 is formed to cover the semiconductor layer 52. The gate insulating layer 53 is formed by plasma CVD or sputtering to have a thickness of 40 to 150 nm using an insulating layer containing silicon. In this embodiment mode, the gate insulating layer 53 is formed using silicon oxide.

Next, a gate electrode 54 is formed over the gate insulating layer 53. The gate electrode 54 is formed using an element selected from among tantalum, tungsten, titanium, molybdenum, aluminum, copper, chromium, and niobium; or using an alloy material or a compound material containing the element as its main component. Further, a semiconductor film typified by a polycrystalline silicon film doped with an impurity element such as phosphorous may be used, or an AgPdCu alloy may be used.

Although the gate electrode 54 is formed with a single layer in this embodiment mode, it may be formed to have a laminated structure including two or more layers, such as a lower layer made from tungsten and an upper layer made from molybdenum. When the gate electrode is formed to include a laminated structure, the above-mentioned materials may be used. Further, a combination of the above-mentioned materials may be selected as appropriate. The gate electrode 54 is processed by being etched using a mask made from a photoresist.

Next, a high concentration impurity is added to the semiconductor layer 52 while using the gate electrode 54 as a mask. Thus, a thin film transistor 70 including the semiconductor layer 52, the gate insulating layer 53, and the gate electrode 54 is formed.

Note that there is no particular limitation on the process of manufacturing the thin film transistor, and it may be changed as appropriate to obtain a thin film transistor with a desired structure.

For a pixel portion, a top-gate type thin film transistor using the crystalline silicon film which is crystallized by using laser crystallization is used in this embodiment mode; however, it is also possible to use a bottom-gate type thin film transistor using an amorphous semiconductor film. For the amorphous semiconductor film, not only silicon but also silicon germanium can be used. In the case of using silicon germanium, the concentration of germanium is preferably set to be about 0.01 to 4.5 atomic %.

Next, an insulating film (a hydrogenation film) 59 is formed using silicon nitride so as to cover the gate electrode 54 and the gate insulating layer 53. After formation, the insulating film (hydrogenation film) 59 is heated at 480° C. for about 1 hour to activate the impurity element and hydrogenate the semiconductor layer 52.

Figure 2B:
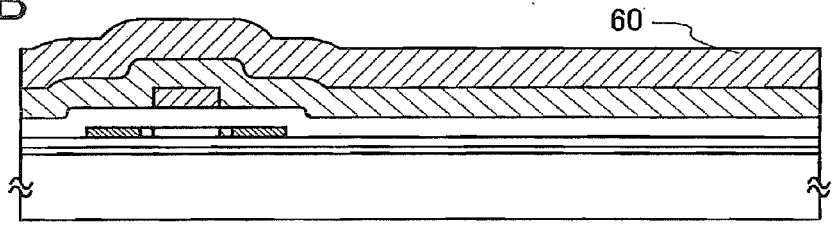

Next, a first interlayer insulating layer 60 which covers the insulating film (hydrogenation film) 59 is formed. As a material for forming the first interlayer insulating layer 60, silicon oxide, acrylic, polyimide, siloxane, a low-k material, or the like may be used. In this embodiment mode, a silicon oxide film is formed as the first interlayer insulating layer (FIG. 2B).

Figure 2C:
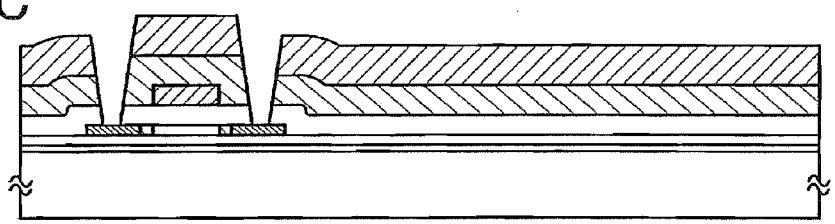

Next, contact holes that reach the semiconductor layer 52 are formed. The contact holes can be formed by etching using a resist mask until the semiconductor layer 52 is exposed. The contact holes can be formed by either wet etching or dry etching. Further, they may be formed by etching one or more times, depending on conditions. When etching is performed a plurality of times, both wet etching and dry etching may be used (FIG. 2C).

Figure 2D:
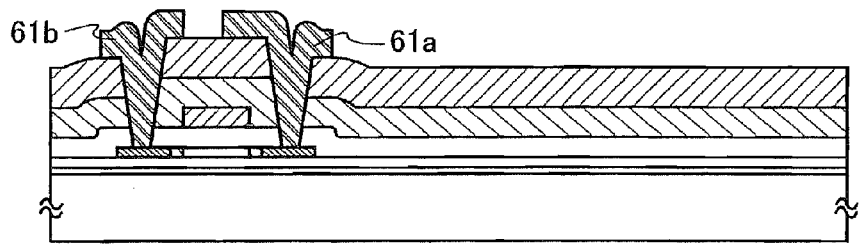

A conductive layer is then formed so as to cover the contact holes and the first interlayer insulating layer 60. This conductive layer is processed into a desired shape to form a connection portion 61a, a wire 61b, and the like. This wire may have a single layer made from aluminum, copper, an aluminum-carbon-nickel alloy, an aluminum-carbon-molybdenum alloy, or the like. Further, the wire may have a structure formed by stacking molybdenum, aluminum, and molybdenum layers from the substrate side, a structure formed by stacking titanium, aluminum, and titanium layers from the substrate side, or a structure formed by stacking titanium, titanium nitride, aluminum, and titanium layers from the substrate side (FIG. 2D).

Figure 2E:
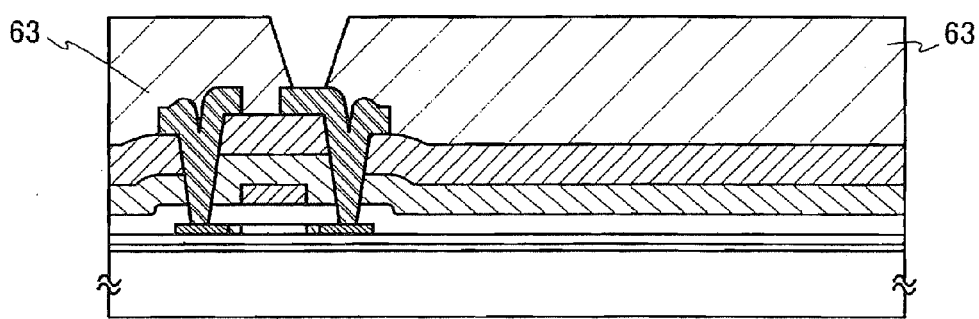

Then, a second interlayer insulating layer 63 is formed to cover the connection portion 61a, the wire 61b, and the first interlayer insulating layer 60. As a material of the second interlayer insulating layer 63, a coating film having a self-planarizing property such as acrylic, polyimide, or siloxane is preferably used. In this embodiment mode, siloxane is used to form the second interlayer insulating layer 63 (FIG. 2E).

Next, an insulating layer may be formed using silicon nitride or the like over the second interlayer insulating layer 63. This insulating layer is formed to prevent the second interlayer insulating layer 63 from being etched more than necessary in a subsequent etching of a pixel electrode. Therefore, when the ratio of the etching rate of the pixel electrode to the etching rate of the second interlayer insulating layer is large, this insulating layer does not have to be provided. Next, a contact hole is formed through the second interlayer insulating layer 63 to reach the connection portion 61a.

Then, a conductive layer is formed to cover the contact hole and the second interlayer insulating layer 63 (or the insulating layer). The conductive layer is then processed to form a first electrode 64 of a thin-film light-emitting element. The first electrode 64 is electrically in contact with the connection portion 61a.

The first electrode 64 can be formed with a conductive film, using a metal having a conductive property, such as aluminum (Al), silver (Ag), gold (Au), platinum (Pt), nickel (Ni), tungsten (W), chromium (Cr), molybdenum (Mo), iron (Fe), cobalt (Co), copper (Cu), palladium (Pd), lithium (Li), cesium (Cs), magnesium (Mg), calcium (Ca), strontium (Sr), or titanium (Ti); or an alloy such as an aluminum-silicon (Al—Si) alloy, an aluminum-titanium (Al—Ti) alloy, or an aluminum-silicon-copper (Al—Si—Cu) alloy; or a metal compound, such as a nitride such as titanium nitride (TIN), indium tin oxide (ITO), indium tin oxide containing silicon oxide (ITSO), or indium zinc oxide (IZO) in which zinc oxide (ZnO) is mixed in indium oxide at 2 to 20 wt %; or the like.

Figure 3A:
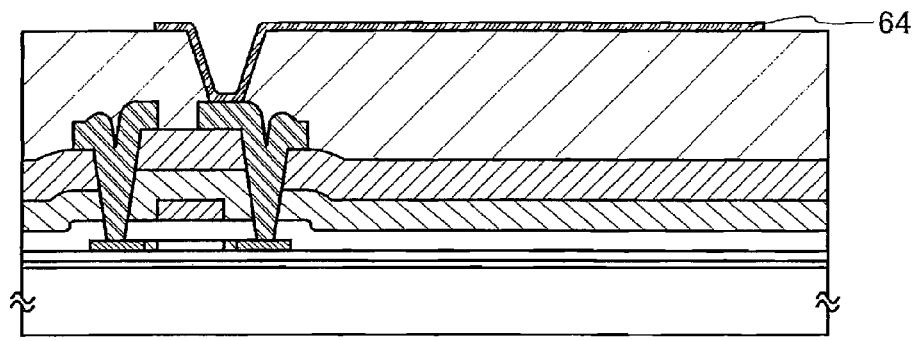
FIGS. 3A to 3C are cross sectional views showing a manufacturing method of an active matrix light-emitting device of the present invention.

An electrode through which light is emitted may be formed using a conductive film having a light transmitting property. For example, a metal compound such as ITO, ITSO, and IZO can be used, or an extremely thin film of a metal such as Al or Ag can be used. Further, in the case where light is emitted through a second electrode, the first electrode can be formed using a material having high reflectance (such as Al or Ag). In this embodiment mode, ITSO is used to form the first electrode 64 (FIG. 3A).

Figure 3B:
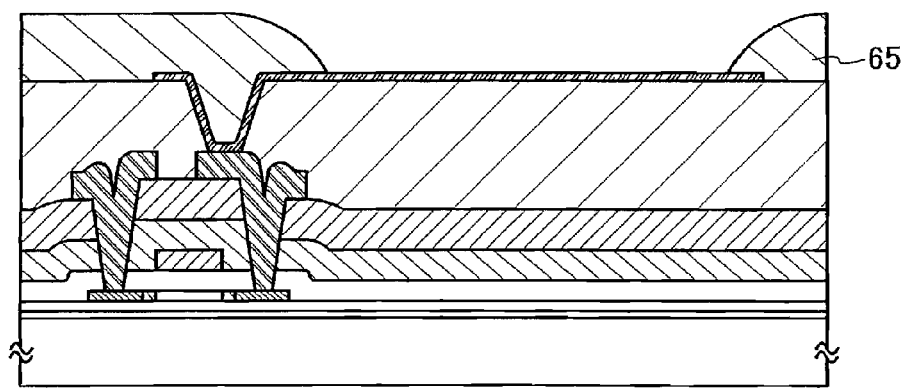
Figure 3C:
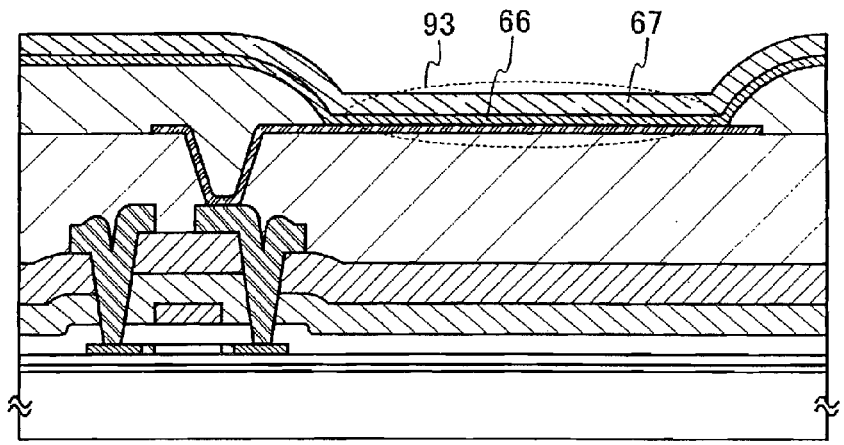

Next, an insulating layer is formed using an organic material or an inorganic material to cover the second interlayer insulating layer 63 (or the insulating layer) and the first electrode 64. Then, the insulating layer is processed to expose a part of the first electrode 64, so as to form a partition wall 65. A photosensitive organic material (such as acrylic or polyimide) is preferably used as a material of the partition wall 65; however, the partition wall 65 may also be formed using a non-photosensitive organic or inorganic material. Further, a black pigment or dye such as titanium black or carbon nitride may be dispersed in a material of the partition wall 65 by using a dispersant, to blacken the partition wall 65 so that the partition wall 65 may be used as a black matrix. Preferably, an edge of the partition wall 65 which faces the first electrode has a curvature, and has a tapered shape in which the curvature continuously changes (FIG. 3B).

Next, a layer containing an organic compound 66 is formed. A second electrode 67 is then formed to cover the layer containing an organic compound 66. Thus, a light-emitting element 93 including a layer containing an organic compound 66 between the first electrode 64 and the second electrode 67 can be formed. By applying higher voltage to the first electrode than to the second electrode, light emission can be obtained. As an electrode material used for forming the second electrode 67, the similar materials as for the first electrode can be used. In this embodiment mode, the second electrode is formed using aluminum.

For the layer containing an organic compound 66, either a low molecular material or a high molecular material may be used. The layer containing an organic compound 66 in the light-emitting device of this embodiment mode contains a compound having the spirofluorene derivative described in Embodiment Mode 1 introduced thereto as a substituent. Note that a material for forming the layer containing an organic compound 66 may be a material containing only an organic compound material, or it may be a material containing an inorganic material in a part. As a method for manufacturing the layer containing an organic compound 66, either a wet method or a dry method may be used, for example, an evaporation method, an ink-jet method, a spin coating method, a dip coating method, or the like. Further, normally the layer containing an organic compound 66 is formed by an appropriate combination of functional layers each having a different function, such as a hole injecting layer, a hole transporting layer, a hole blocking layer, a light-emitting layer, an electron transporting layer, and an electron injecting layer. However, a layer having two or more of these functions at the same time may be included in the layer containing an organic compound 66. In this embodiment, a layered structure including a hole injecting layer, a hole transporting layer, a light-emitting layer, an electron transporting layer, and an electron injecting layer is used as the layer containing an organic compound. In the light-emitting device of this embodiment mode, the spirofluorene derivative described in Embodiment Mode 1 is used as a hole transporting layer. There is no particular restriction on the other functional layers of the layer containing an organic compound 66. Regarding their materials, explanation was given in Embodiment Mode 2, so it will be omitted here.

Next, a silicon oxide film containing nitrogen is formed by plasma CVD as a passivation film. When using a silicon oxide film containing nitrogen, a silicon oxynitride film may be formed by plasma CVD using $SiH_4$, $N_2O$, and $NH_3$, or using $SiH_4$ and $N_2O$, or using a gas in which $SiH_4$ and $N_2O$ are diluted with Ar.

Alternatively, as the passivation film, a hydrogenated silicon oxynitride film formed using $SiH_4$, $N_2O$, and $H_2$ may be used. The first passivation film is, of course, not limited to a single layer structure, and it may have a single layer structure or a layered structure using another insulating layer containing silicon. Alternatively, a multilayer film including a carbon nitride film and a silicon nitride film, a multilayer film including styrene polymer, a silicon nitride film, or a diamond-like carbon film may be formed, instead of the silicon oxide film containing nitrogen.

Next, a display portion is sealed, to protect the light-emitting element from a substance which promotes deterioration of the light-emitting element, such as moisture. When the display portion is sealed with a counter substrate, the counter substrate is attached to the display portion with an insulating sealing material such that an external connection portion is exposed. A space between the counter substrate and the element substrate may be filled with an inert gas, such as dried nitrogen. Alternatively, a sealing material may be applied over the entire surface of the pixel portion and then the counter substrate may be attached thereto. An ultraviolet curing resin or the like is preferably used as the sealing material. A drying agent or a particle for maintaining a constant gap between the substrates may be mixed in the sealing material. Next, a flexible wiring substrate is attached to the external connection portion, thus completing a light-emitting device.

An example of a structure of a light-emitting device manufactured in the above-described manner will be explained, with reference to FIGS. 4A and 4B. Note that portions having similar functions are denoted by the same reference numerals, though they may have different shapes, and explanation thereof is omitted in some places. In this embodiment mode, the thin film transistor 70 having an LDD structure is connected to the light-emitting element 93 through the connection portion 61a.

Figure 4A:
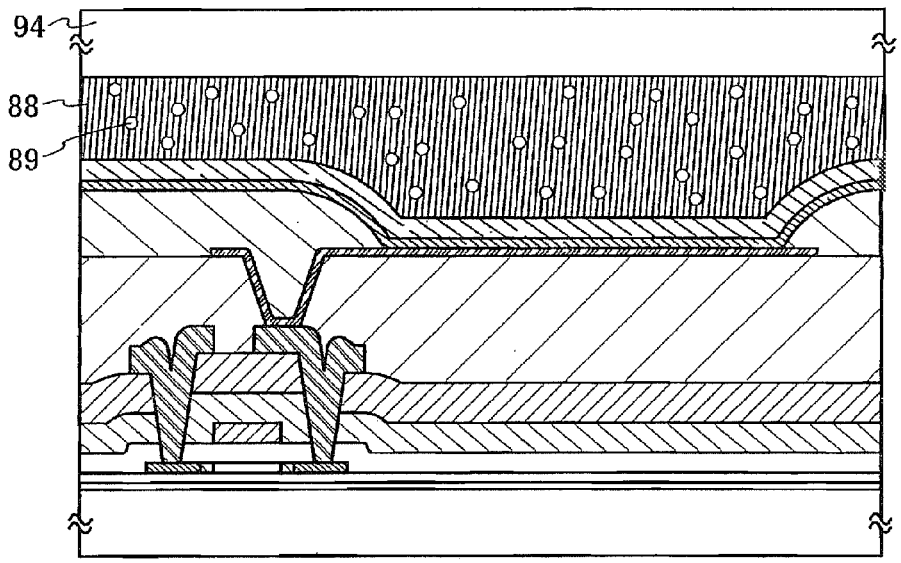
FIGS. 4A and 4B are cross sectional views showing an active matrix light-emitting device of the present invention.

FIG. 4A shows a structure where the first electrode 64 is formed using a conductive film having a light transmitting property, and light emitted from the layer containing an organic compound 66 is emitted toward the substrate 50. Note that the reference numeral 94 represents a counter substrate. After the light-emitting element 93 is formed, the counter substrate is firmly attached to the substrate 50 using a sealing material or the like. A space between the counter substrate 94 and the element is filled with a resin 88 having a light transmitting property, or the like, to seal the light-emitting element 93. Accordingly, deterioration of the light-emitting element 93 caused by moisture can be prevented. Preferably, the resin 88 has a hygroscopic property. Even more preferably, to further prevent the adverse influence of moisture, a drying agent 89 with a high light transmitting property is dispersed in the resin 88.

Figure 4B:
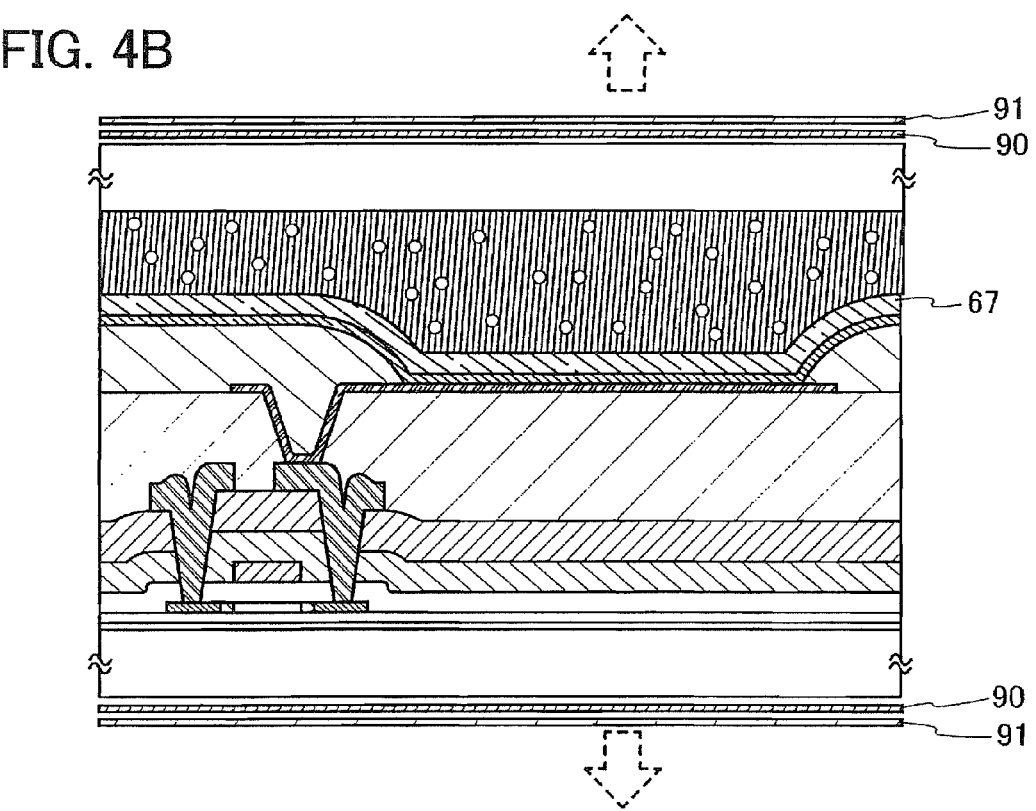

FIG. 4B shows a structure where both the first electrode 64 and the second electrode 67 are formed using conductive films having light transmitting properties, and light can be emitted toward both the substrate 50 and the counter substrate 94. Further, in this structure, by providing polarizing plates 90 on an outer side of the substrate 50 and an outer side of the counter substrate 94, a screen can be prevented from being transparent, thereby improving visibility. Protection films 91 may be provided outside of the polarizing plates 90.

In this embodiment mode, a top gate thin film transistor is used. However, a different form of thin film transistor, such as a bottom gate, may be used to form the light-emitting device.

Note that a light-emitting device having a display function in accordance with the present invention may employ either an analog video signal or a digital video signal. When a digital video signal is used, the video signal may use either a voltage or a current. When the light-emitting element emits light, a video signal input to a pixel may have either a constant voltage or a constant current. When a video signal has a constant voltage, a constant voltage is applied to a light-emitting element or a constant current flows through the light-emitting element. Further, when a video signal has a constant current, a constant voltage is applied to a light-emitting element or a constant current flows through the light-emitting element. A driving method where a constant voltage is applied to a light-emitting element is called a constant voltage drive, and a driving method where a constant current flows through a light-emitting element is called a constant current drive. In constant current drive, a constant current flows regardless of changes in resistance of a light-emitting element. Either of the above-mentioned driving methods may be used for a light-emitting device of the present invention and a driving method thereof.

Thus, a light-emitting device in accordance with the present invention including the spirofluorene derivative described in Embodiment Mode 1 in the layer containing an organic compound 66 can have high heat resistance, because the spirofluorene derivative has a high glass transition temperature (Tg). Further, since the spirofluorene derivative described in Embodiment Mode 1 has a wide energy gap, it is difficult for energy to move from other layers. Therefore, the light-emitting element 93 including the spirofluorene derivative described in Embodiment Mode 1 in the layer containing an organic compound 66 can have high light-emitting efficiency. Therefore, a light-emitting device of the present invention in this embodiment mode can have low power consumption.

This embodiment mode can be implemented by being combined with a suitable structure from Embodiment Mode 1 or Embodiment Mode 2.

Embodiment Mode 4

Figure 5A:
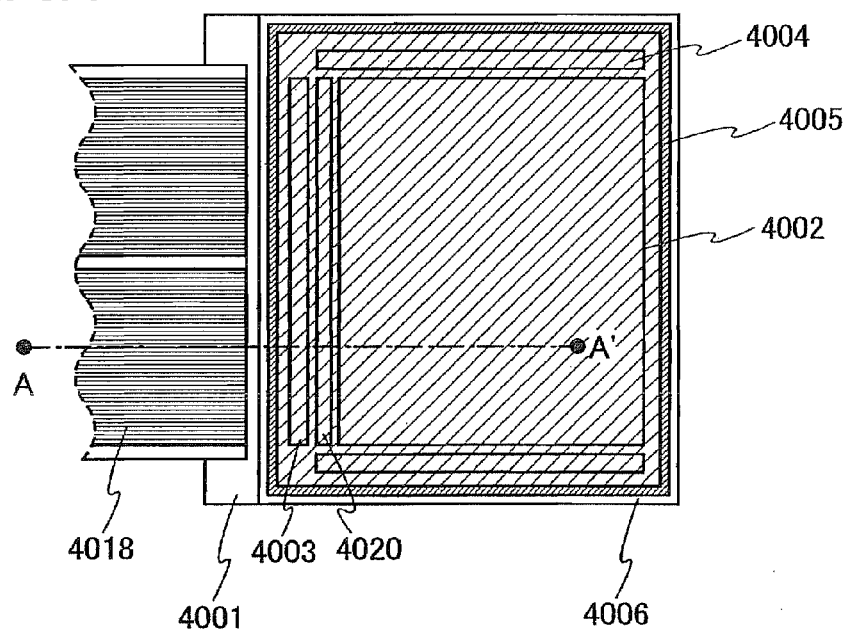
FIGS. 5A and 5B are a top view and a cross sectional view of a light-emitting device of the present invention.
Figure 5B:
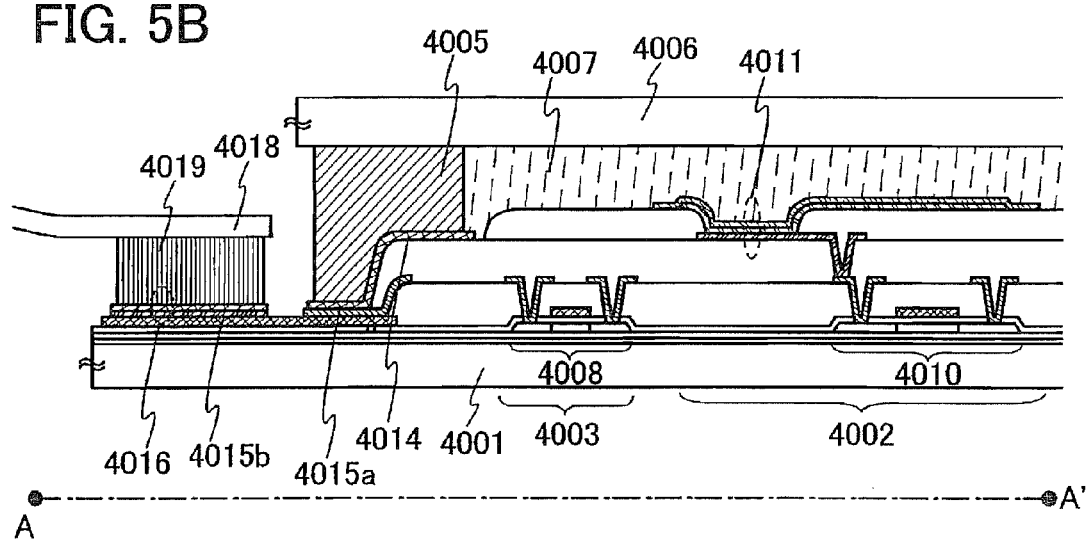

An outer appearance of a panel which is a light-emitting device of the present invention will be described in this embodiment mode, with reference to FIGS. 5A and 5B. FIG. 5A is a top view of a panel in which a transistor and a light-emitting element formed over a substrate are sealed with a sealing material that is formed between the substrate and a counter substrate 4006. FIG. 5B is a cross-sectional view of FIG. 5A. The light-emitting element mounted on this panel has a structure similar to the structure shown in Embodiment Mode 2.

A sealing material 4005 is provided so as to surround a pixel portion 4002, a signal line driver circuit 4003, and a scanning line driver circuit 4004, that are provided over a substrate 4001. The counter substrate 4006 is provided over the pixel portion 4002, the signal line driver circuit 4003, and the scanning line driver circuit 4004. Thus, the pixel portion 4002, the signal line driver circuit 4003, the scanning line driver circuit 4004, and a filler 4007 are hermetically sealed by the substrate 4001, the sealing material 4005, and the counter substrate 4006.

The pixel portion 4002, the signal line driver circuit 4003, and the scanning line driver circuit 4004, which are provided over the substrate 4001, have a plurality of transistors. In FIG. 5B, a thin film transistor 4008 included in the signal line driver circuit 4003 and a thin film transistor 4010 included in the pixel portion 4002 are shown.

Further, a light-emitting element 4011 is electrically connected to the thin film transistor 4010.

Also, a leading wire 4014 corresponds to a wire for supplying signals or power supply voltage to the pixel portion 4002, the signal line driver circuit 4003, and the scanning line driver circuit 4004. The leading wire 4014 is connected to a connection terminal 4016 through a leading wire 4015. The connection terminal 4016 is electrically connected to a terminal of a flexible printed circuit (FPC) 4018 through an anisotropic conductive film 4019.

Further, as the filler 4007, an inert gas such as nitrogen or argon can be used. Alternatively, an ultraviolet curing resin or a heat curing resin can be used. For example, polyvinyl chloride, acrylic, polyimide, an epoxy resin, a silicon resin, polyvinyl butyral, or ethylene vinylene acetate can be used.

Note that a panel in which a pixel portion having a light-emitting element is formed, and a module in which an IC is mounted on the panel, are included in the category of the light-emitting device of the present invention.

The above-mentioned signal line driver circuit 4003, the scanning line driver circuit 4004 and the IC, which are signal processing circuits, are control circuits of a light-emitting element. Light-emitting devices and electronic devices that include these control circuits can display various images on a panel by controlling lighting, non-lighting and luminance of a light-emitting element by the control circuits. Note that a signal processing circuit formed on an external circuit substrate connected by the FPC 4018 is also a control circuit.

A light-emitting device in accordance with the present invention as described above has a pixel portion with high heat resistance, because as a light-emitting element which forms a pixel portion, it includes the light-emitting element described in Embodiment Mode 2, which includes the spirofluorene derivative described in Embodiment Mode 1 in a layer containing an organic compound. Further, a light-emitting device in accordance with the present invention has low power consumption, because as a light-emitting element which forms a pixel portion, it includes the light-emitting element described in Embodiment Mode 2, which includes the spirofluorene derivative described in Embodiment Mode 1 in a layer containing an organic compound.

This embodiment mode can be implemented by being combined as appropriate with a suitable structure from any of Embodiment Modes 1 to 3.

Embodiment Mode 5

Pixel circuits and protection circuits included in the panel and module described in Embodiment Mode 4, and operations thereof will be described in this embodiment mode. Further, the cross-sectional views shown in FIGS. 2A to 2E and FIGS. 3A to 3C correspond to schematic cross-sectional views of a driving TFT 1403 and a light-emitting element 1405.

Figure 6A:
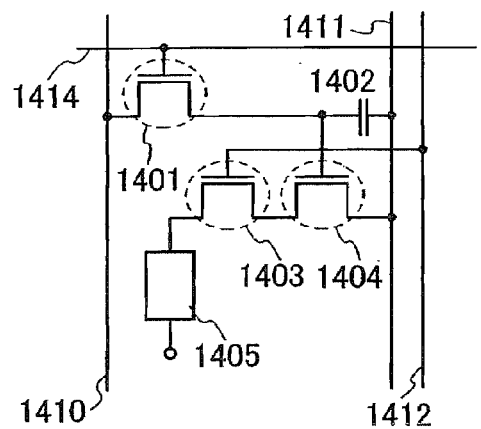
FIGS. 6A to 6F show examples of a pixel circuit of a light-emitting device of the present invention.

In a pixel shown in FIG. 6A, a signal line 1410 and power supply lines 1411 and 1412 are arranged in columns, whereas a scanning line 1414 is arranged in a row. The pixel also includes a switching TFT 1401, a driving TFT 1403, a current controlling TFT 1404, a capacitor element 1402, and a light-emitting element 1405.

Figure 6B:
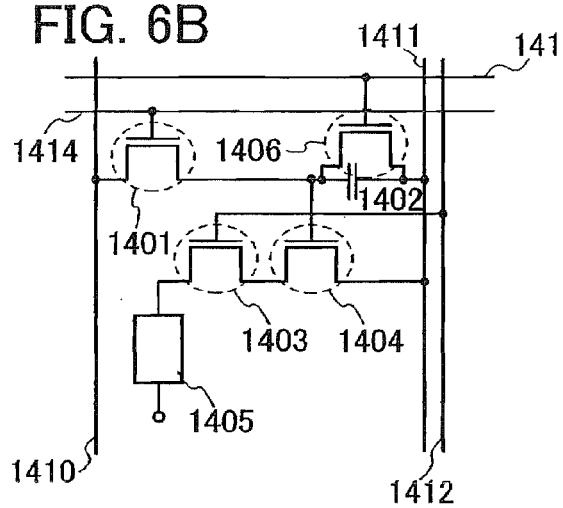
Figure 6C:
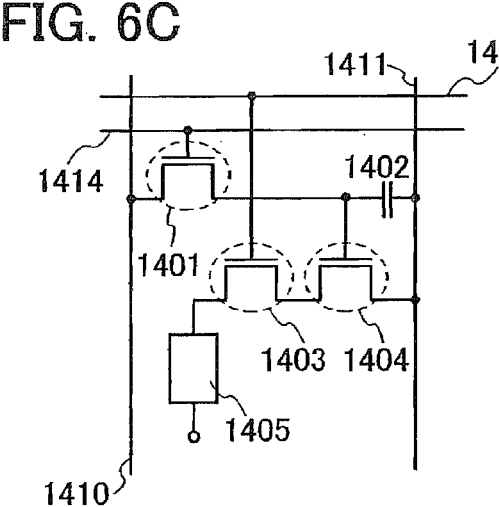
Figure 6D:
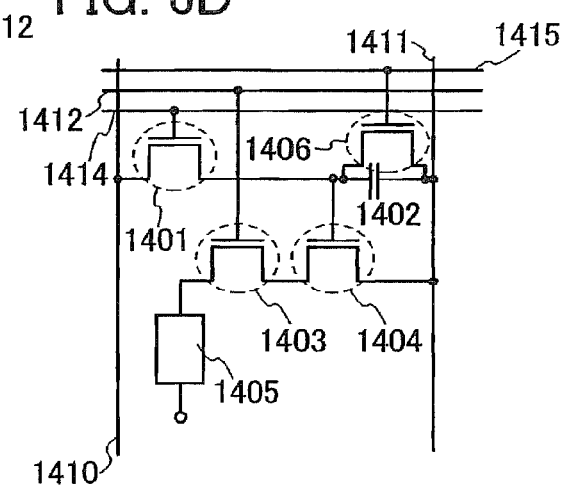

A pixel shown in FIG. 6C has the same structure as the one shown in FIG. 6A, except that a gate electrode of the driving TFT 1403 is connected to the power supply line 1412, which is arranged in a row. That is, the pixel in FIG. 6A and the pixel in FIG. 6C show the same equivalent circuit diagrams. However, in a case where the power supply line 1412 is arranged in a row (FIG. 6C), the power supply line is formed of a conductive film from a different layer than it is in a case where the power supply line 1412 is arranged in a column (FIG. 6A). In order to draw attention to wires which the gate electrode of the driving TFT 1403 is connected to and to show that the layers from which the wires are made are different, the pixels are illustrated separately, in FIG. 6A and FIG. 6C.

In the pixels shown in FIGS. 6A and 6C, the driving TFT 1403 and the current controlling TFT 1404 are connected in series, and the channel length (1403) and the channel width W(1403) of the driving TFT 1403, and the channel length L(1404) and the channel width W(1404) of the current controlling TFT 1404, may be set to satisfy the relation of L(1403)/W(1403):L(1404)/W(1404)=5 to 6000:1.

The driving TFT 1403 operates in a saturation region, and controls the amount of current flowing through the light-emitting element 1405, while the current controlling TFT 1404 operates in a linear region, and controls current supplied to the light-emitting element 1405. From a manufacturing point of view, it is preferable that both the TFT 1403 and the TFT 1404 have the same conductivity type, and in this embodiment mode, the TFTs 1403 and 1404 are formed as n-channel TFTs. Also, a depletion type TFT may be used as the driving TFT 1403, instead of an enhancement type TFT. In a light-emitting device of the present invention having the above-described structure, since the current controlling TFT 1404 operates in the linear region, slight fluctuations in $V_{gs}$ of the current controlling TFT 1404 do not affect the amount of current flowing through the light-emitting element 1405. That is, the amount of current flowing through the light-emitting element 1405 can be determined by the driving TFT 1403 operating in the saturation region. In accordance with the above-described structure, by controlling unevenness in luminance of a light-emitting element which is caused by variation in TFT characteristics, it is possible to provide a light-emitting device in which image quality is improved.

In the pixels shown in FIGS. 6A to 6D, the switching TFT 1401 controls input of video signals to the pixel. When the switching TFT 1401 is turned on and a video signal is input to the pixel, a voltage of the video signal is held in the capacitor element 1402. Although FIGS. 6A and 6C show a structure including the capacitor element 1402, the present invention is not limited to this. When a gate capacitor or the like can serve as a capacitor for holding a video signal, the capacitor element 1402 does not have to be provided.

A pixel shown in FIG. 6B has the same pixel structure as the one shown in FIG. 6A, except that a TFT 1406 and a scanning line 1415 have been added. Similarly, a pixel shown in FIG. 6D has the same pixel structure as the one shown in FIG. 6C, except that a TFT 1406 and a scanning line 1415 have been added.

The TFT 1406 is turned on or off under the control of the newly provided scanning line 1415. When the TFT 1406 is turned on, the charge held in the capacitor element 1402 is discharged, thereby turning the current controlling TFT 1404 off. That is, supply of current flowing to the light-emitting element 1405 can be forcibly stopped by providing the TFT 1406. Therefore, the TFT 1406 can also be referred to as an erasing TFT. In accordance with the structures shown in FIGS. 6B and 6D, a lighting period can start simultaneously with or immediately after the start of a writing period, before signals are written into all the pixels. Hence, the duty ratio can be improved.

Figure 6E:
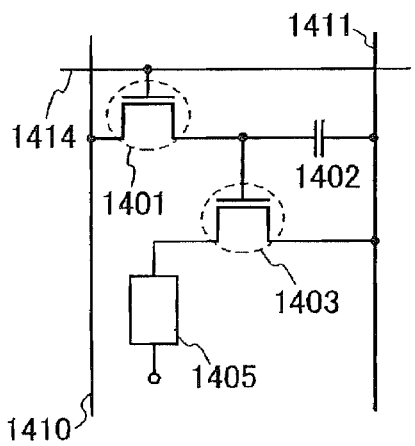
Figure 6F:
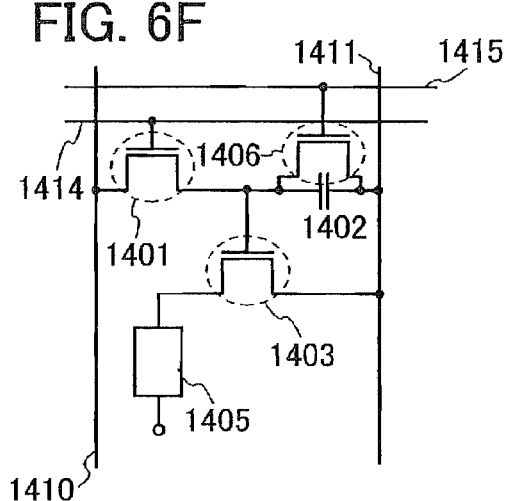

In a pixel shown in FIG. 6E, a signal line 1410 and a power supply line 1411 are arranged in columns, while a scanning line 1414 is arranged in a row. The pixel further includes a switching TFT 1401, a driving TFT 1403, a capacitor element 1402, and a light-emitting element 1405. A pixel shown in FIG. 6F has the same pixel structure as the one shown in FIG. 6E, except that a TFT 1406 and a scanning line 1415 have been added. Further, the structure shown in FIG. 6F also allows a duty ratio to be improved, by providing the TFT 1406.

As described above, various kinds of pixel circuits can be employed. Particularly when a thin film transistor is formed using an amorphous semiconductor film, it is preferable to make a semiconductor film of the driving TFT 1403 large. Therefore, in the above pixel circuits, a top emission type in which light generated in the layer containing an organic compound is emitted through a sealing substrate, is preferably employed.

It is thought that an active matrix light-emitting device such as this is advantageous, because when pixel density is increased, low voltage drive can be conducted, since a TFT is provided for each pixel.

An active matrix light-emitting device in which a TFT is provided in each pixel is described in this embodiment mode. However, a passive matrix light-emitting device can be formed. Since a TFT is not provided in each pixel in the passive matrix light-emitting device, a high aperture ratio is obtained. In the case of a light-emitting device in which light generated is emitted toward both sides of a layer containing an organic compound, when a passive matrix light-emitting device is employed, transmittance increases.

Next, a case in which diodes are provided as protection circuits in a scanning line and a signal line will be described, using an equivalent circuit diagram shown in FIG. 6E.

Figure 7:
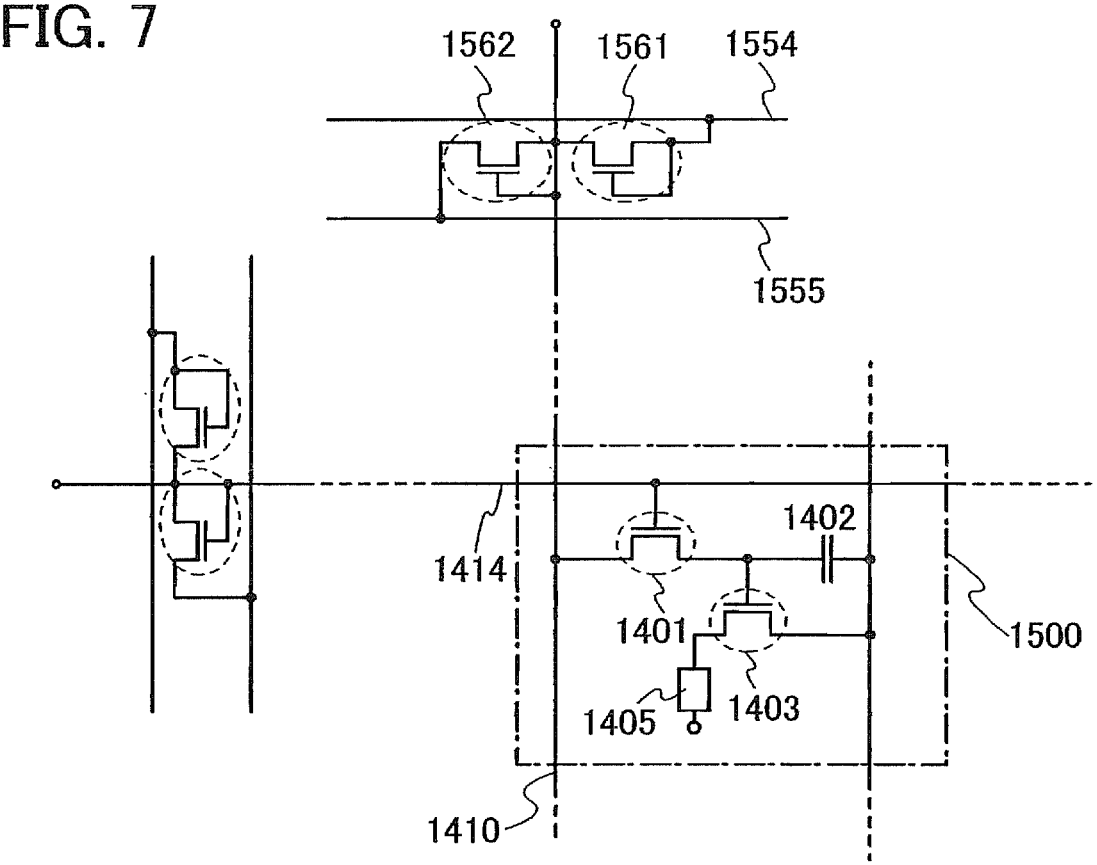
FIG. 7 shows an example of a protection circuit of a light-emitting device of the present invention.

In FIG. 7, a switching TFT 1401, a driving TFT 1403, a capacitor element 1402, and a light-emitting element 1405 are provided in a pixel portion 1500. In the signal line 1410, diodes 1561 and 1562 are provided. The diodes 1561 and 1562 are manufactured in accordance with the above-described embodiment mode, as are the switching TFT 1401 and the driving TFT 1403. Each diode includes a gate electrode, a semiconductor layer, a source electrode, a drain electrode, and the like. The diodes 1561 and 1562 operate as diodes by connecting the gate electrode to the drain electrode or the source electrode.

Common potential lines 1554 and 1555 which connect to the diodes are formed in the same layer as the gate electrodes. Therefore, in order to connect the common potential lines 1554 and 1555 with the source electrodes or the drain electrodes of the diodes, it is necessary to form a contact hole in a gate insulating layer.

A diode provided in the scanning line 1414 has a similar structure.

In this way, according to the present invention, protection diodes provided in an input stage can be formed simultaneously. Further, the position where the protection diodes are formed is not limited to this. They can be provided between a driver circuit and a pixel.

This embodiment mode can be implemented by being combined as appropriate with a suitable structure from any of Embodiment Modes 1 to 4.

By including the protection circuits described above, a light-emitting device in accordance with the present invention can have improved reliability.

Embodiment Mode 6

Figure 8A:
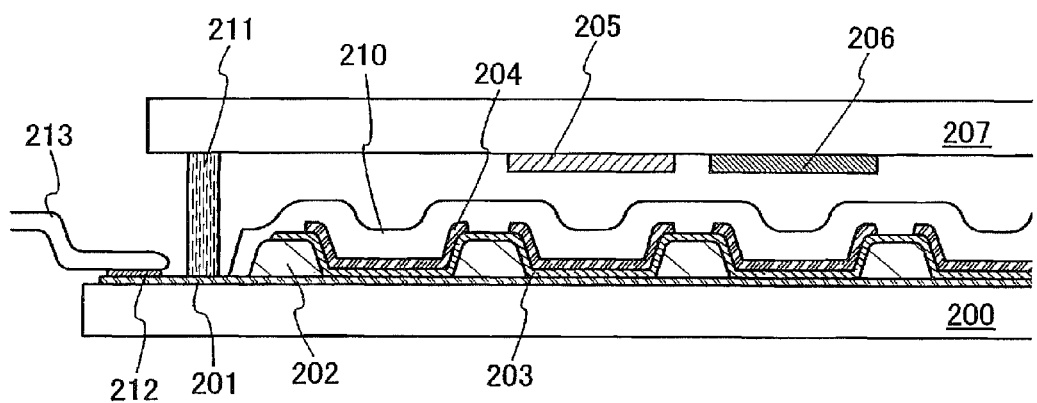
FIGS. 8A and 8B are a cross sectional view and a top view of a passive matrix light-emitting device of the present invention.

FIG. 8A shows an example of a structure of a light-emitting device of the present invention. FIG. 8A shows a portion of a cross-sectional view of a pixel portion of a passive matrix light-emitting device with a forward tapered structure. The light-emitting device of the present invention shown in FIG. 8A includes a substrate 200, a first electrode 201 of a light-emitting element, a partition wall 202, a layer containing an organic compound 203, a second electrode 204 of the light-emitting element, and a counter substrate 207.

A light-emitting element is formed in a portion where the layer containing an organic compound 203 is sandwiched between the first electrode 201 and the second electrode 204 of the light-emitting device. The first electrode 201 and the second electrode 204 are formed in a striped pattern and cross each other at right angles. At a portion where they intersect, a light-emitting element is formed. The partition wall 202 is formed parallel to the second electrode 204, insulating a light-emitting element from another light-emitting element which also has the first electrode 201.

In this embodiment mode, for specific materials and structures of the light-emitting element, which includes the first electrode 201, the second electrode 204, and the layer containing an organic compound 203, refer to Embodiment Mode 2.

In addition, the substrate 200, the partition wall 202, and the counter substrate 207 in FIG. 8A correspond to the substrate 50, the partition wall 65, and the counter substrate 94 of Embodiment Mode 3, respectively. Regarding their structures, materials, and effects, they are similar to those in Embodiment Mode 3, so description of them is omitted here. The description in Embodiment Mode 3 should be referred to.

A protection film 210 is formed in a light-emitting device, to prevent moisture or the like from entering. A counter substrate 207, formed of glass, quartz, a ceramic material such as alumina, a synthetic material, or the like, is firmly attached by a sealing adhesive 211. An external input terminal portion is connected to an external circuit through an anisotropic conductive film 212 using a flexible printed wiring substrate 213. The protection film 210 may be formed of silicon nitride. Alternatively, it may be formed as a stacked structure of carbon nitride and silicon nitride, which enhances a gas barrier property while decreasing stress.

Figure 8B:
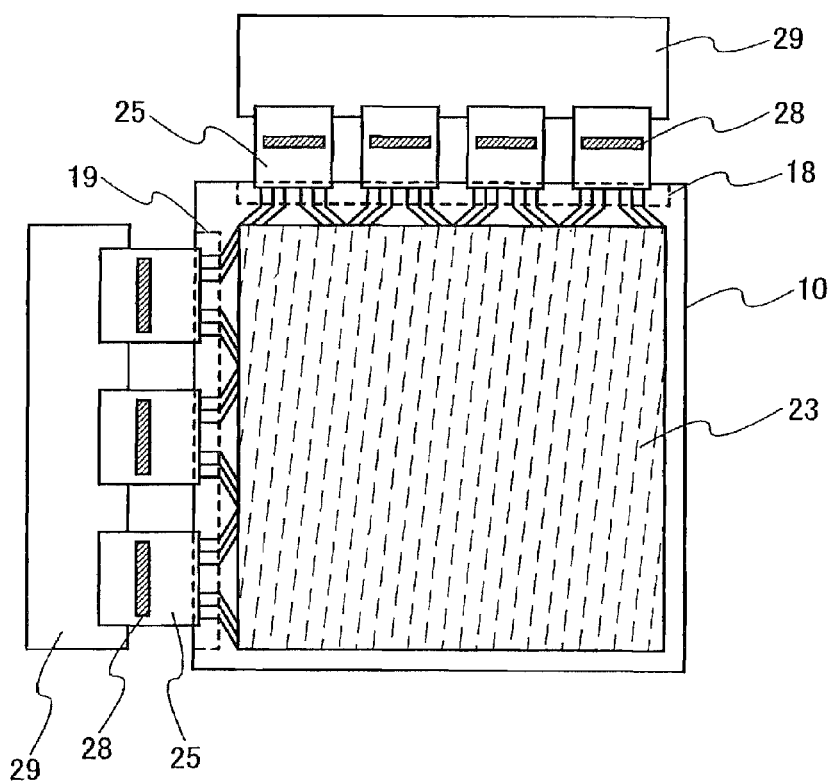

FIG. 8B shows a module in which an external circuit is connected to the panel shown in FIG. 8A. The module is electrically connected to an external circuit substrate. A power source circuit and a signal processing circuit are formed on the external circuit substrate by firmly fixing a flexible printed wiring substrate 25 to external input terminal portions 18 and 19. Further, a driver IC 28, which is one of the external circuits, may be mounted by either a COG method or a TAB method. FIG. 8B shows the driver IC 28, which is one of the external circuits, mounted by a COG method. The signal processing circuit and the driver IC 28 which are formed on the external circuit substrates are control circuits of a light-emitting element. Light emitting devices and electronic devices which include these control circuits can display various images on a panel by controlling lighting, non-lighting and luminance of a light-emitting element by the control circuits.

Note that the panel and the module correspond to one mode of a light emitting device of the present invention, and are both included in the scope of the present invention.

A light-emitting device in accordance with the present invention, such as the one above, has a pixel portion with high heat resistance, because as a light-emitting element which forms the pixel portion, it includes the light-emitting element described in Embodiment Mode 2, which includes the spirofluorene derivative described in Embodiment Mode 1 in a layer containing an organic compound. Further, a light-emitting device in accordance with the present invention has low power consumption, because as a light-emitting element which forms a pixel portion, it includes the light-emitting element described in Embodiment Mode 2, which includes the spirofluorene derivative described in Embodiment Mode 1 in a layer containing an organic compound.

Embodiment Mode 7

Representative examples of electronic devices of the present invention will be explained, with reference to FIGS. 9A to 9E. An electronic device of the present invention includes at least a light-emitting element which includes the spirofluorene derivative described in Embodiment Mode 1, or the light-emitting element described in Embodiment Mode 2, and a control circuit which control the light-emitting element. As examples of electronic devices of the present invention, the following can be given: a video camera, a digital camera, a goggle type display (a head mounted display), a navigation system, audio playback equipment (e.g., a car audio component), a computer, a game machine, a portable information terminal (e.g., a mobile computer, a mobile phone, a portable game machine, or an electronic book), an image reproducing device equipped with a recording medium (specifically, a device which reproduces a recording medium such as a DVD (Digital Versatile Disc), and includes a display capable of displaying the reproduced image), and the like.

Figure 9A:
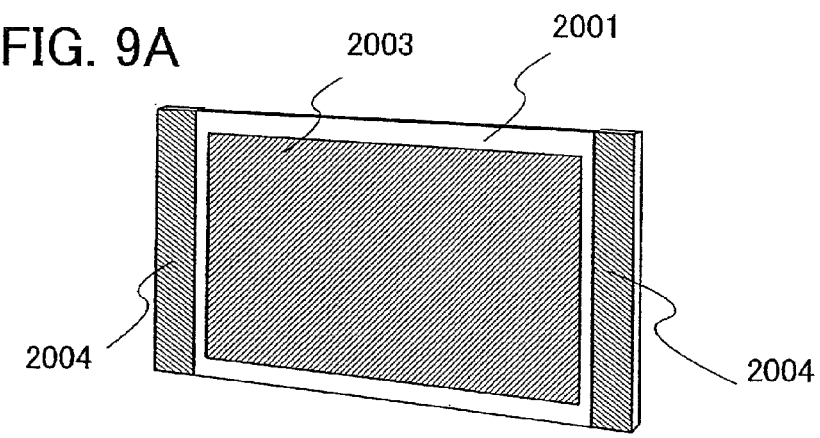

FIG. 9A shows a light-emitting device which corresponds to, for example, a monitor or the like of a television set or a personal computer. The light-emitting device includes a housing 2001, a display portion 2003, speaker portions 2004, and the like. The light-emitting device of the present invention has high heat resistance, because in the display portion 2003, it includes a light-emitting element which includes the spirofluorene derivative with a high glass transition temperature (Tg) described in Embodiment Mode 1. To improve contrast, a polarizing plate or a circular polarizing plate is preferably provided in the pixel portion. For example, a film including a ¼λ plate, a ½λ plate, and a polarizing plate, in that order, is preferably provided over a sealing substrate. In addition, an anti-reflection film may be provided over the polarizing plate.

Figure 9B:
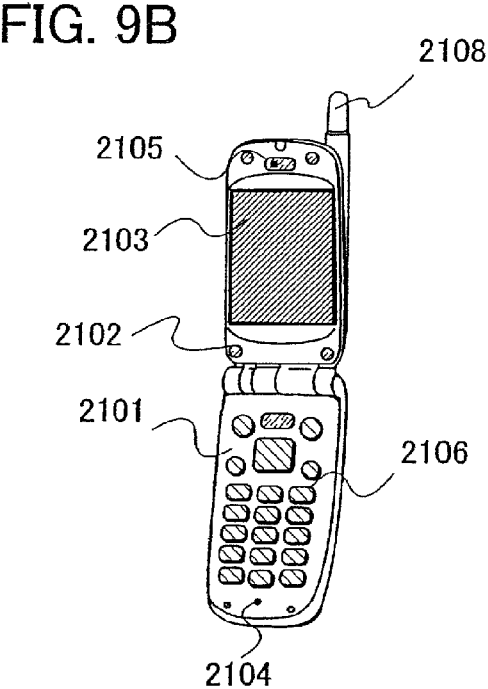

FIG. 9B shows a mobile phone which can be used for viewing and listening to television. It includes a main body 2101, a housing 2102, a display portion 2103, an audio input portion 2104, an audio output portion 2105, operation keys 2106, an antenna 2108, and the like. The mobile phone of the present invention has high heat resistance, because in the display portion 2103, it includes a light-emitting element which includes the spirofluorene derivative with a high glass transition temperature (Tg) described in Embodiment Mode 1.

Figure 9C:
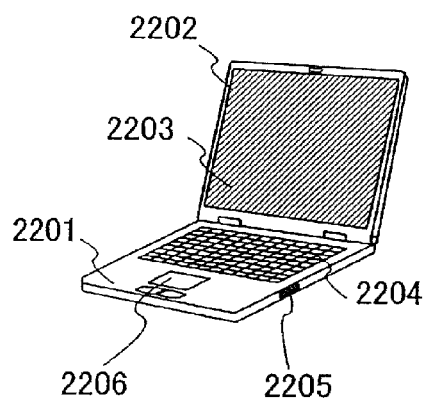

FIG. 9C shows a computer which includes a main body 2201, a housing 2202, a display portion 2203, a keyboard 2204, an external connection port 2205, a pointing mouse 2206, and the like. The computer of the present invention has high heat resistance, because in the display portion 2203, it includes a light-emitting element which includes the spirofluorene derivative with a high glass transition temperature (Tg) described in Embodiment Mode 1. Although a notebook computer is shown as an example in FIG. 9C, the present invention can also be applied to a desktop computer or the like.

Figure 9D:
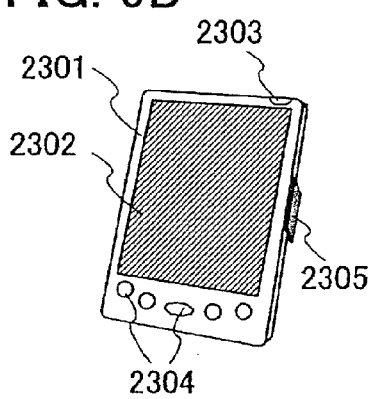

FIG. 9D shows a mobile computer which includes a main body 2301, a display portion 2302, a switch 2303, operation keys 2304, an infrared port 2305, and the like. The mobile computer of the present invention has high heat resistance, because in the display portion 2302, it includes a light-emitting element which includes the spirofluorene derivative with a high glass transition temperature (Tg) described in Embodiment Mode 1.

Figure 9E:
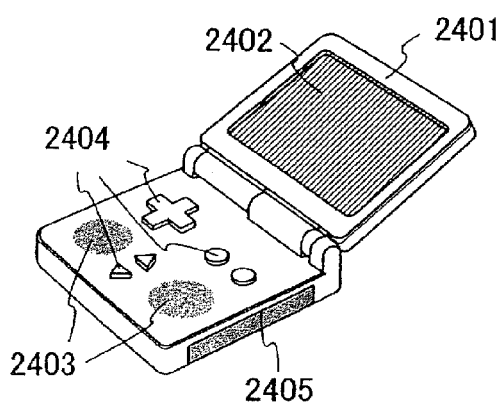

FIG. 9E shows a portable game machine which includes a housing 2401, a display portion 2402, speaker portions 2403, operation keys 2404, a recording medium insertion portion 2405, and the like. The portable game machine of the invention has high heat resistance, because in the display portion 2402, it includes a light-emitting element which includes the spirofluorene derivative with a high glass transition temperature (Tg) described in Embodiment Mode 1.

As described above, the range of application of the present invention is extremely wide, and the invention can be applied to electronic devices in any field.

This embodiment mode can be implemented by being combined as appropriate with a suitable structure from any of Embodiment Modes 1 to 6.

Embodiment 1

In this example, a method of synthesis of 2-[N-(4-diphenylaminophenyl)-N-phenylamino]-spiro-9,9'-bifluorene (abbrev.: DPASF), which is expressed by Structural Formula 25 in Embodiment Mode 1, will be explained.

DPASF can be synthesized by conducting a coupling reaction with 2-bromo-spiro-9,9'-bifluorene, which is expressed by Formula 111 below, and N-[4-(diphenylamino) phenyl]aniline (abbrev.: DPA), which is expressed by the Formula 112 below, using a metal catalyst.

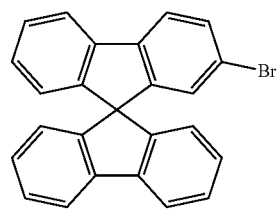

(111)

(112)

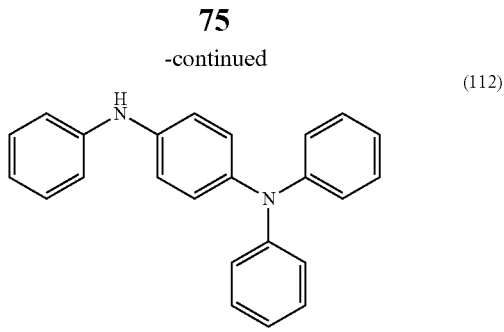

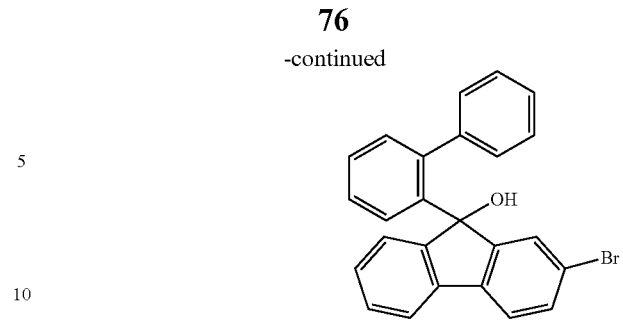

Step 1

A method of synthesis of 2-bromo-spiro-9,9'-bifluorene will be explained.

1.26 g (0.052 mol) of magnesium was put in a 100 mL three-necked flask to which a dropping funnel and a Dimroth condenser were connected, and the flask was evacuated. The magnesium was activated by 30 minutes of heating and stirring. After cooling to room temperature, the flask was placed under a nitrogen gas flow. 5 mL of diethyl ether and several drops of dibromoethane were added, and 11.65 g (0.050 mol) of 2-bromobiphenyl dissolved in 15 mL of diethyl ether was slowly delivered from the dropping funnel by drops into the mixture. After the dropping was complete, the mixture was refluxed for 3 hours and made into a Grignard reagent. 11.7 g (0.045 mol) of 2-bromo-9-fluorenone and 40 mL of diethyl ether were put in a 200 mL three-necked flask to which a dropping funnel and a Dimroth condenser were connected. To this reaction solution, the synthesized Grignard reagent was slowly delivered by drops from the dropping funnel. After the dropping was complete, the mixture was refluxed for 2 hours, and then stirred at room temperature for about 12 hours. After the reaction was complete, the solution was washed twice with saturated ammonia chloride solution. An aqueous layer was extracted twice with ethyl acetate and combined with an organic layer, and the solution was washed with a saturated saline solution. After drying with magnesium sulfate, suction filtration and concentration were conducted, and a solid of 9-(biphenyl-2-yl)-2-bromo-9-fluorenol was obtained, weighing 18.76 g in a yield of 90%.

A synthesis scheme (a-1) of 9-(biphenyl-2-yl)-2-bromo-9-fluorenol is shown below.

(a-1)

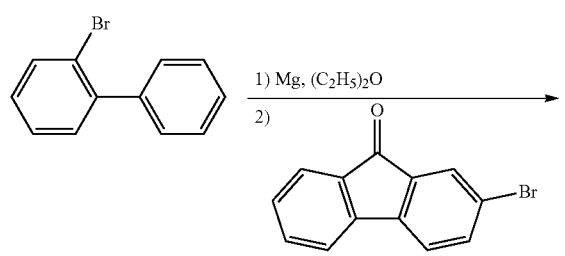

18.76 g (0.045 mol) of the synthesized 9-(biphenyl-2-yl)-2-bromo-9-fluorenol and 100 mL of glacial acetic acid were put in a 200 mL three-necked flask, several drops of concentrated hydrochloric acid were added, and the mixture was refluxed for 2 hours. After the reaction was complete, a precipitate was collected by suction filtration, and the precipitate was filtered and washed with a saturated sodium hydrogen carbonate solution and water. The brown solid obtained was recrystallized with ethanol, and a light-brown powdered solid was obtained, weighing 10.24 g in a yield of 57%. It was confirmed that this light-brown powdered solid was 2-bromo-spiro-9,9'-fluorene by a nuclear magnetic resonance method (NMR).

$^1$H NMR of the compound obtained is shown below:

$^1$H NMR (300 MHz, CDCl$_3$) δ ppm: 7.86-7.79 (m, 3H), 7.70 (d, 1H, J=8.4 Hz), 7.50-7.47 (m, 1H), 7.41-7.34 (m, 3H), 7.12 (t, 3H, J=7.7 Hz), 6.85 (d, 1H, J=2.1 Hz), 6.74-6.76 (m, 3H)

A synthesis scheme (a-2) of 2-bromo-spiro-9,9'-bifluorene is shown below.

(a-2)

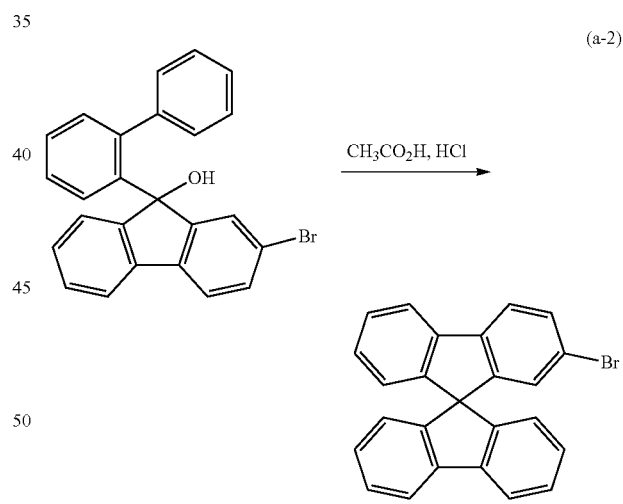

Step 2

A method of synthesis of DPA will be explained.

25.19 g (0.102 mol) of triphenylamine, 18.05 g (0.102 mol) of N-bromosuccinimide, and 400 mL of ethyl acetate were put in a 1000 mL Erlenmeyer flask, and were stirred for about 12 hours at room temperature in the air. After the reaction was complete, an organic layer was washed twice with a saturated sodium carbonate solution. Then, an aqueous layer was extracted twice with ethyl acetate, combined with the organic layer, and washed with saturated saline solution. The solution was dried with magnesium sulfate, naturally filtered and concentrated, and a colorless solid was obtained. The solid was recrystallized with ethyl acetate and hexane, and 22.01 g of a colorless powdered solid was obtained, in a yield of 66%. It was confirmed that this colorless powdered solid was 4-bromotriphenylamine by a nuclear magnetic resonance method (NMR). The measurement results according to a nuclear magnetic resonance method (NMR) are shown below.

$^1$H NMR of the compound obtained is shown below:

$^1$H NMR (300 MHz, CDCl$_3$) δ ppm: 7.32 (d, 2H, J=8.7 Hz), 7.29-7.23 (m, 4H), 7.08-7.00 (m, 6H), 6.94 (d, 2H, J=8.7 Hz)

Next, a synthesis scheme (b-1) of 4-bromotriphenylamine will be shown.

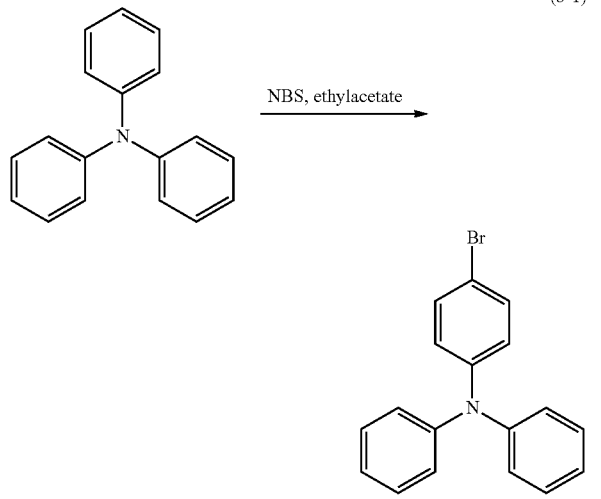

A dehydrated toluene solution (5 mL) of 4-bromotriphenylamine (559 mg, 6 mmol), Pd(dba)$_2$ (345 mg, 0.6 mmol), and t-BuONa (577 mg, 6 mmol) was degassed. Then, aniline (559 mg, 6 mmol) and P(t-Bu)$_3$ (0.37 mL 1.8 mmol) were added. The mixture was heated and stirred for 5 hours under a nitrogen atmosphere at 80° C. By thin-film chromatography, it was ascertained that the raw material, 4-bromotriphenylamine, had disappeared. A saturated saline solution was added to complete the reaction, and an aqueous layer was extracted with about 100 ml of ethyl acetate. The organic layer was dried by magnesium sulfate, and filtered. After the filtrate was concentrated, purification was conducted in an ethyl acetate:hexane=1:20 silica gel column, and the target product was obtained as a viscous liquid. By adding hexane to this viscous liquid and applying ultrasonic waves, a cream-colored powder was extracted. This mixture was concentrated, and DPA was obtained in a yield of 42%.

$^1$H NMR of the DPA obtained is shown: $^1$H NMR (300 MHz, CDCl$_3$) δ ppm: 7.35-6.83 (m, 19H), 5.60 (s, 1H)

Further, the $^{13}$C NMR is shown: $^{13}$C-NMR (75.5 MHz, DMSO-d$_6$) δ ppm: 147.8, 143.7, 140.2, 139.4, 129.4, 129.3, 127.1, 122.4, 122.0, 119.8, 118.4, 116.8

Next, a synthesis scheme (b-2) of DPA is shown.

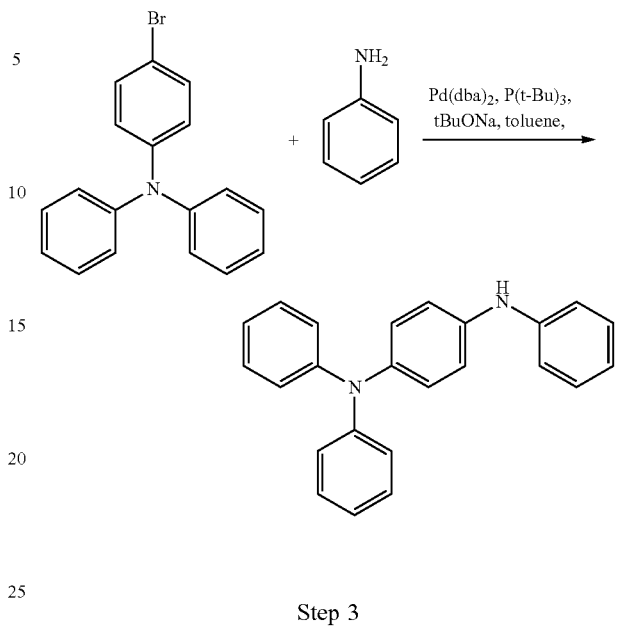

Step 3

A method of synthesis of DPASF will be explained.

2.5 g (63 mmol) of 2-bromo-spiro-9,9'-bifluorene, 2.2 g (6.5 mmol) of DPA, 37.6 mg (0.063 mmol) of bis(dibenzylideneacetone)palladium(0), and 2.1 g (21 mmol) of t-butoxysodium were placed in a 100 mL three-necked flask. Nitrogen substitution was carried out, 50 mL of toluene was added, and the mixture was degassed at reduced pressure. 0.1 mL of tri(t-butyl)phosphine (10 wt % hexane solution) was added, and the mixture was stirred for 11 hours at 80° C. After the reaction, filtration was done through Celite. The filtrate was washed 3 times with water and once with a saturated saline solution, and dried with magnesium sulfate. The reaction mixture was naturally filtered, the filtrate was concentrated, and an oily product was obtained. This oily product was purified by silica gel column chromatography (hexane:toluene=7:3), and after recrystallizing from dichloromethane and hexane, the target product of a white powdered solid was obtained, weighing 3.8 g in a yield of 91%. It was confirmed that this white powdered solid was DPASF by a nuclear magnetic resonance method (NMR).

Figure 10:
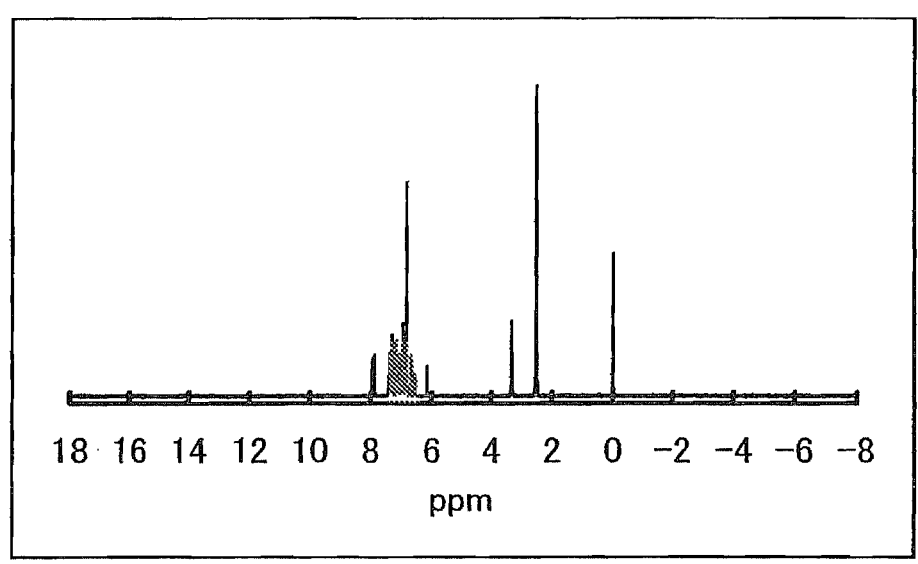
FIG. 10 is a $^1$H NMR chart of DPASF.

$^1$H NMR of the compound obtained is shown below. Further, a $^1$H NMR chart is shown in FIG. 10.

$^1$H NMR (300 MHz, DMSO-d$_6$); δ=7.95 (d, J=7.80 Hz, 2H), 7.90 (d, J=7.80 Hz, 2H), 7.40-7.77 (m, 26H), 6.67 (d, J=7.20 Hz, 2H), 6.55 (d, J=7.20 Hz, 1H), 6.16 (d, J=2.33 Hz, 1H)

A synthesis scheme (c-1) of DPASF is shown below.

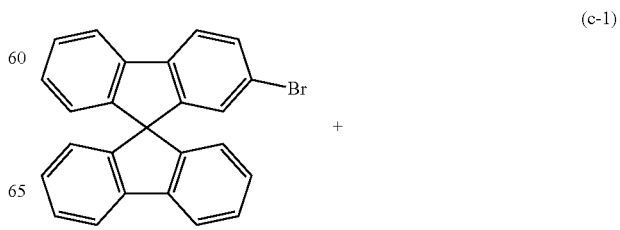

-continued

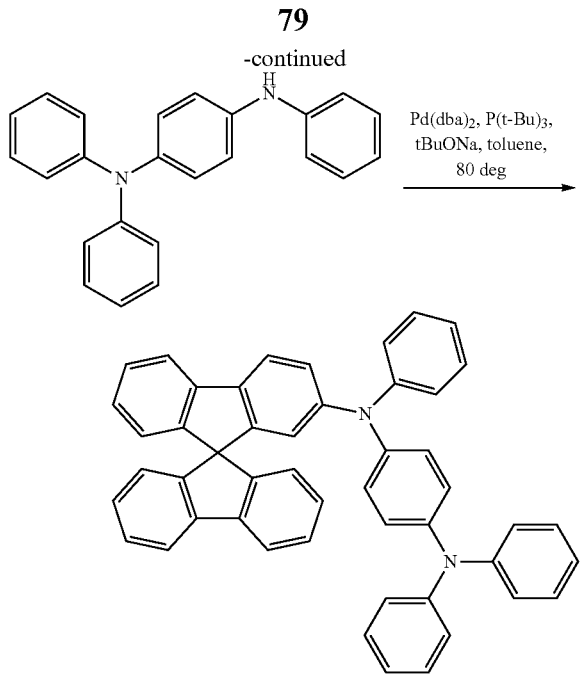

Sublimation purification was conducted for 24 hours on 3.75 g of the DPASF obtained, at a pressure of 200 Pa and a temperature of 330° C. 2.82 g was recovered, in a yield of 75%.

Further, the decomposition temperature (Td) of the DPASF was measured with a thermo-gravimetric/differential thermal analyzer (a Seiko Instruments Inc. TG/DTA320), and was found to be 382° C. Thus, it was found that DPASF showed a high Td.

Figure 11:
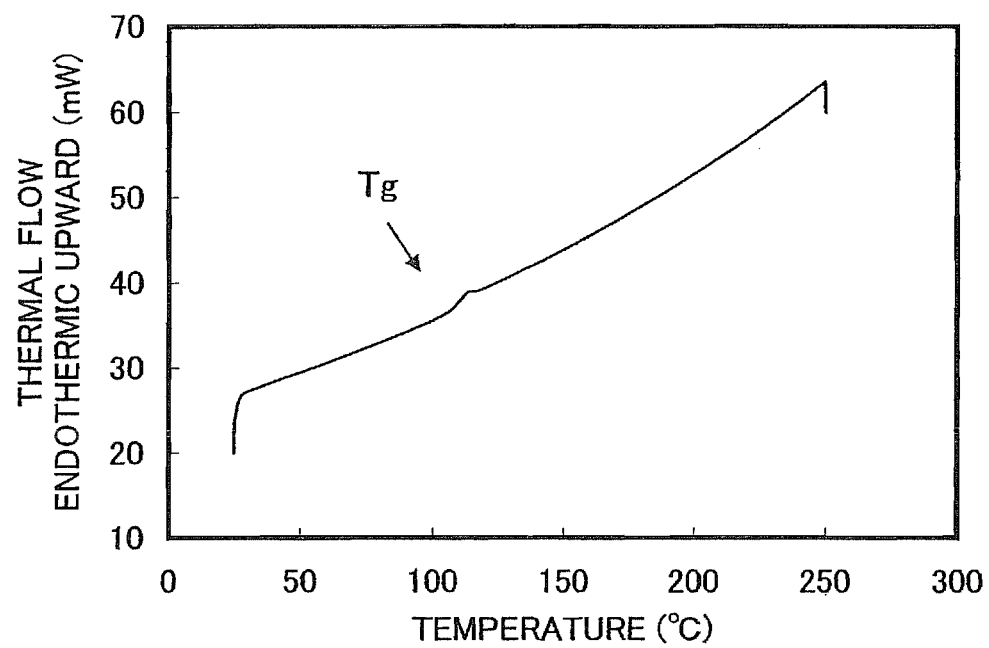
FIG. 11 is a DSC chart of DPASF.

Furthermore, the glass transition temperature (Tg) was measured using a differential scanning calorimeter (a Perkin-Elmer Co., Ltd. Pyris 1 DSC). First, a sample was melted by heating it from 25° C. to 250° C. at 40° C. per minute. Next it was cooled to 25° C., at 40° C. per minute. Next, by raising the temperature to 250° C. at 10° C. per minute, the DSC chart in FIG. 11 was obtained. From this chart, it can be seen that the glass transition temperature (Tg) of DPASF is 107° C. Thus, it was found that DPASF has a high glass transition temperature. In addition, the endothermic peak on the DSC chart of when the sample was first melted was observed. It shows the melting point, which was 223° C.

Figure 12:
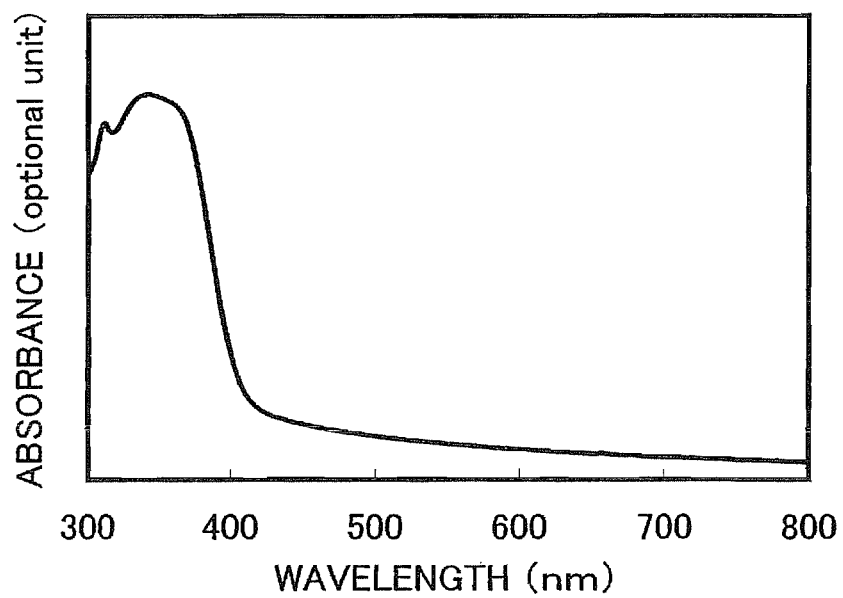
FIG. 12 shows an absorption spectrum of a thin film of DPASF.
Figure 13:
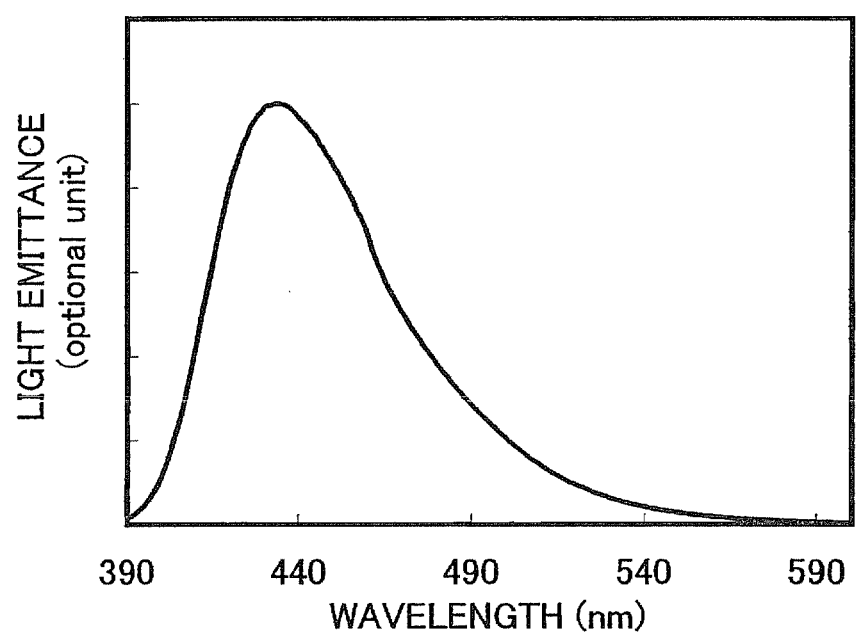
FIG. 13 shows a light emission spectrum of a thin film of DPASF.

The absorption spectrum and emission spectrum of DPASF in a thin film state are shown in FIGS. 12 and 13. It was found that the maximum absorption wavelength of DPASF in a thin film state was 341 nm and the maximum emission wavelength was 434 nm. Using the absorption spectrum data from FIG. 12, the absorption edge was obtained from a Tauc plot. Using the energy of that absorption edge as an energy gap, the energy gap of DPASF was found to be 3.1 eV. 9,10-diphenylanthracene, which exhibits representative blue emission, has an energy gap of 2.9 eV, so it can be seen that DPASF has an amply large energy gap. Further, the HOMO level in a thin film state was measured with an ambient photoelectron spectroscopy (using a Riken Keiki Co., Ltd. AC-2), and was found to be −5.3 eV. Using the HOMO level and the energy gap, the LUMO level was found to be −2.2 eV.

Further, the electrochemical stability of DPASF was evaluated using cyclic voltammetry (CV). An electrochemical analyzer (a BAS Inc. ALS model 600A) was used as the measuring device. The solution for the CV measurement was prepared by using dehydrated dimethylformamide (DMF) as a solvent, dissolving a supporting electrolyte of tetra-n-butylammonium perchlorate (n-$Bu_4NClO_4$) to a concentration of 100 mM, and dissolving DPASF, the object of measurement, to a concentration of 1 mM. A platinum electrode (a BAS Inc. PTE platinum electrode) was used as a working electrode, another platinum electrode (a BAS Inc. Pt counter electrode (5 cm) for VC-3) was used as an auxiliary electrode, and an Ag/$Ag^+$ electrode (a BAS Inc. RE5 non-aqueous solvent reference electrode) was used as a reference electrode. The scanning speed was set at 0.1 V per second, and a 100 cycle measurement was conducted.

Figure 14:
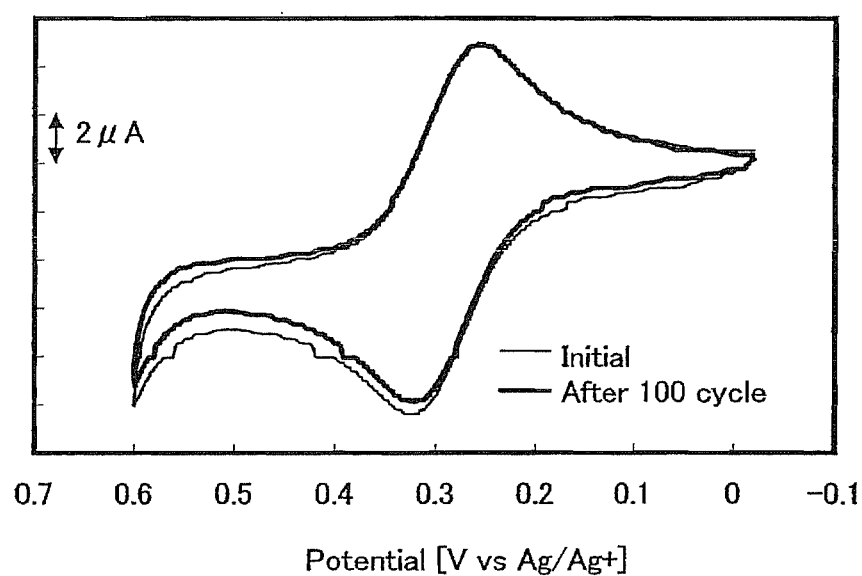
FIG. 14 is a CV chart of DPASF.

CV measurement results for the oxidation side of DPASF film are shown in FIG. 14. The graph which shows the measurement results shows a reversible peak, there being almost no change in the cyclic voltammogram even when oxidation is repeated 100 times. This means that DPASF has tolerance to the cycle of oxidation and reduction which follows the oxidation.

Embodiment 2

In this example, a method of synthesis of 2-[N-(9-phenylcarbazole-3-yl)-N-phenylamino]-spiro-9,9′-bifluorene (abbrev.: PCASF), which is expressed by the Structural Formula 35 in Embodiment Mode 1, will be explained.

PCASF can be synthesized by conducting a coupling reaction with 2-bromo-spiro-9,9′-bifluorene, which is expressed by the Formula 111 below, and 3-(N-phenylamino)-9-phenylcarbazole (abbrev.: PCA), which is expressed by the Formula 113 below, using a metal catalyst. Note that the method of synthesis of 2-bromo-spiro-9,9′-bifluorene was explained in Step 1 of Example 1, so it will not be explained here.

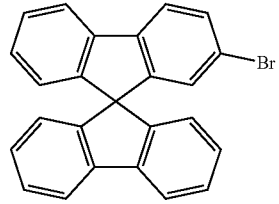

(111)

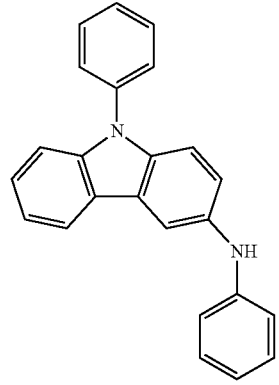

(113)

Step 1

A method of synthesis of PCA will be explained.

First, 24.3 g (100 mmol) of N-phenylcarbazole was dissolved in 600 mL of glacial acetic acid, 17.8 g (100 mmol) of N-bromosuccinimide was slowly added, and the mixture was stirred for about 12 hours at room temperature. This glacial acetic acid solution was added dropwise to 1 L of iced water while stirring. The white solid extracted was washed 3 times with water. This solid was dissolved in 150 mL of diethyl ether, and washed with a saturated sodium hydrogen carbonate solution and water. This organic layer was dried with magnesium sulfate. This was filtered, and the filtrate obtained was concentrated. To the residue obtained was added about 50 mL of methanol, and by irradiation with ultrasonic waves, the residue was dissolved evenly in the solution. By leaving this solution at rest, a white solid was extracted. This white solid was filtered, and by drying the solid, 28.4 g of 3-bromo-9-phenylcarbazole in a white powdered form was obtained (yield rate: 88%).

Next, a synthesis scheme (d-1) of 3-bromo-9-phenylcarbazole will be shown.

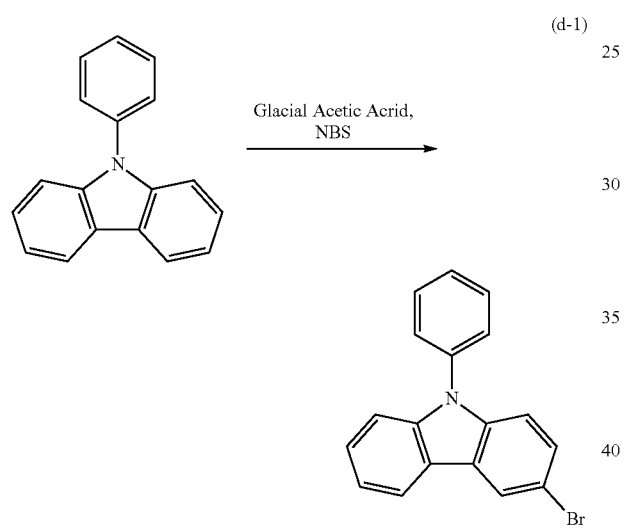

Next, under nitrogen, 110 mL of dehydrated xylene and 7.0 g (75 mmol) of aniline were added to a mixture containing 19 g (60 mmol) of 3-bromo-9-phenylcarbazole, 340 mg (0.6 mmol) of bis(dibenzylideneacetone)palladium(0) (abbrev.: Pd(dba)$_2$), 1.6 g (3.0 mmol) of 1,1-bis(diphenylphosphino)ferrocene (abbrev.: DPPF), and 13 g (180 mmol) of sodium-tert-butoxide (abbrev.: tert-BuONa). This mixture was then heated and stirred for 7.5 hours at 90° C. under a nitrogen atmosphere. After the reaction was complete, about 500 mL of toluene warmed to 50° C. was added to this suspension. Then, it was filtered through Florisil, alumina and Celite, and the filtrate obtained was concentrated. To this residue was added hexane-ethyl acetate, and irradiation with ultrasonic waves was conducted. The suspension obtained was filtered, the residue was dried, and 15 g of a cream-colored powder was obtained (yield rate: 75%). It was confirmed that this cream-colored powder was 3-(N-phenylamino)-9-phenylcarbazole (abbrev.: PCA) by a nuclear magnetic resonance method (NMR).

Figure 15A:
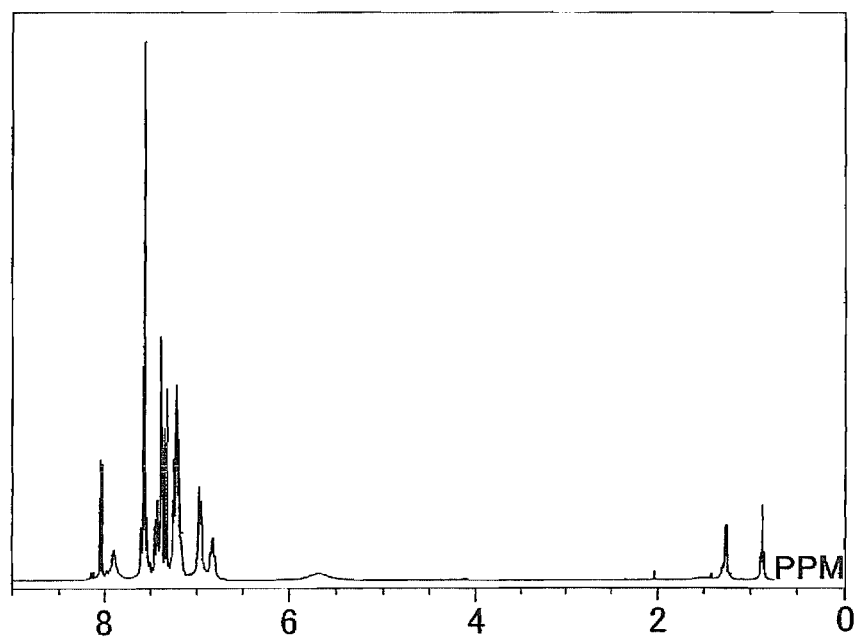
FIGS. 15A and 15B are $^1$H NMR charts of PCA.
Figure 15B:
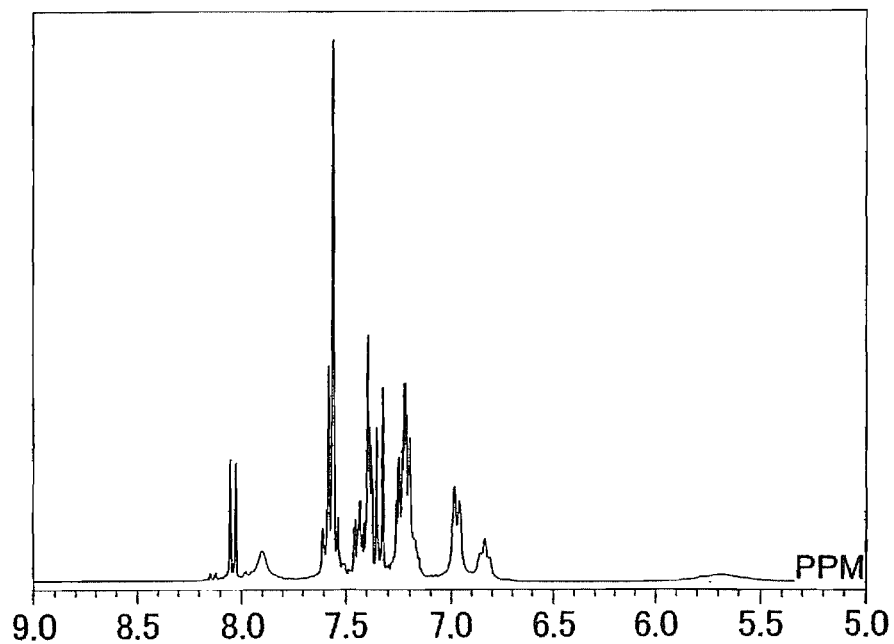

Next, $^1$H NMR of this compound will be shown. Also, $^1$H NMR charts are shown in FIGS. 15A and 15B. Note that the chart in FIG. 15B is an enlarged version of the 5 ppm to 9 ppm range in FIG. 15A.

$^1$H NMR (300 Mhz, CDCl$_3$); δ=6.84 (t, J=6.9 Hz, 1H), 6.97 (d, J=7.8 Hz, 2H), 7.20-7.61 (m, 13H), 7.90 (s, 1H), 8.04 (d, 7.8 Hz, 1H).

Figure 50A:
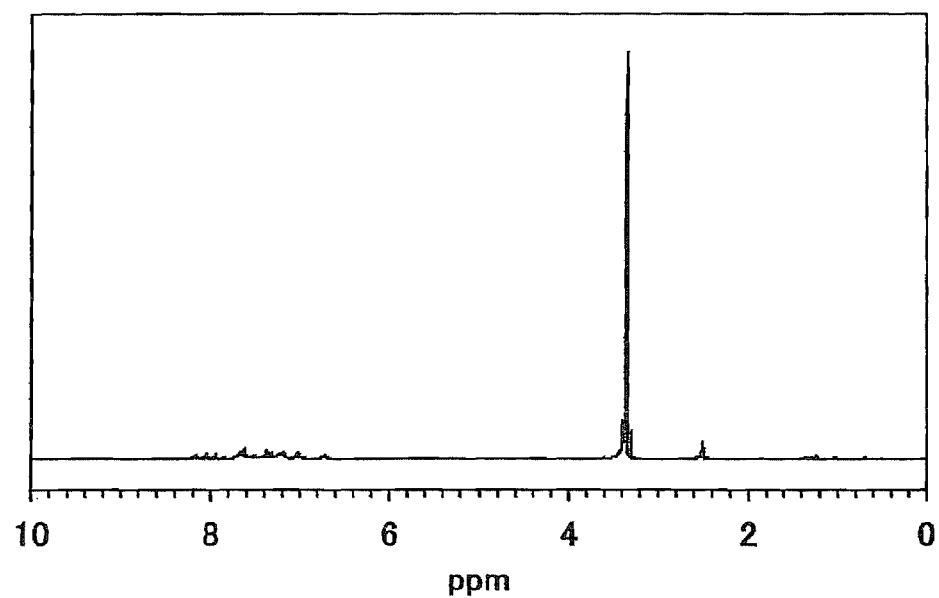
FIGS. 50A and 50B are $^1$H NMR charts of PCA.
Figure 50B:
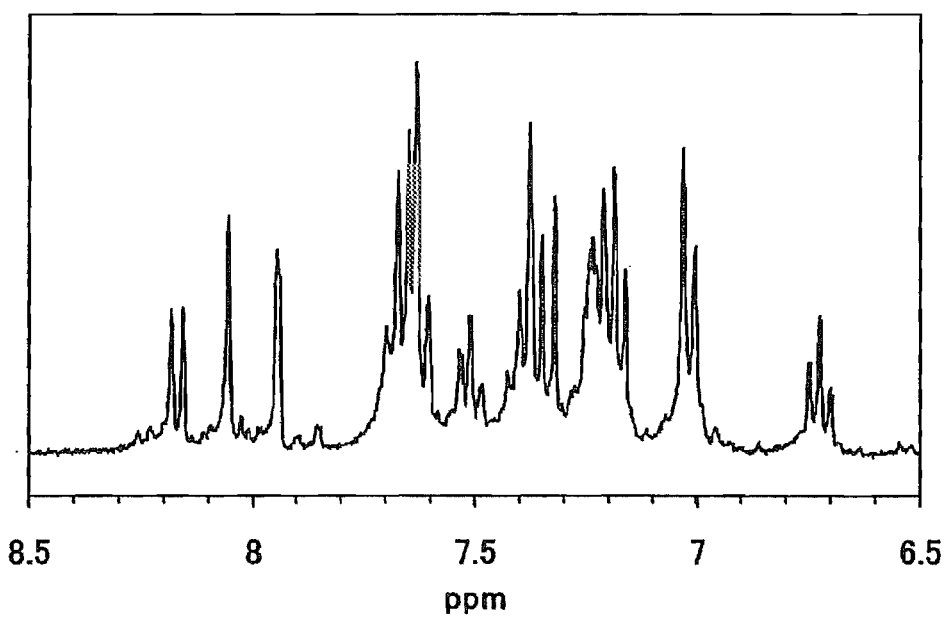

Next, 1H NMR of this compound will be shown. Also, $^1$H NMR charts are shown in FIGS. 50A and 50B. Note that the chart in FIG. 50B is an enlarged version of the 6.5 ppm to 8.5 ppm range in FIG. 50A.

$^1$H NMR (300 MHz, DMSO-d$_6$); δ=6.73 (t, J=7.5 Hz, 1H), 7.02 (d, J=8.1 Hz, 2H), 7.16-7.70 (m, 12H), 7.95 (s, 1H), 8.06 (s, 1H), 8.17 (d, J=7.8 Hz).

Figure 51A:
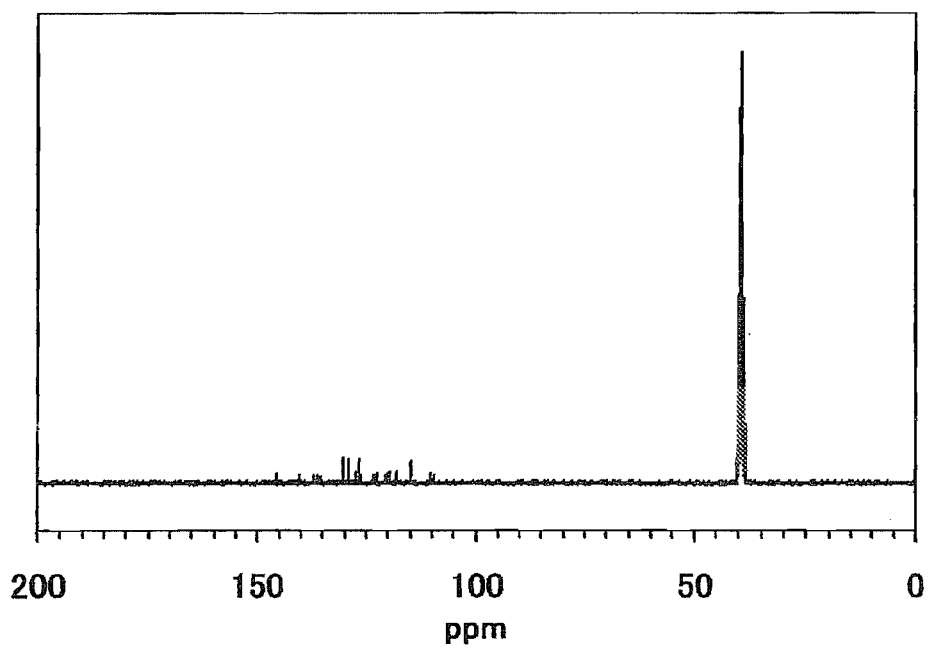
FIGS. 51A and 51B are $^{13}$C NMR charts of PCA.
Figure 51B:
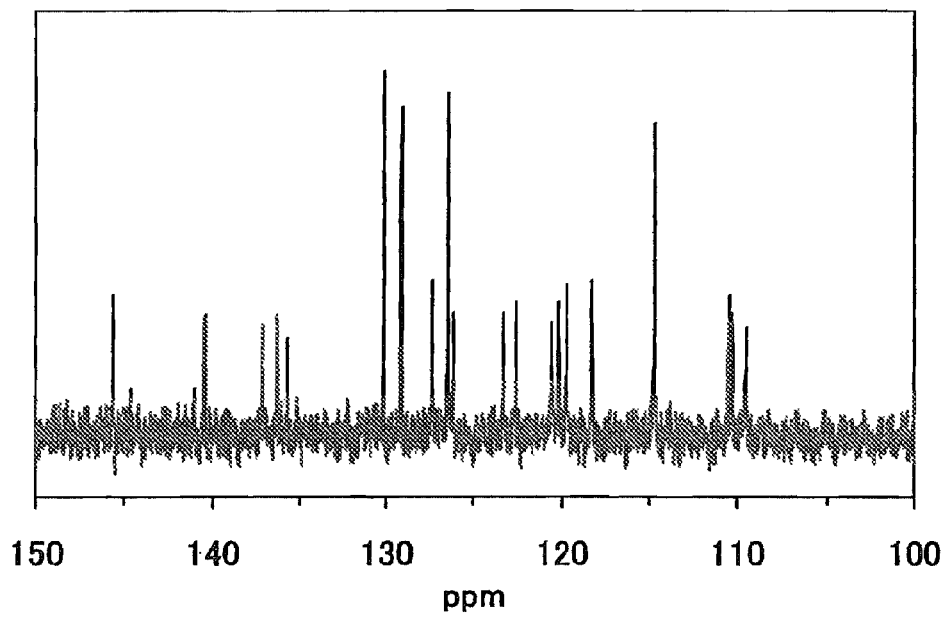

In addition, the $^{13}$C NMR will now be shown. Also, $^{13}$C NMR charts are shown in FIGS. 51A and 51B. Note that the chart in FIG. 51B is an enlarged version of the 100 ppm to 150 ppm range in FIG. 51A.

$^{13}$C NMR (75.5 MHz, DMSO-d$_6$); δ=109.55, 110.30, 110.49, 114.71, 118.22, 119.70, 120.14, 120.61, 122.58, 123.35, 126.18, 126.48, 127.37, 129.15, 130.14, 135.71, 136.27, 137.11, 140.41, 145.61.

Next, a synthesis scheme (d-2) of 3-(N-phenylamino)-9-phenylcarbazole is shown.

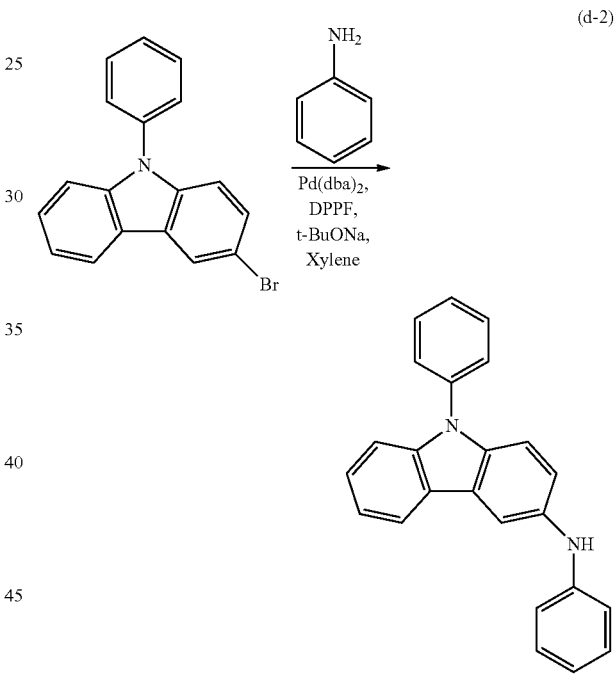

Step 2

A method of synthesis of PCASF will be explained.

1.0 g (2.5 mmol) of 2-bromo-spiro-9,9'-bifluorene, 846 mg (2.5 mmol) of 3-(N-phenylamino)-9-phenylcarbazole, 15.0 mg (0.025 mmol) of bis(dibenzylideneacetone)palladium(0), and 1.0 g (10 mmL) of t-butoxy sodium were placed in a 100 mL three-necked flask, and nitrogen substitution was carried out. 10 mL of toluene was added, and the mixture was degassed at reduced pressure. 0.05 mL of tri(t-butyl)phosphine (10 wt % hexane solution) was added, and the mixture was stirred for 3.5 hours at 80° C. After the reaction, the mixture was filtered through Celite. The filtrate was washed 3 times with water and once with a saturated saline solution, and dried with magnesium sulfate. The reaction mixture was naturally filtered, the filtrate was concentrated, and an oily product was obtained. This oily product was purified by silica gel column chromatography (hexane:ethyl acetate=7:3), then recrystallized with dichloromethane and hexane. 1.0 g of a white powdered solid was obtained, in a yield of 63%. It was confirmed that this white powdered solid was PCASF by a nuclear magnetic resonance method (NMR).

Figure 16:
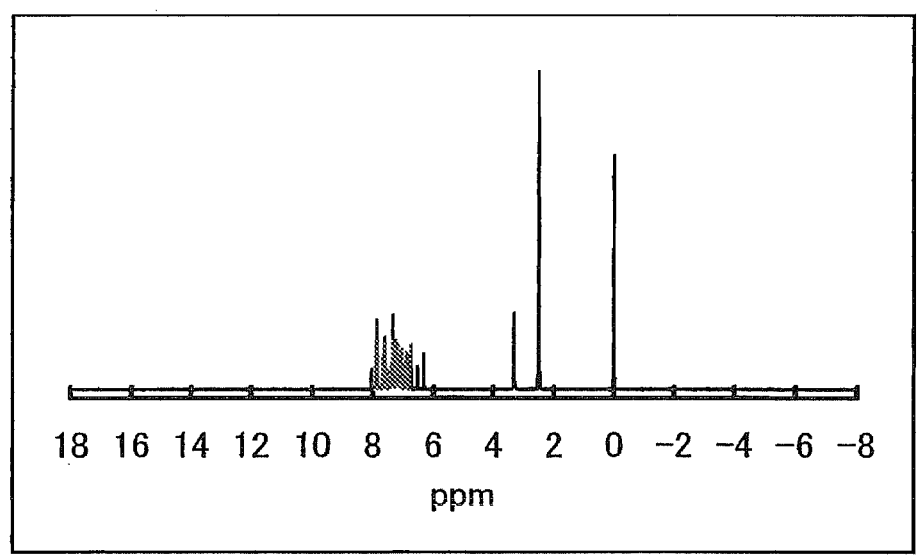
FIG. 16 is a $^1$H NMR chart of PCASF.

Next, $^1$H NMR of this compound is shown. Also, a $^1$H NMR chart of PCASF is shown in FIG. 16.

$^1$H NMR (300 MHz, DMSO-d$_6$); δ=8.04 (d, J=7.21 Hz, 1H), 7.89-7.85 (m, 5H), 7.69-7.50 (m, 5H), 7.43-7.31 (m, 5H), 7.27-7.10 (m, 6H), 7.07-7.01 (m, 2H), 6.95-6.86 (m, 4H), 6.73 (d, J=7.80 Hz, 2H), 6.52 (d, J=7.80 Hz, 1H), 6.31 (d, J=2.4 Hz, 1H)

Next, a synthesis scheme (e-1) of PCASF will be shown.

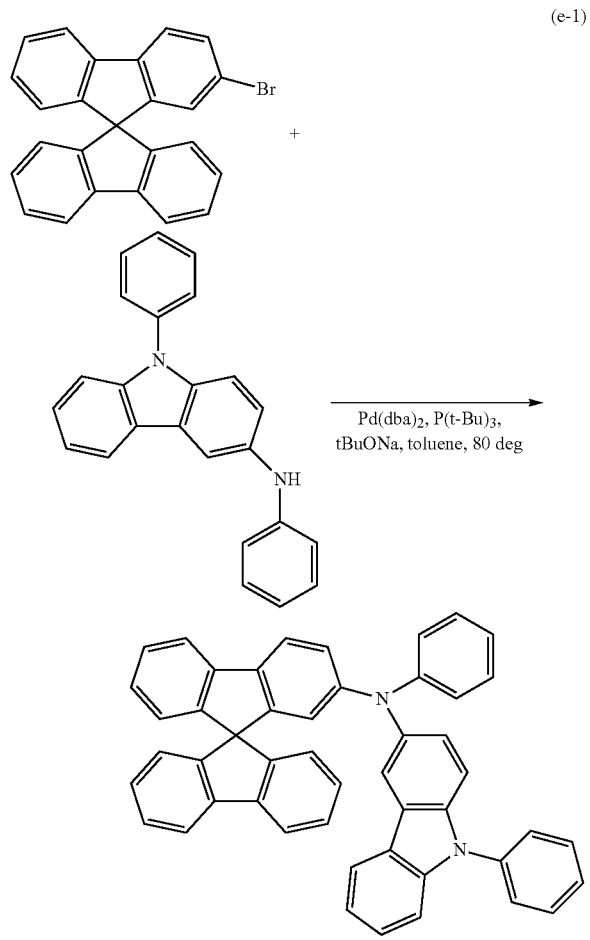

(e-1)

Sublimation purification was conducted for 24 hours on 551 mg of the PCASF obtained at a pressure of 200 Pa and a temperature of 320° C. 480 mg was recovered, in a yield of 87%.

Further, the decomposition temperature (Td) of the PCASF was measured with a thermo-gravimetric/differential thermal analyzer (a Seiko Instruments Inc. TG/DTA320). It was found to be 371° C. Thus, it was found that PCASF shows a high Td.

Figure 17:
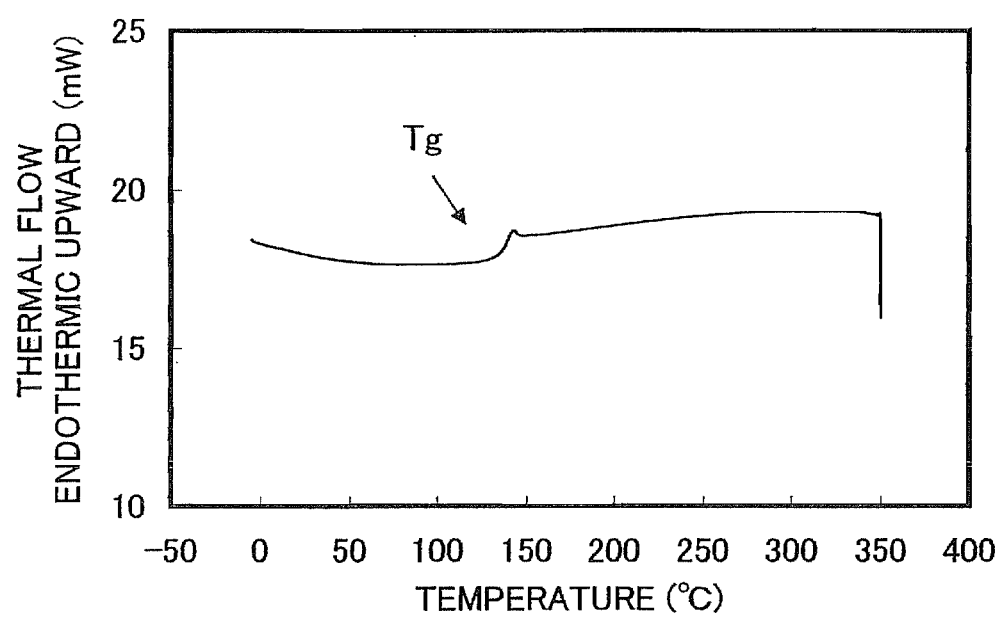
FIG. 17 is a DSC chart of PCASF.

Further, the glass transition temperature (Tg) was measured using a differential scanning calorimeter (a PerkinElmer Co., Ltd Pyris 1 DSC). First, a sample was heated from −10° C. to 350° C. by 40° C. per minute, then cooled to −5° C. by 40° C. per minute. Next, by raising the temperature to 350° C. by 10° C. per minute, the DSC chart in FIG. 17 was obtained. From this chart, it can be seen that the glass transition temperature (Tg) of PCASF is 134° C. Thus, it was found that PCASF has a high glass transition temperature. Note that in this measurement, the endothermic peak, which shows the melting point, was not observed.

Figure 18:
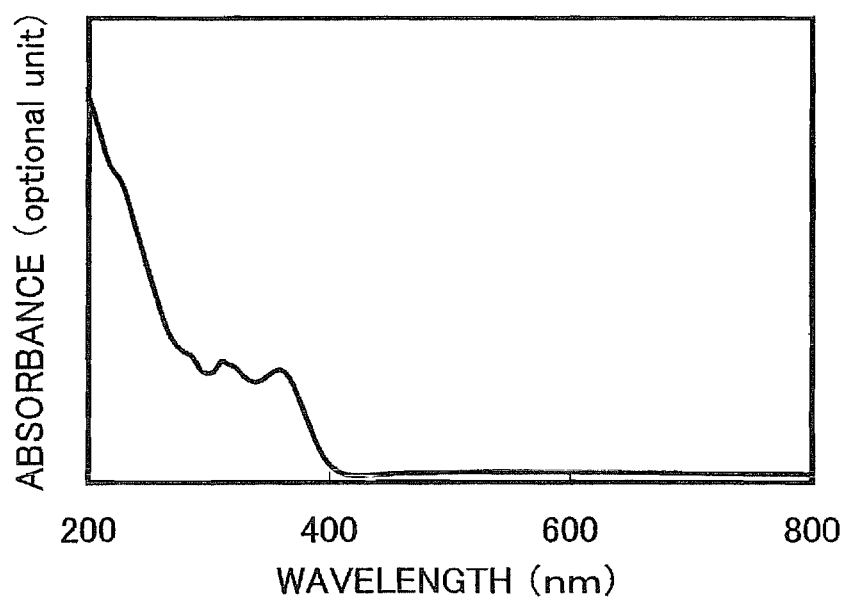
FIG. 18 shows an absorption spectrum of a thin film of PCASF.
Figure 19:
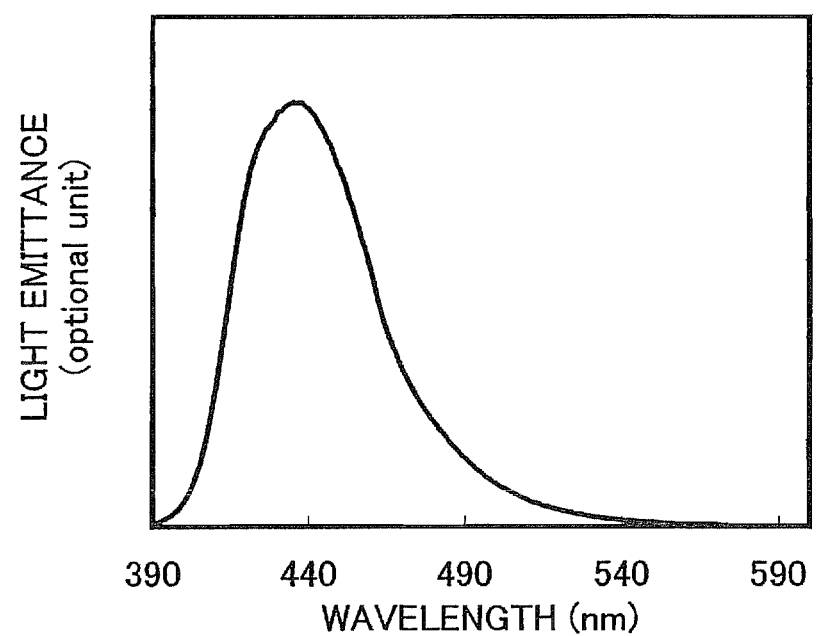
FIG. 19 shows a light emission spectrum of a thin film of PCASF.

The absorption spectrum and emission spectrum of PCASF in a thin film state are shown in FIGS. 18 and 19. It was found that in a thin film state, PCASF had absorption peaks at 312 nm and 359 nm, and the maximum emission wavelength was 437 nm. Using the absorption spectrum data from FIG. 18, the absorption edge was obtained from a Tauc plot. Using the energy of that absorption edge as an energy gap, the energy gap of PCASF was found to be 3.2 eV. 9,10-diphenylanthracene, which exhibits representative blue emission, has an energy gap of 2.9 eV, so it was found that PCASF has an amply large energy gap. Further, the HOMO level in a thin film state was measured with an ambient photoelectron spectroscopy (using a Riken Keiki Co., Ltd AC-2), and was found to be −5.3 eV. Using the HOMO level and the energy gap, the LUMO level was found to be −2.1 eV.

Further, the electrochemical stability of PCASF was evaluated using cyclic voltammetry (CV). An electrochemical analyzer (a BAS Inc. ALS model 600A) was used as the measuring device. The solution for the CV measurement was prepared by using dehydrated dimethylformamide (DMF) as a solvent, dissolving a supporting electrolyte of tetra-n-butylammonium perchlorate (n-Bu$_4$NClO$_4$) to a concentration of 100 mM, and dissolving PCASF, the object of measurement, to a concentration of 1 mM. A platinum electrode (a BAS Inc. PTE platinum electrode) was used as a working electrode, another platinum electrode (a BAS Inc. Pt counter electrode (5 cm) for VC-3) was used as an auxiliary electrode, and an Ag/Ag$^+$ electrode (a BAS Inc. RE5 non-aqueous solvent reference electrode) was used as a reference electrode. The scanning speed was set at 0.1 V per second, and a 100 cycle measurement was conducted.

Figure 20:
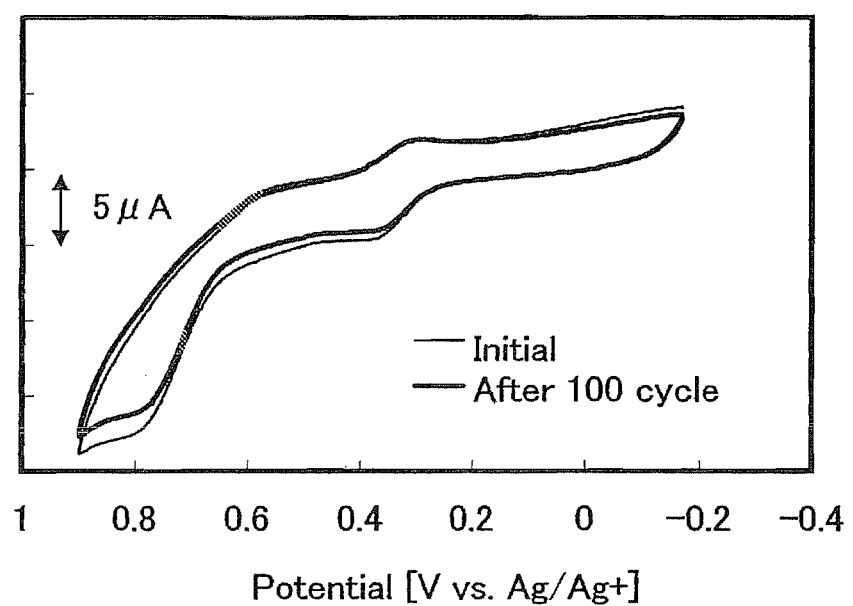
FIG. 20 shows a CV chart of PCASF.

Results of the CV measurement for the oxidation side of PCASF film are shown in FIG. 20. The graph which shows the measurement results shows a reversible peak, there being almost no change in the cyclic voltammogram even when oxidation is repeated 100 times. This means that PCASF has tolerance to the cycle of oxidation and reduction which follows the oxidation, and that it is electrochemically stable.

Embodiment 3

In this example, a method of synthesis of 2-{N-[4-(N-carbazolyl)phenyl]N-phenylamino}-spiro-9,9'-bifluorene (abbrev.: YGASF), which is expressed by the Structural Formula 66 in Embodiment Mode 1, will be explained.

YGASF can be synthesized by conducting a coupling reaction with 2-bromo-spiro-9,9'-bifluorene, which is expressed by Formula 111 below, and 9-[4-(N-phenylamino) phenyl]carbazole (abbrev.: YGA), which is expressed by Formula 114 below, using a metal catalyst. Note that the method of synthesis of 2-bromo-spiro-9,9'-bifluorene was explained in Step 1 of Example 1, so it will not be explained here.

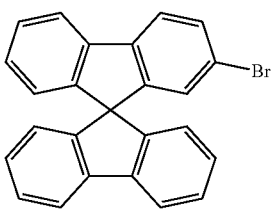

(111)

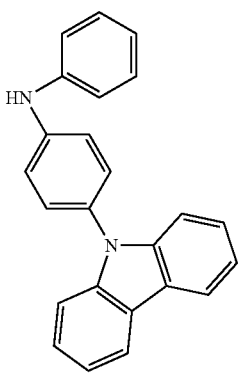

(114)

Step 1

A method of synthesis of YGA will be explained.

56.3 g (0.24 mol) of 1,4-dibromobenzene, 31.3 g (0.18 mol) of carbazole, 4.6 g (0.024 mol) of copper iodide, 66.3 g (0.48 mol) of potassium carbonate, and 2.1 g (0.008 mol) of 18-crown-6-ether were placed in a 300 mL three-necked flask, and nitrogen substitution was carried out. 8 mL of DMPU was added, and the mixture was stirred for 6 hours at 180° C. After cooling the reaction mixture to room temperature, the precipitate was removed by suction filtration. The filtrate was washed with dilute hydrochloric acid, a saturated sodium hydrogen carbonate solution, and a saturated saline solution, in that order, then dried with magnesium sulfate. After drying, the reaction mixture was filtered naturally, the filtrate was concentrated, and the oily substance obtained was purified by silica gel column chromatography (hexane:ethyl acetate=9:1). After recrystallization from chloroform and hexane, 20.7 g of light brown plate-shaped crystals were obtained, in a yield of 35%. By a nuclear magnetic resonance method (NMR), it was ascertained that these light brown plate-shaped crystals were N-(4-bromophenyl)carbazole.

Next, $^1$H NMR of the compound obtained will be shown.

$^1$H NMR (300 M Hz, DMSO-d$_6$) δ ppm: 8.14 (d, J=7.8 Hz, 2H), 7.73 (d, J=8.7 Hz, 2H), 7.46 (d, J=8.4 Hz, 2H), 7.42-7.26 (m, 6H)

A synthesis scheme (f-1) of N-(4-bromophenyl)carbazole will be shown next.

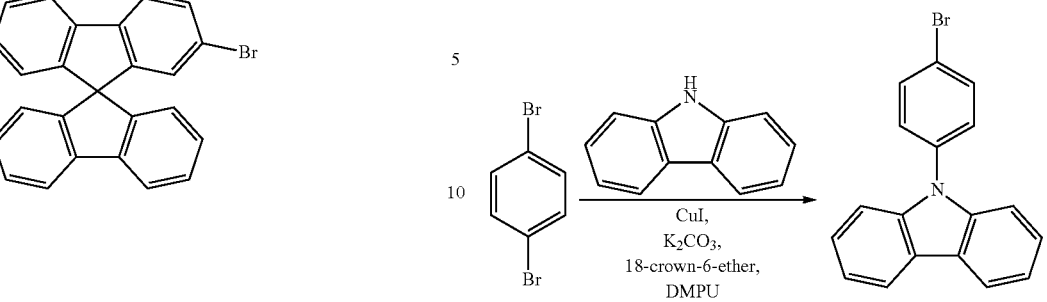

(f-1)

5.4 g (17.0 mmol) of N-(4-bromophenyl)carbazole, 1.8 mL (20.0 mmol) of aniline, 100 mg (0.17 mmol) of bis(dibenzylideneacetone)palladium(0) (abbrev.: Pd(dba)$_2$), and 3.9 g (40 mmol) of sodium-tert-butoxide (abbrev.: tert-BuONa) were put in a 200 mL three-necked flask, and nitrogen substitution was conducted. 0.1 mL of tri-tert-butylphosphine (abbrev.: P(tert-Bu)$_3$) and 50 mL of toluene were added, and the mixture was stirred for 6 hours at 80° C. The reaction mixture was filtered through Florisil, Celite and alumina. The filtrate was washed with water and a saturated saline solution, then dried with magnesium sulfate. The reaction mixture was filtered naturally. The filtrate was concentrated, and the oily product obtained was purified by silica gel column chromatography (hexane:ethyl acetate=9:1), giving 4.1 g of the target product, in a yield of 73%. It was confirmed that this compound was YGA by a nuclear magnetic resonance method (NMR).

Figure 21A:
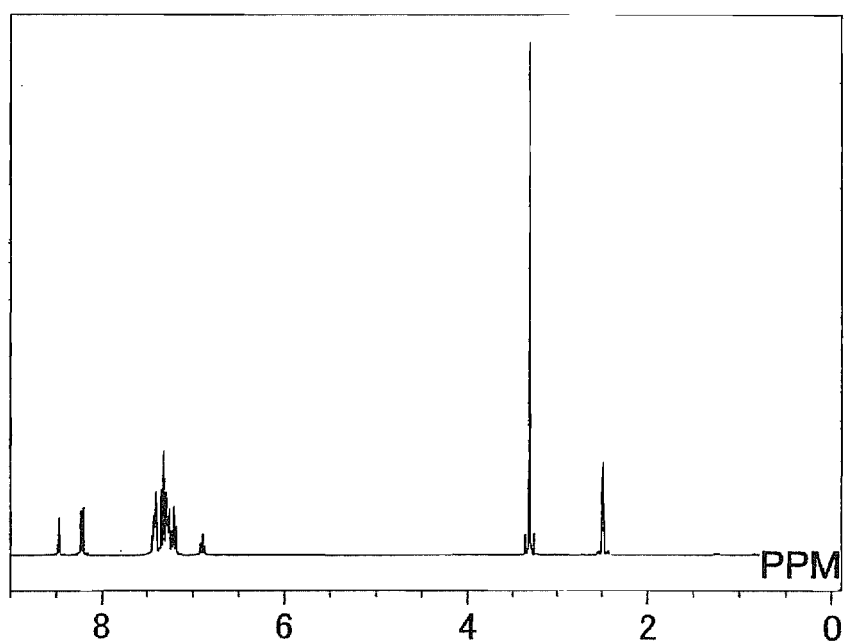
FIGS. 21A and 21B are $^1$H NMR charts of YGA.
Figure 21B:
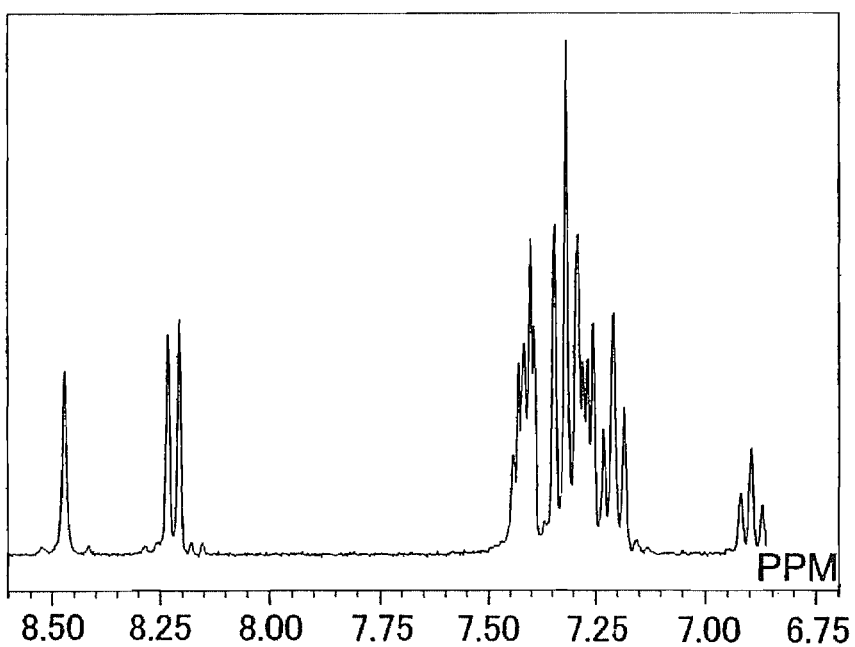

$^1$H NMR of the compound which was obtained will be shown next. Also, $^1$H NMR charts are shown in FIGS. 21A and 21B. Note that the chart in FIG. 21B shows an enlarged version of the 6.7 ppm to 8.6 ppm range of FIG. 21A.

$^1$H NMR (300 MHz, DMSO-ds) δ ppm: 8.47 (s, 1H), 8.22 (d, J=7.8 Hz, 2H), 7.44-7.16 (m, 14H), 6.92-6.87 (m, 1H)

Next, a synthesis scheme (f-2) of YGA is shown.

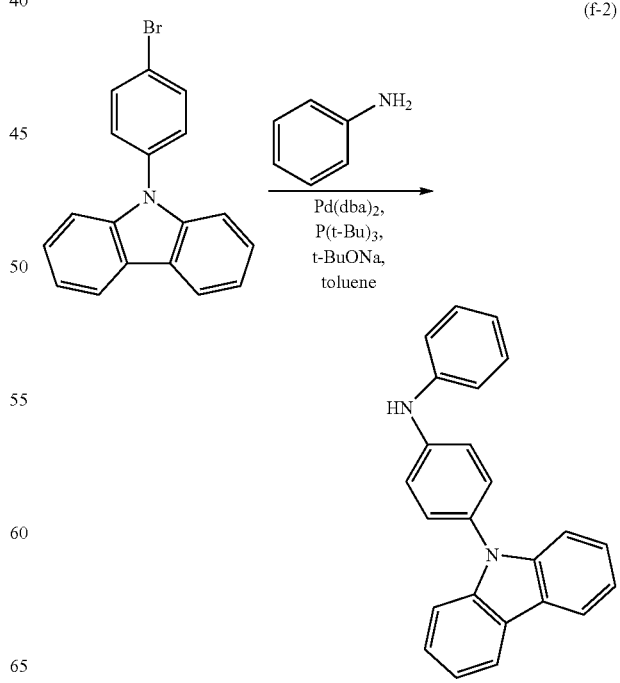

(f-2)

Step 2

Synthesis of YGASF 2.0 g (5.1 mmol) of 2-bromo-spiro-9,9'-bifluorene, 1.7 mg (5.1 mmol) of YGA, 30.4 mg (0.05 mmol) of bis(dibenzylideneacetone)palladium(0), and 2.0 g (21 mmol) of t-butoxysodium were put in a 100 mL three-necked flask, and nitrogen substitution was carried out. 30 mL of toluene was added, and the mixture was degassed at reduced pressure. 0.1 mL of tri(t-butyl)phosphine (10 wt % hexane solution) was added, and the mixture was stirred for 6 hours at 80° C. After the reaction, the mixture was filtered through Celite. The filtrate was washed 3 times with water and once with a saturated saline solution, and dried with magnesium sulfate. The reaction mixture was filtered naturally, the filtrate was concentrated, and an oily product was obtained. This oily product was purified by silica gel column chromatography (hexane:toluene=7:3). After recrystallization from chloroform and hexane, a white powdered solid was obtained, weighing 2.9 g in a yield of 88%. It was confirmed that this white powdered solid was YGASF by a nuclear magnetic resonance method (NMR).

Figure 22:
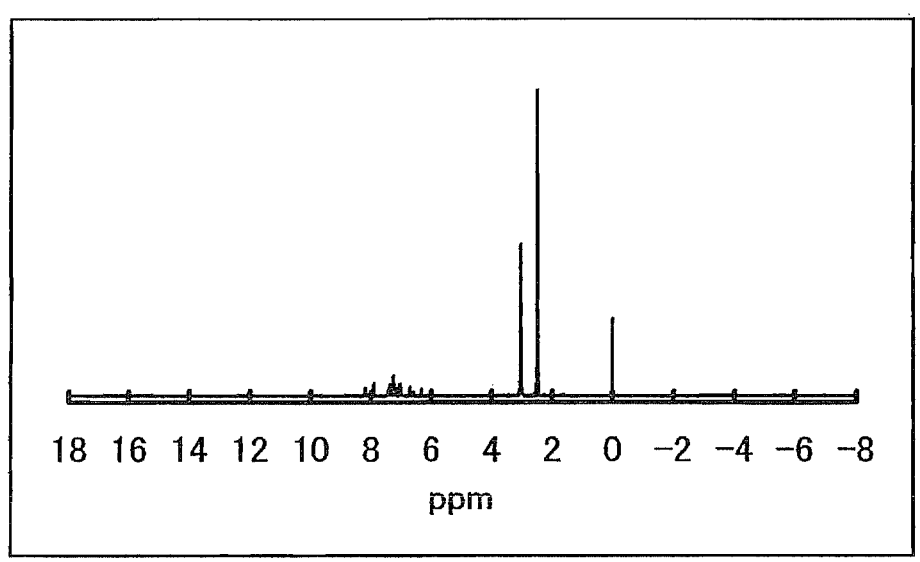
FIG. 22 is a $^1$H NMR chart of YGASF.

$^1$H NMR of the compound which was obtained is shown below. In addition, a $^1$H NMR chart is shown in FIG. 22.

1H NMR (300 MHz, DMSO-d$_6$); δ=8.19 (d, J=7.80 Hz, 2H), 7.97-7.91 (m, 4H), 7.43-7.01 (m, 22H), 6.71 (d, J=7.80 Hz, 2H), 6.71 (d, J=7.80 Hz, 2H), 6.58 (d, J=6.9 Hz, 1H) 6.32 (d, J=2.10 Hz, 1H)

Next, a synthesis scheme (g-1) of YGASF will be shown.

(g-1)

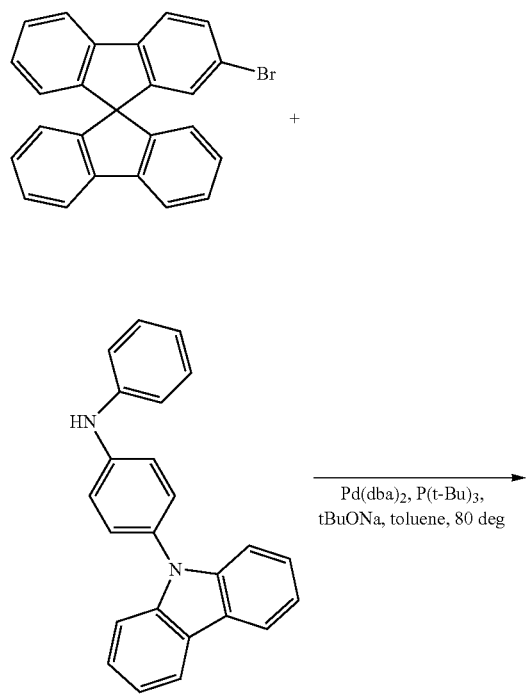

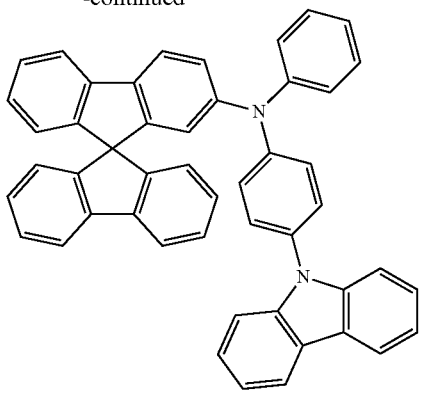

Sublimation purification was conducted for 24 hours on 2.50 g of the YGASF obtained, at a pressure of 6.7 Pa and a temperature of 300° C. 2.4 g was recovered, in a yield of 96%.

Further, the decomposition temperature (Td) of the YGASF was measured with a thermo-gravimetric/differential thermal analyzer (a Seiko Instruments Inc. TG/DTA320). It was found to be 371° C. Thus, it was found that YGASF shows a high Td.

Figure 23:
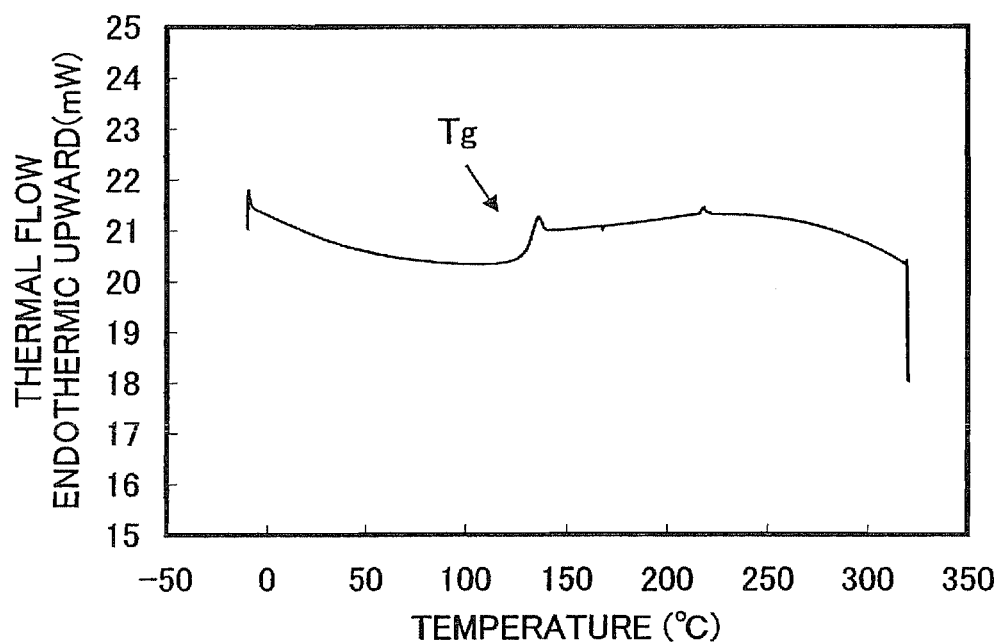
FIG. 23 is a DSC chart of YGASF.

Further, the glass transition temperature (Tg) was measured using a differential scanning calorimeter (a Perkin Elmer Co., Ltd Pyris 1 DSC). First, a sample was heated from −10° C. to 320° C. by 40° C. per minute and melted. Then it was cooled to −10° C. by 40° C. per minute. Next, by raising the temperature to 320° C. by 10° C. per minute, the DSC chart in FIG. 23 was obtained. From this chart, it was found that the glass transition temperature (Tg) of YGASF was 129° C. Thus, it was found that YGASF has a high glass transition temperature. Further, the endothermic peak on the DSC chart of when the sample was first melted was observed. It shows the melting point, which was 296° C.

Figure 24:
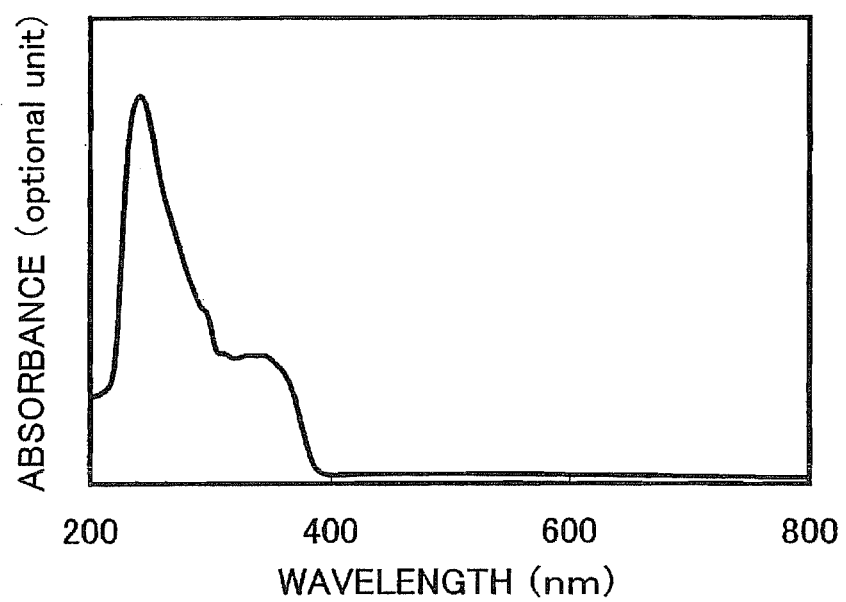
FIG. 24 shows an absorption spectrum of a thin film of YGASF.
Figure 25:
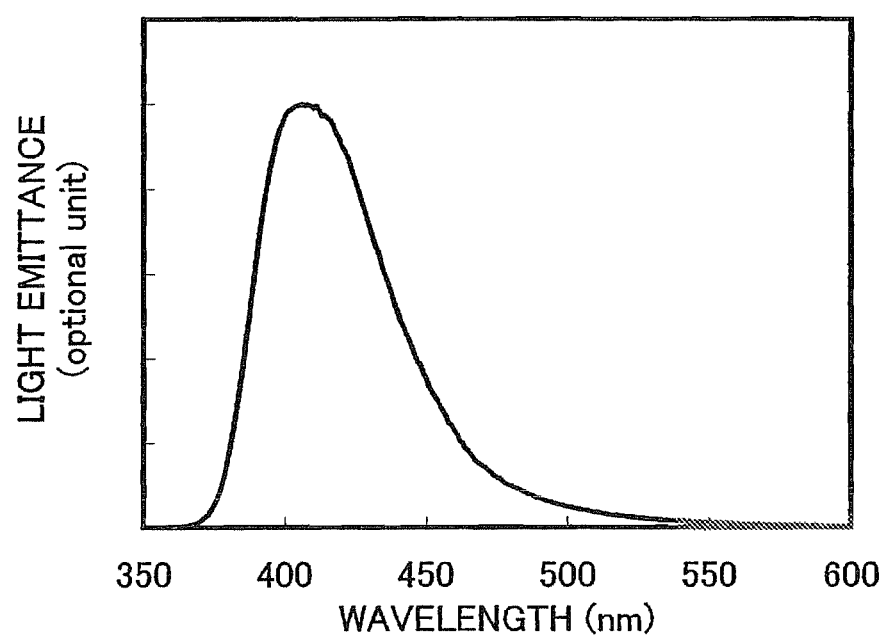
FIG. 25 shows a light emission spectrum of a thin film of YGASF.

The absorption spectrum and emission spectrum of YGASF in a thin film state are shown in FIGS. 24 and 25. It was found that in a thin film state, YGASF had a maximum absorption wavelength of 242 nm, and a maximum emission wavelength of 406 nm. Using the absorption spectrum data from FIG. 24, the absorption edge was obtained from a Tauc plot. Using the energy of that absorption edge as an energy gap, the energy gap of YGASF was found to be 3.3 eV. 9,10-diphenylanthracene, which exhibits representative blue emission, has an energy gap of 2.9 eV, so it was found that YGASF has an amply large energy gap. Further, the HOMO level in a thin film state was measured with an ambient photoelectron spectroscopy (using a Riken Keiki Co., Ltd AC-2), and was found to be −5.3 eV. The LUMO level was obtained using the HOMO level and the energy gap, and was −2.0 eV.

Further, the electrochemical stability of YGASF was evaluated using cyclic voltammetry (CV). An electrochemical analyzer (a BAS Inc. ALS model 600A) was used as the measuring device. A solution for the CV measurement was prepared by using dehydrated dimethylformamide (DMF) as a solvent, dissolving a supporting electrolyte of tetra-n-butylammonium perchlorate (n-Bu$_4$NClO$_4$) to a concentration of 100 mM, and dissolving YGASF, the object of measurement, to a concentration of 1 mM. A platinum electrode (a BAS Inc. PTE platinum electrode) was used as a working electrode, another platinum electrode (a BAS Inc. Pt counter electrode (5 cm) for VC-3) was used as an auxiliary electrode, and an Ag/Ag⁺ electrode (a BAS Inc. RE5 non-aqueous solvents reference electrode) was used as a reference electrode. The scanning speed was set at 0.1 V per second, and a 100 cycle measurement was conducted.

Figure 26:
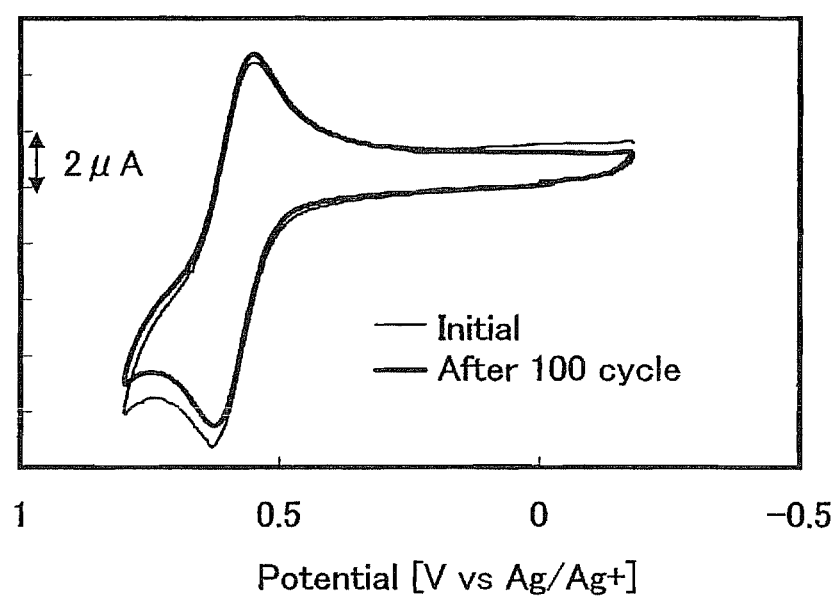
FIG. 26 is a CV chart of YGASF.

CV measurement results for the oxidation side of YGASF film are shown in FIG. 26. The graph showing the measurement results shows a reversible peak, there being almost no change in the cyclic voltammogram even when oxidation is repeated 100 times. This means that YGASF has tolerance to the cycle of oxidation and reduction which follows the oxidation, and that it is electrochemically stable.

Embodiment 4

In this example, a method of synthesis of 2,7-bis[N-(diphenylaminophenyl)-N-phenylamino]-spiro-9,9'-bifluorene (abbrev.: DPA2SF), which is expressed by Structural Formula 26 in Embodiment Mode 1, will be explained.

DPA2SF can be synthesized by conducting a coupling reaction with 2,7-dibromo-spiro-9,9'-bifluorene, which is expressed by Formula 115 below, and DPA, which is expressed by Formula 112 below, using a metal catalyst. Note that the method of synthesis of DPA was explained in Step 2 of Example 1, so it will not be explained here. Step 2 of Example 1 should be referred to.

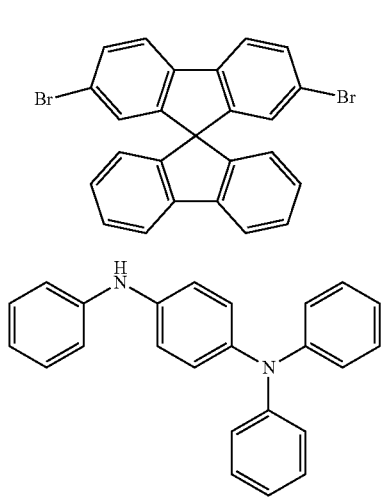

(115)

(112)

Step 1

Synthesis of 2,7-dibromo-spiro-9,9'-bifluorene 7.2 g (40.0 mmol) of 9-fluorenone, 14.2 g (44.0 mmol) of iodobenzene diacetate, 60 mL of glacial acetic acid, and 60 mL of acetic anhydride were put in a 300 mL conical flask. In addition, 2.1 mL (41.2 mmol) of bromine and one drop of sulfuric acid were added, and the mixture was stirred for 1 hour at room temperature. After the reaction, the precipitates were filtered. The precipitates were recrystallized with ethanol, and 9.2 g of 2,7-dibromo-9-fluorenone, a yellow solid, was obtained in a yield of 68%.

A synthesis scheme (h-1) of 2,7-dibromo-9-fluorenone is shown below.

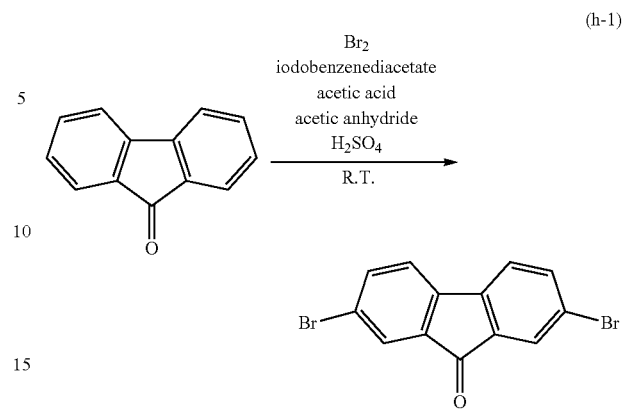

(h-1)

1.26 g (51.9 mmol) of magnesium was put in a 50 mL three-necked flask, and was stirred while a vacuum was drawn by a rotary pump. After returning the air to atmospheric pressure, 5 mL of diethyl ether and 1 drop of dibromoethane were added. Further, 8.3 mL (50 mmol) of 2-bromobiphenyl dissolved in 15 mL of diethyl ether was added dropwise, and the mixture was refluxed for 3 hours at 50° C. to make a Grignard reagent.

A manufacturing scheme (h-2) of the Grignard reagent is shown below.

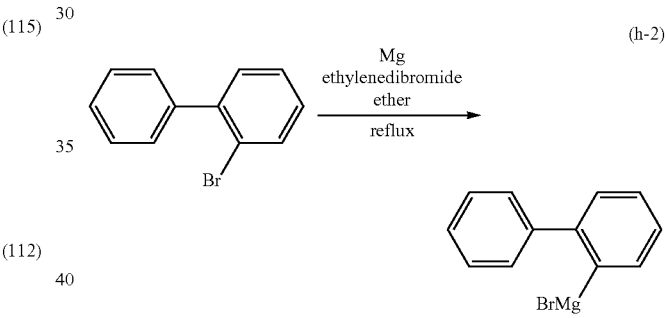

(h-2)

15.2 g (45 mmol) of 2,7-dibromo-9-fluorenone was put in a 100 mL three-necked flask, and nitrogen substitution was conducted. 40 mL of diethyl ether was added. The Grignard reagent above was transferred into a dropping funnel by a cannula so as not to expose it to the atmosphere, and was added dropwise into the mixture. The mixture was refluxed at 50° C. After the reaction, the solution was washed with water. Then the aqueous layer was extracted with ethyl acetate and combined with the organic layer. The layers were washed with a saturated saline solution, then dried with magnesium sulfate. Filtration and concentration were carried out, and 22 g of 9-(biphenyl-2-yl)-2,7-dibromo-9-fluorenol was obtained as a white solid, in a yield of 90%.

A synthesis scheme (h-3) of 9-(biphenyl-2-yl)-2,7-dibromo-9-fluorenol is shown below.

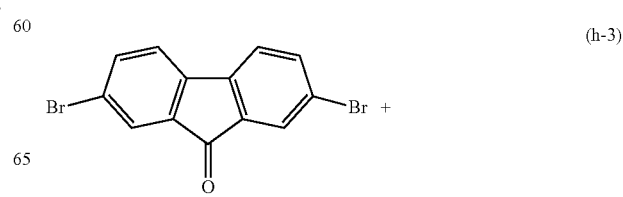

(h-3)

-continued

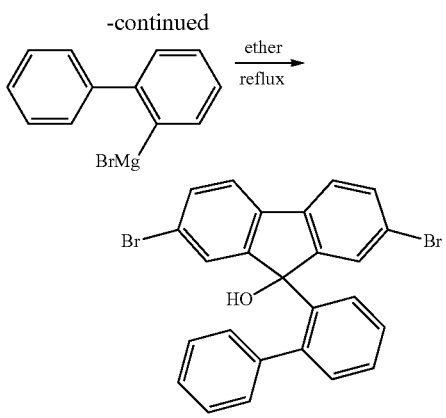

22 g (45.0 mmol) of 9-biphenyl-2-yl-2,7-dibromo-9-fluorenol, and 100 mL of glacial acetic acid were placed in a 300 mL three-necked flask, several drops of concentrated hydrochloric acid were added, and the mixture was refluxed. After the reaction, the precipitates were filtered. The precipitate was recrystallized with ethanol, and 12.3 g of 2,7-dibromo-spiro-9,9'-bifluorene was obtained as a white solid, in a yield of 57%.

A synthesis scheme (h-4) of 2,7-dibromo-9,9'-spiro-bifluorene is shown below.

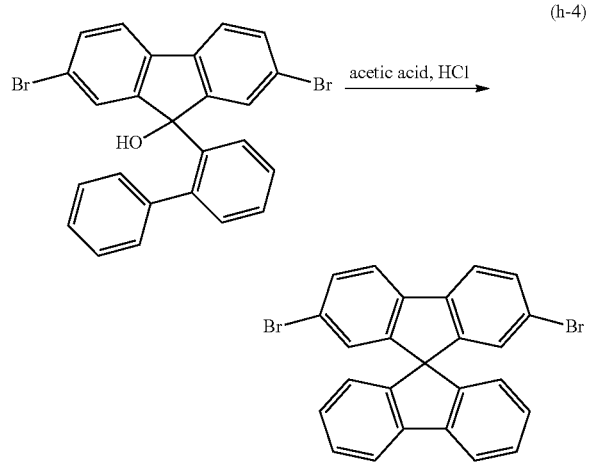

(h-4)

Step 2

Synthesis of DPA2SF 5.0 g (10.6 mmol) of 2, 7-dibromo-spiro-9,9'-bifluorene, 7.4 g (21.0 mmol) of DPA, 63 mg (0.1 mmol) of bis(dibenzylidencacetone)palladium(0), and 3.6 g (37 mmol) of t-butoxysodium were placed in a 300 mL three-necked flask, and nitrogen substitution was conducted. 100 mL of toluene was added to the mixture, and the mixture was degassed at reduced pressure. 0.05 mL of tri(t-butyl)phosphine (10 wt % hexane solution) was added, and the mixture was stirred for 6 hours at 80° C. After the reaction, the mixture was filtered through Celite. The filtrate was washed 3 times with water and once with a saturated saline solution, then dried with magnesium sulfate. The reaction mixture was naturally filtered, and the filtrate was concentrated to obtain an oily product. This oily product was purified by silica gel column chromatography (hexane:ethyl acetate=7:3), and recrystallized with chloroform and ethanol, giving 6.0 g of a pale yellow powdered solid in a yield of 57%. It was confirmed that this pale yellow powdered solid was DPA2SF by a nuclear magnetic resonance method (NMR).

Figure 27:
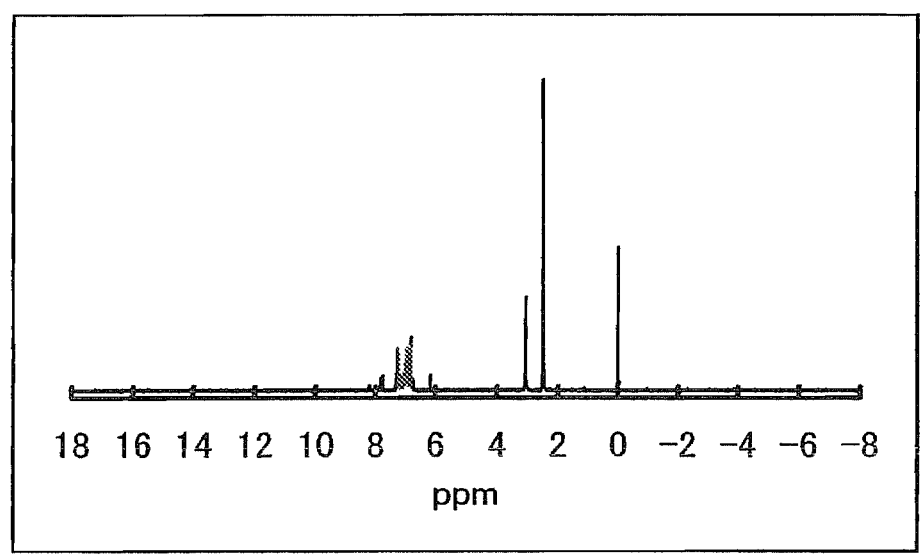
FIG. 27 is a 1H NMR chart of DPA2SF.

$^1$H NMR of the compound obtained is shown below. Also, a $^1$H NMR chart is shown in FIG. 27.

$^1$H NMR (300 MHz, DMSO-d$_6$); δ=7.84 (d, J=7.21 Hz, 2H), 7.77 (d, J=7.80 Hz, 2H), 7.32-7.79 (m, 40H), 6.73 (d, J=7.80 Hz, 2H), 6.16 (d, J=2.10 Hz, 2H)

A synthesis scheme (i-1) of DPA2SF is shown below.

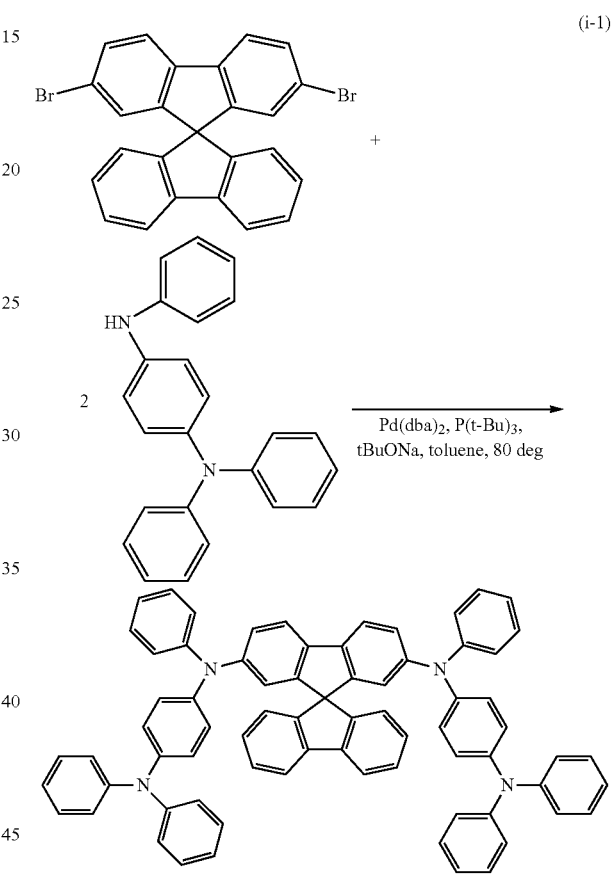

(i-1)

Sublimation purification was conducted on 2.0 g of the DPA2SF for 24 hours at a pressure of 6.7 Pa and a temperature of 350° C. 1.3 g was recovered, in a yield of 66%.

Further, the decomposition temperature (Td) of the DPA2SF was measured with a thermo-gravimetric/differential thermal analyzer (a Seiko Instruments Inc. TG/DTA320), and was found to be 436° C. Thus, it was found that DPA2SF shows excellent heat resistance.

Figure 28:
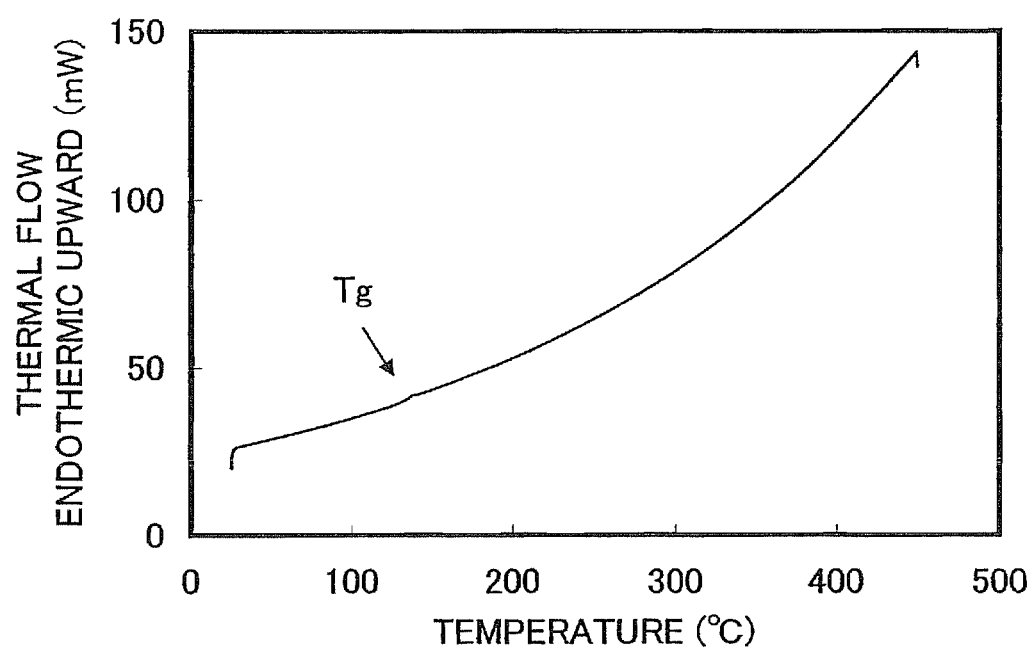
FIG. 28 is a DSC chart of DPA2SF.

In addition, the glass transition temperature (Tg) was measured using a differential scanning calorimeter (a Perkin-Elmer Co., Ltd Pyris 1 DSC). First, a sample was heated from 25° C. to 450° C. at 40° C. per minute. Next, it was cooled to 25° C., at 40° C. per minute. Then, by raising the temperature to 450° C. at 10° C. per minute, the DSC chart in FIG. 28 was obtained. From this chart, it was found that the glass transition temperature (Tg) of DPA2SF is 132° C. Thus, it was found that DPA2SF has a high glass transition temperature. Note that in this measurement, the endothermic peak, which shows the melting point, was not observed.

Figure 29:
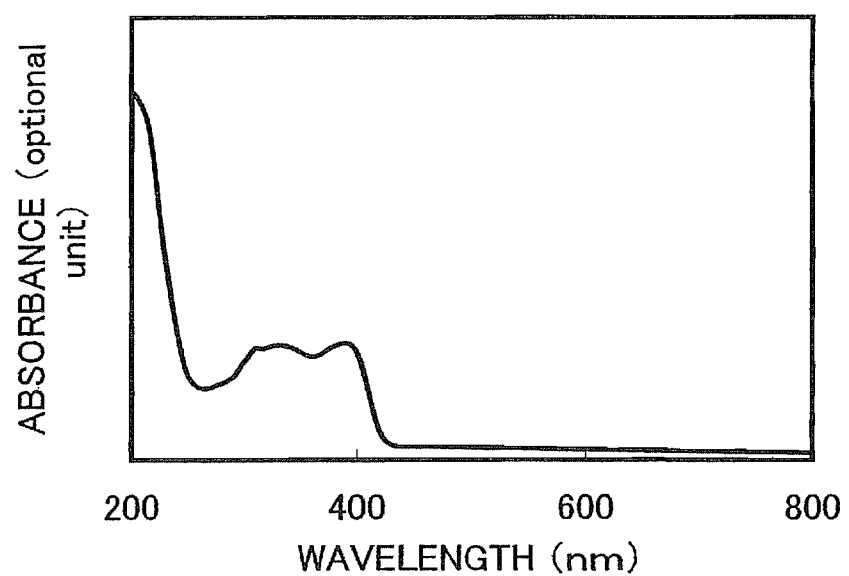
FIG. 29 shows an absorption spectrum of a thin film of DPA2SF.
Figure 30:
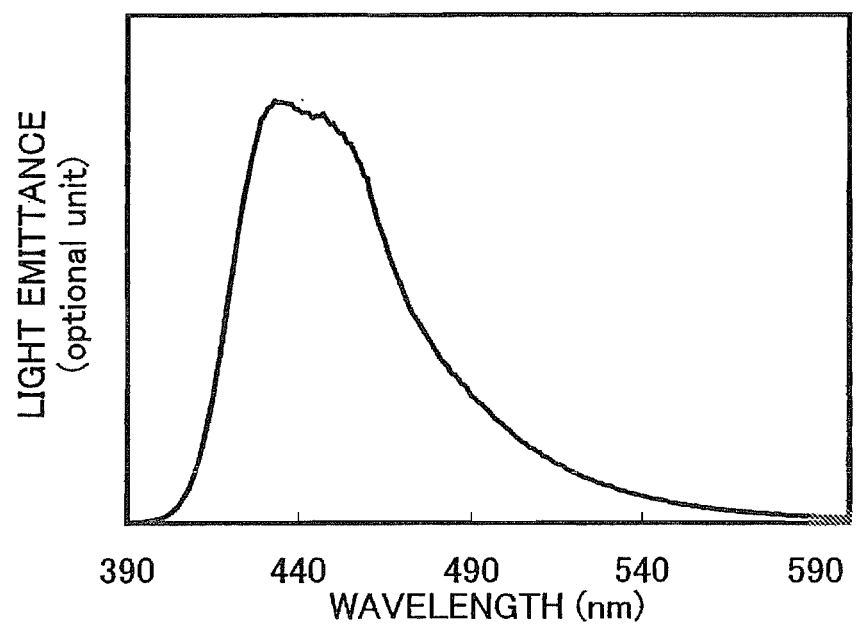
FIG. 30 shows a light emission spectrum of a thin film of DPA2SF.

The absorption spectrum and emission spectrum of DPA2SF in a thin film state are shown in FIGS. 29 and 30. It was found that in a thin film state, DPA2SF had a maximum absorption wavelength of 390 nm, and a maximum emission wavelength of 433 nm. Using the absorption spectrum data from FIG. 29, the absorption edge was obtained from a Tauc plot. Using the energy of that absorption edge as an energy gap, the energy gap of DPA2SF was found to be 3.0 eV. Since 9,10-diphenylanthracene, which exhibits representative blue emission, has an energy gap of 2.9 eV, it can be seen that DPA2SF has an amply large energy gap. Further, the HOMO level in a thin film state was measured by an ambient photoelectron spectroscopy (using a Riken Keiki Co., Ltd AC-2), and was found to be −5.1 eV. Using the HOMO level and the energy gap, the LUMO level was found to be −2.1 eV.

Further, the electrochemical stability of DPA2SF was evaluated using cyclic voltammetry (CV). An electrochemical analyzer (a BAS Inc. ALS model 600A) was used as the measuring device. A solution for the CV measurement was prepared by using dehydrated dimethylformamide (DMF) as a solvent, dissolving a supporting electrolyte of tetra-n-butylammonium perchlorate (n-$Bu_4NClO_4$) to a concentration of 100 mM, and dissolving DPA2SF, the object of measurement, to a concentration of 1 mM. A platinum electrode (a BAS Inc. PTE platinum electrode) was used as a working electrode, another platinum electrode (a BAS Inc. Pt counter electrode (5 cm) for VC-3) was used as an auxiliary electrode, and an Ag/$Ag^+$ electrode (a BAS Inc. RE5 non-aqueous solvent reference electrode) was used as a reference electrode. The scanning speed was set at 0.1 V per second, and a 100 cycle measurement was conducted.

Figure 31:
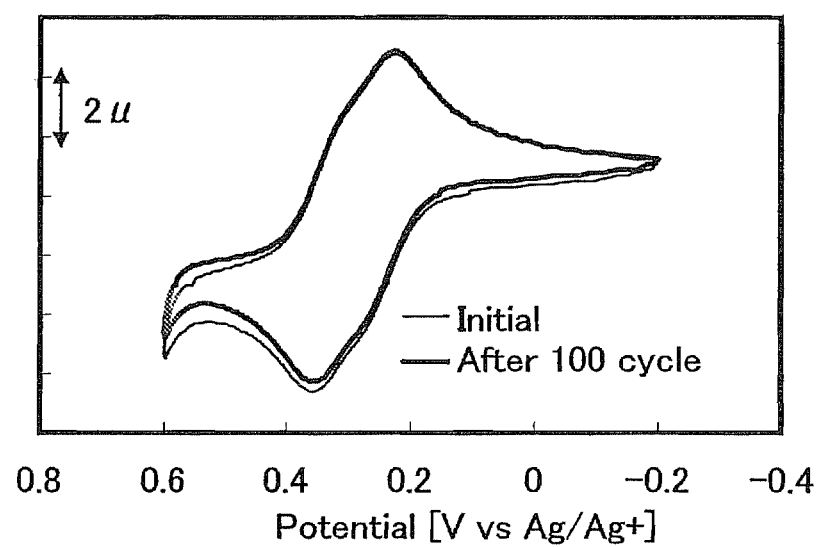
FIG. 31 is a CV chart of DPA2SF.

CV measurement results for the oxidation side of DPA2SF film are shown in FIG. 31. The graph which shows the measurement results shows a reversible peak, there being almost no change in the cyclic voltammogram even when oxidation is repeated 100 times. This means that DPA2SF has tolerance to the cycle of oxidation and reduction which follows the oxidation, and that it is electrochemically stable.

Embodiment 5

In this example, a manufacturing method of a light-emitting element using DPASF for a hole transporting layer will be explained. Characteristics of such a light-emitting element will also be explained.

A light-emitting element was formed over a glass substrate. Over the glass substrate, a 110 nm ITSO film was formed as a first electrode. The aforementioned ITSO film was formed by a sputtering method. Note that in the present invention, the shape of the first electrode was set at 2 mm×2 mm. Next, as pre-treatment for forming a light-emitting element over the first electrode, a surface of the substrate was washed with a porous resin (typically, a resin made of PVA (polyvinyl alcohol), nylon or the like), heat treatment was carried out for 1 hour at 200° C., and UV ozone treatment was conducted for 370 seconds.

Next, a 40 nm co-evaporation film of NPB and molybdenum oxide (MoOx) was formed as a hole injecting layer (NPB:MoOx=4:2). Then, a 20 nm film of DPASF was formed as a hole transporting layer. Over this stack of films, a 40 nm co-evaporation film of t-BuDNA and 1,1,4,4-tetraphenyl-1,3-butadiene (TBP) was formed as a light-emitting layer. The weight ratio of t-BuDNA and TBP was set at 1:0.01. In addition, a 20 nm film of Alq was formed as an electron transporting layer, and a 1 nm film of calcium fluoride ($CaF_2$) was formed as an electron injecting layer. Lastly, a 200 nm film of Al was formed as a second electrode, thereby completing the element. Note that the layers from the hole injecting layer to the second electrode were all formed by a vacuum deposition method using heat resistance.

Figure 32:
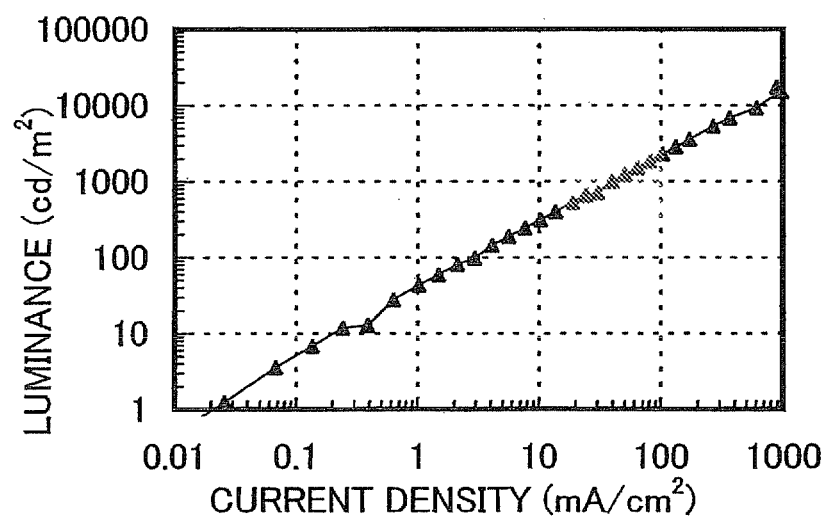
FIG. 32 shows a current density-luminance characteristic of a light-emitting element manufactured in Example 5.
Figure 33:
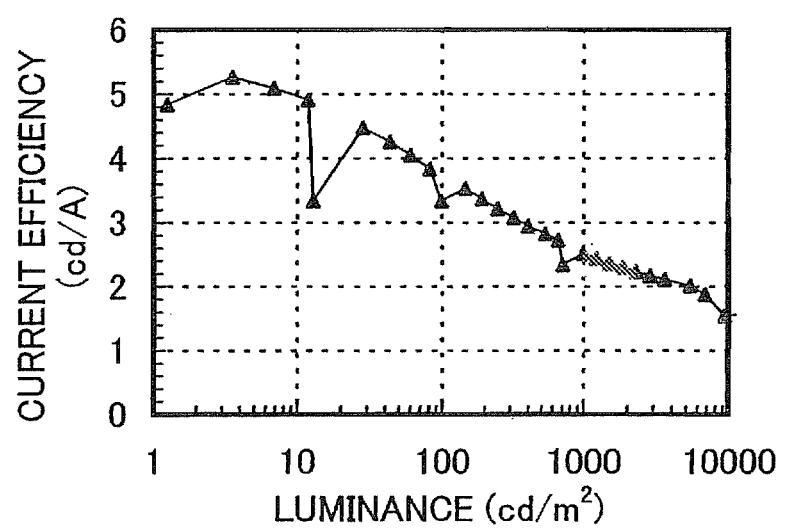
FIG. 33 shows a luminance-current efficiency characteristic of a light-emitting element manufactured in Example 5.
Figure 34:
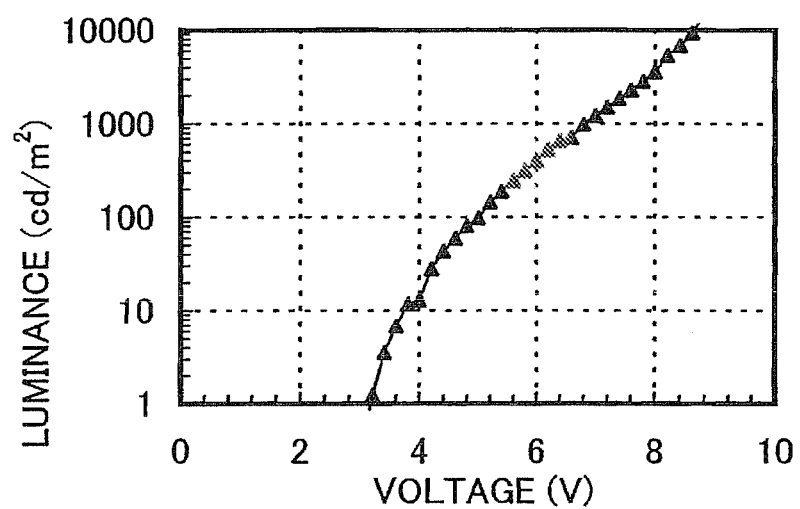
FIG. 34 shows a voltage-luminance characteristic of a light-emitting element manufactured in Example 5.

Current density-luminance characteristics, luminance-current efficiency characteristics and voltage-luminance characteristics of the element manufactured are shown in FIG. 32, FIG. 33 and FIG. 34, respectively. It can be seen that the light-emitting element using a spirofluorene derivative of the present invention exhibits excellent characteristics. In addition, since the light-emitting element manufactured uses the spirofluorene derivative of the present invention, which has a high Tg, it has high heat resistance.

Embodiment 6

In this example, a manufacturing method of a light-emitting element using YGASF for a hole transporting layer, and characteristics of such a light-emitting element, will be explained.

A light-emitting element was formed over a glass substrate. Over the glass substrate, a 110 am film of ITSO was formed as a first electrode. This ITSO film was formed by a sputtering method. Note that in the present invention, the first electrode had a shape of 2 mm×2 mm. Next, as pretreatment for forming a light-emitting element over the first electrode, a surface of the substrate was washed with a porous resin (typically, a resin made of PVA (polyvinyl alcohol), nylon, or the like), heat treatment was conducted for 1 hour at 200° C., and UV ozone treatment was conducted for 370 seconds.

Next, a 40 nm co-evaporation film of NPB and molybdenum oxide (MoOx) was formed as a hole injecting layer (NPB:MoOx=4:2). Then, a 20 nm film of YGASF was formed as a hole transporting layer. Over this stack of films, a 40 nm co-evaporation film of t-BuDNA and 2,5,8,11-tetra(tert-butyl)perylene (TBP) was formed as a light-emitting layer. The weight ratio of t-BuDNA and TBP was set at 1.0.01. In addition, a 20 nm film of Alq was formed as an electron transporting layer, and a 1 m film of calcium fluoride ($CaF_2$) was formed as an electron injecting layer. Lastly, a 200 nm film of Al was formed as a second electrode, and the element was thereby completed. Note that the films from the hole injecting layer to the second electrode were all formed by a vacuum deposition method using heat resistance.

Figure 35:
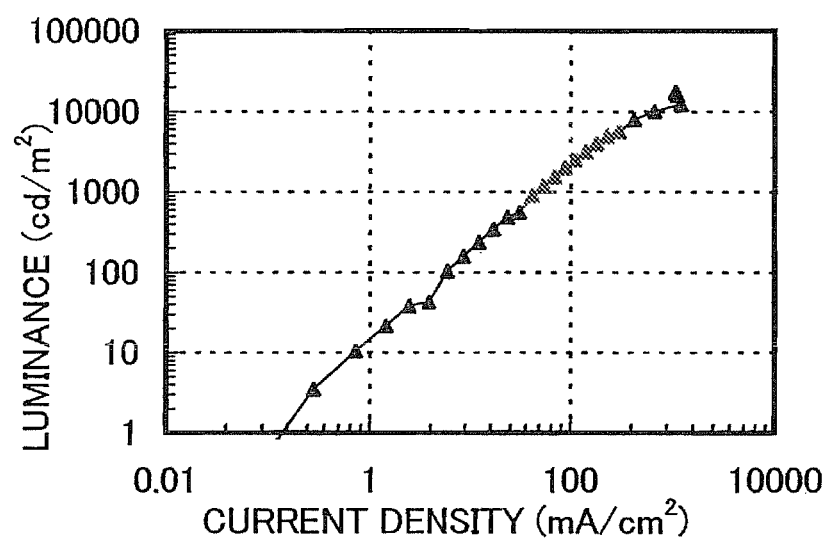
FIG. 35 shows a current density-luminance characteristic of a light-emitting element manufactured in Example 6.
Figure 36:
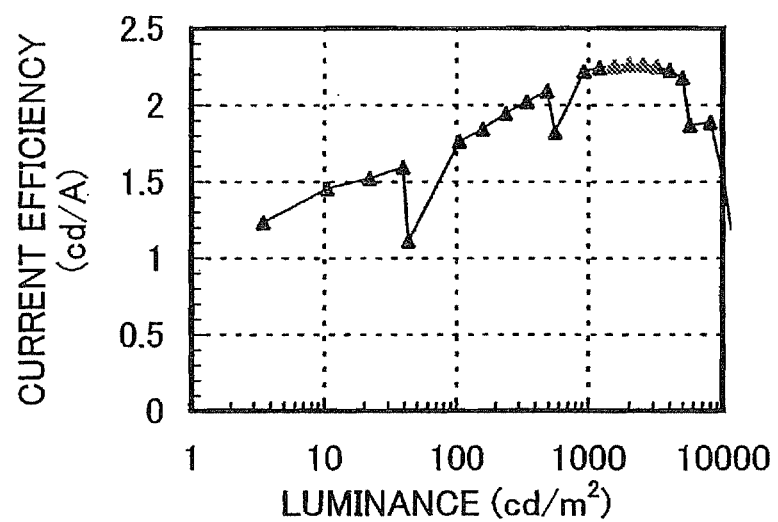
FIG. 36 shows a luminance-current efficiency characteristic of a light-emitting element manufactured in Example 6.
Figure 37:
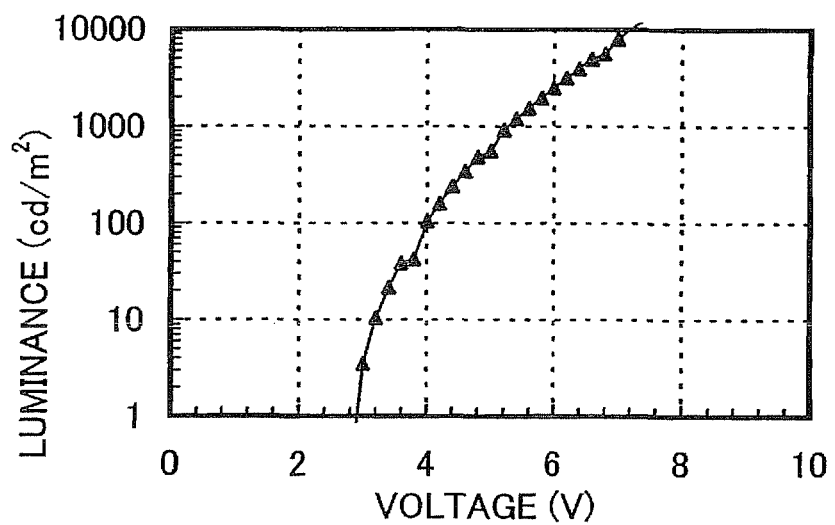
FIG. 37 shows a voltage-luminance characteristic of a light-emitting element manufactured in Example 6.

Current density-luminance characteristics, luminance-current efficiency characteristics and voltage-luminance characteristics of the element manufactured are shown in FIG. 35, FIG. 36 and FIG. 37, respectively. It can be seen that a light-emitting element using the spirofluorene derivative of the present invention exhibits excellent characteristics. Further, in particular, the element of the present example using YGASF for a hole transporting layer has excellent voltage-luminance characteristics. Furthermore, since the light-emitting element manufactured uses the spirofluorene derivative of the present invention, which has a high glass transition temperature (Tg), it has high heat resistance.

Embodiment 7

In this example, a manufacturing method of a light-emitting element using PCASF for a hole transporting layer, and characteristics of such a light-emitting element, will be explained.

A light-emitting element was formed over a glass substrate. Over the glass substrate, a film of ITSO was formed with a thickness of 110 nm as a first electrode. The ITSO film was formed by a sputtering method. Note that in the present invention, the first electrode had a shape of 2 mm×2 mm. Next, as pretreatment for forming a light-emitting element over the first electrode, a surface of the substrate was washed by a porous resin (typically, a resin made of PVA (polyvinyl alcohol), nylon, or the like), heat treatment was conducted for 1 hour at 200° C., and UV ozone treatment was conducted for 370 seconds.

Next, a 40 nm co-evaporation film of NPB and molybdenum oxide (MoOx) was formed as a hole injecting layer (NPB:MoOx=4:2). Then, a 20 nm film of PCASF was formed as a hole transporting layer. Over this stack of films, a 40 nm co-evaporation film of t-BuDNA and TBP was formed as a light-emitting layer. The weight ratio of t-BuDNA and TBP was set at 1.0.01. In addition, a 20 nm film of Alq was formed as an electron transporting layer and a 1 nm film of calcium fluoride ($CaF_2$) was formed as an electron injecting layer. Lastly, a 200 nm film of Al was formed as a second electrode, completing the element. Note that the films from the hole injecting layer to the second electrode were all formed by a vacuum deposition method using heat resistance.

Figure 38:
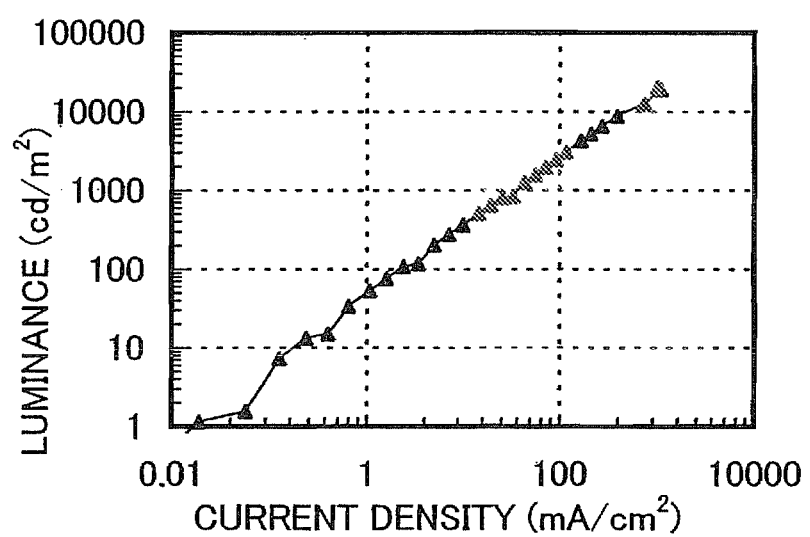
FIG. 38 shows a current density-luminance characteristic of a light-emitting element manufactured in Example 7.
Figure 39:
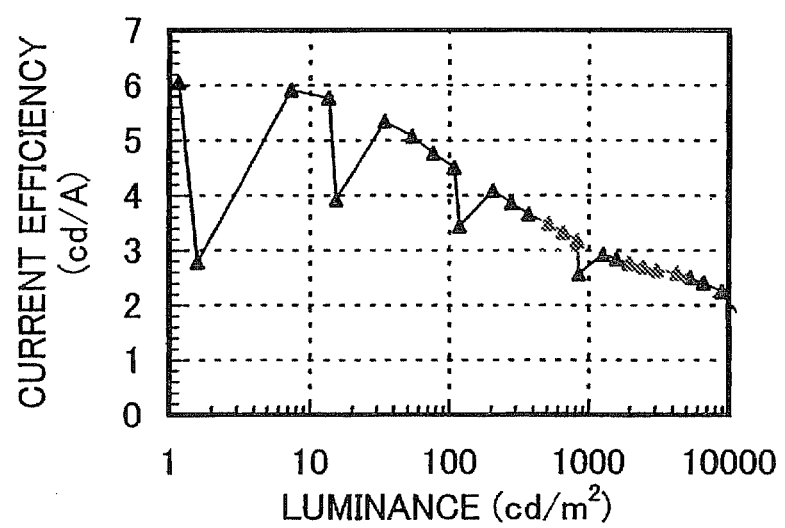
FIG. 39 shows a luminance-current efficiency characteristic of a light-emitting element manufactured in Example 7.
Figure 40:
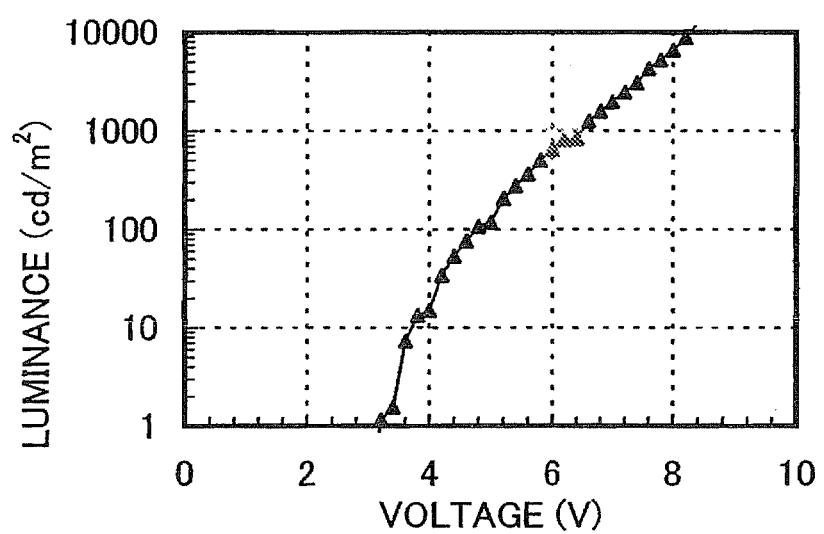
FIG. 40 shows a voltage-luminance characteristic of a light-emitting element manufactured in Example 7.

The current density-luminance characteristics, luminance-current efficiency characteristics and voltage-luminance characteristics of the element manufactured are shown in FIG. 38, FIG. 39 and FIG. 40, respectively. It can be seen that a light-emitting element using the spirofluorene derivative of the present invention exhibits excellent characteristics. Further, since the light-emitting element manufactured uses the spirofluorene derivative of the present invention, which has a high glass transition temperature (Tg), it has high heat resistance.

Embodiment 8

In this example, a composite material containing DPASF and molybdenum oxide (MoOx) and a manufacturing method of a light-emitting element using the composite material for a hole injecting layer will be explained. Also, characteristics of the light emitting element will be explained.

Figure 41:
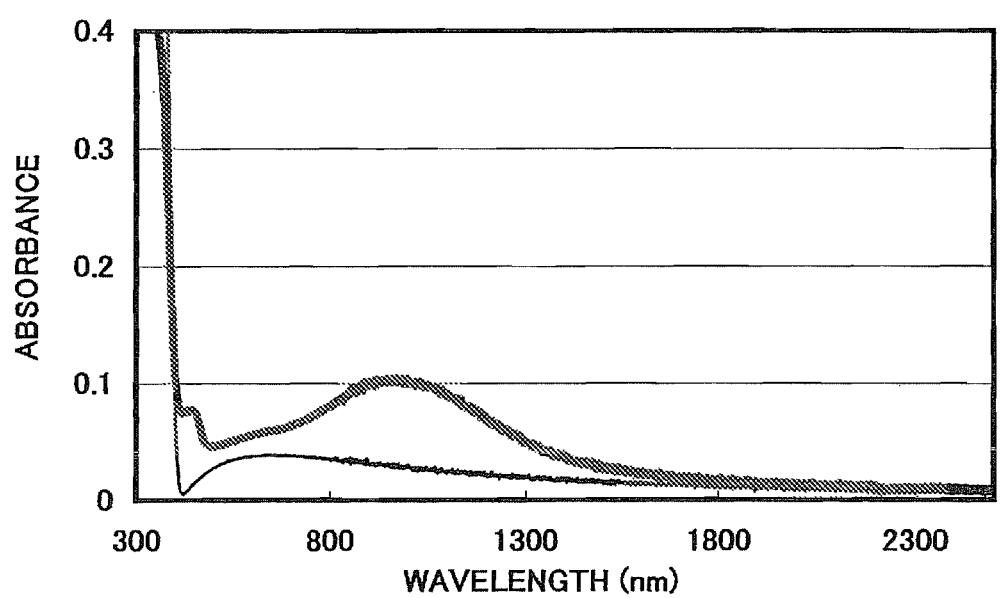
FIG. 41 shows absorption spectra of a thin film of DPASF and a thin film of a composite material of DPASF and a molybdenum oxide.

An absorption spectrum of a thin film of DPASF and an absorption spectrum of a thin film of the composite material containing DPASF and molybdenum oxide are shown in FIG. 41. Note that in FIG. 41, the thick line shows the spectrum of the composite material, and the thin line shows the spectrum of DPASF only. From FIG. 41, it can be seen that the shape of the DPASF-only absorption spectrum is different from the shape of the absorption spectrum of the composite material. It is thought that the difference in the absorption spectrums is not something that can also be explained from an absorption spectrum of molybdenum oxide only. It is thought that the difference showed due to DPASF interacting with molybdenum oxide. It is thought that the interaction is the giving and receiving of electrons between DPASF and molybdenum oxide. As a result of the giving and receiving of electrons, the carrier density inside the composite material increases, and thereby, beneficial effects can be obtained. For example, a hole injecting property is improved. Also, even when a film is thickened, a rise in driving voltage is small.

A light-emitting element was formed over a glass substrate. Over the glass substrate, a 110 nm film of ITSO was formed as a first electrode. The ITSO was formed by a sputtering method. Note that in the present invention, the shape of the first electrode was 2 mm×2 mm. Next, as pretreatment for forming a light-emitting element over the first electrode, a surface of the substrate was washed with a porous resin (typically a resin made of PVA (polyvinyl alcohol), nylon, or the like), heat treatment was conducted for 1 hour at 200° C., and UV ozone treatment was conducted for 370 seconds.

Next, a 50 nm co-evaporation film of DPASF and molybdenum oxide (MoOx) was formed as a hole injecting layer (DPASF:MoOx=4:1). Then, a 10 nm film of NPB was formed as a hole transporting layer. Over this stack of films, a 40 nm co-evaporation film of $Alq_3$ and coumarin 6 was formed as a light-emitting layer. The weight ratio of $Alq_3$ and coumarin 6 was set at 1:0.01. In addition, a 10 nm film of Alq was formed as an electron transporting layer, and a 30 nm co-evaporation film of $Alq_3$ and lithium was formed as an electron injecting layer. The weight ratio of $Alq_3$ and lithium was set at 1:0.01. Lastly, a 200 nm film of Al was formed as a second electrode, thereby completing the element. Note that the films from the hole injecting 6 layer to the second electrode were all formed by a vacuum deposition method using heat resistance. As a raw material for molybdenum oxide, molybdenum oxide (VI) was used.

Figure 42:
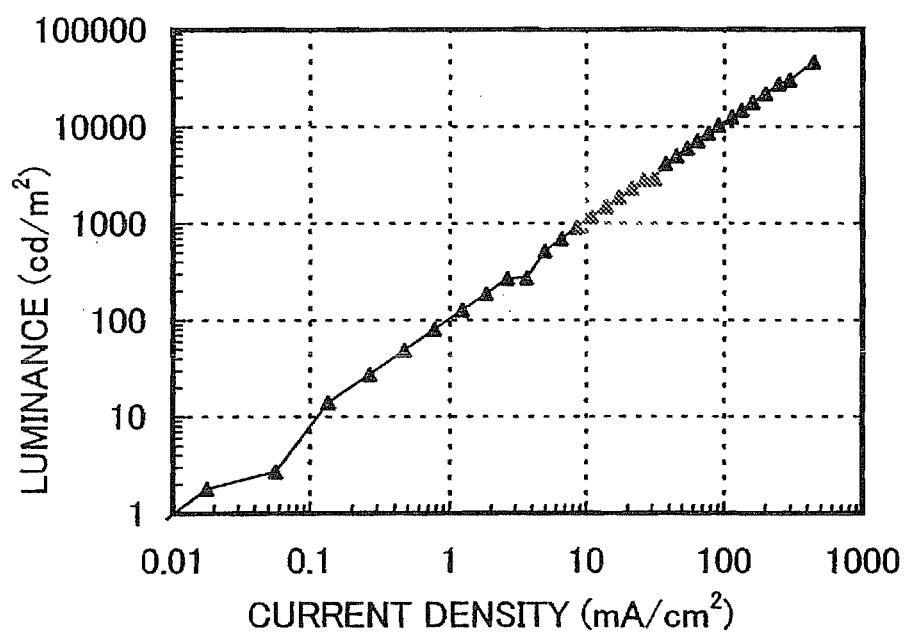
FIG. 42 shows a current density-luminance characteristic of a light-emitting element manufactured in Example 8.
Figure 43:
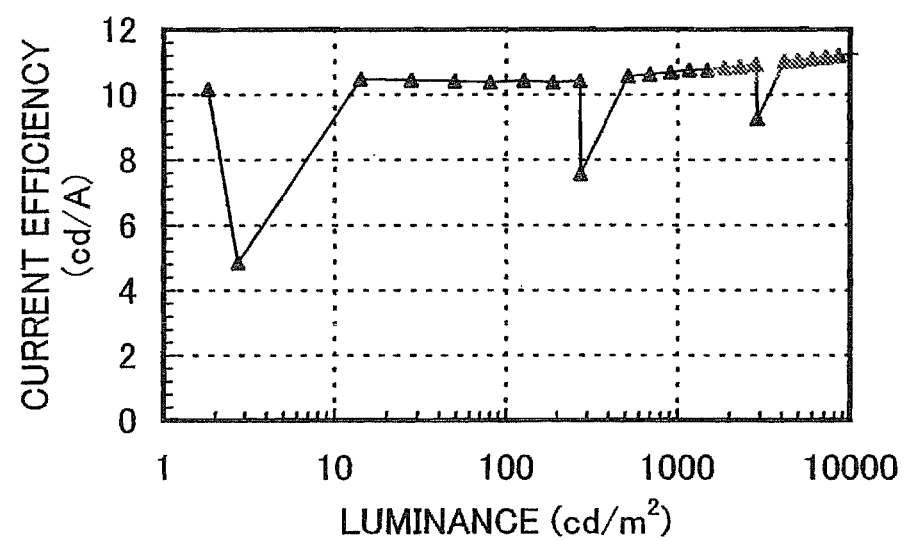
FIG. 43 shows a luminance-current efficiency characteristic of a light-emitting element manufactured in Example 8.
Figure 44:
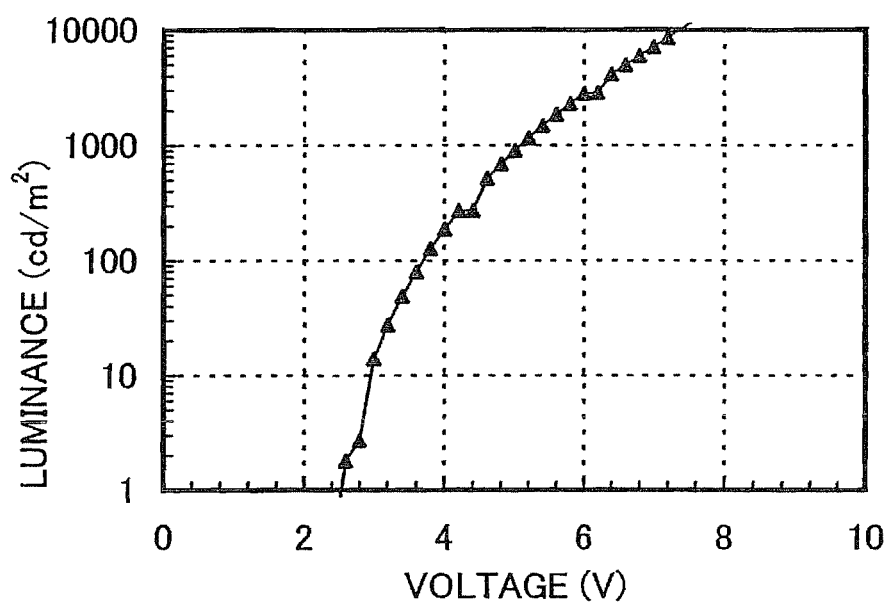
FIG. 44 shows a voltage-luminance characteristic of a light-emitting element manufactured in Example 8.

Current density-luminance characteristics, luminance-current efficiency characteristics and voltage-luminance characteristics of the element manufactured are shown in FIG. 42, FIG. 43 and FIG. 44, respectively. It can be seen that a light-emitting element using a composite material containing a spirofluorene derivative of the present invention and a metal oxide exhibits excellent characteristics. Further, since the light-emitting element manufactured uses the spirofluorene derivative of the present invention, which has a high glass transition temperature (Tg), it has high heat resistance.

Embodiment 9

In this example, a composite material containing DPA2SF and molybdenum oxide, and a manufacturing method of a light-emitting element using the composite material as a hole injecting layer, will be explained. Characteristics of the light emitting element will also be explained.

Figure 45:
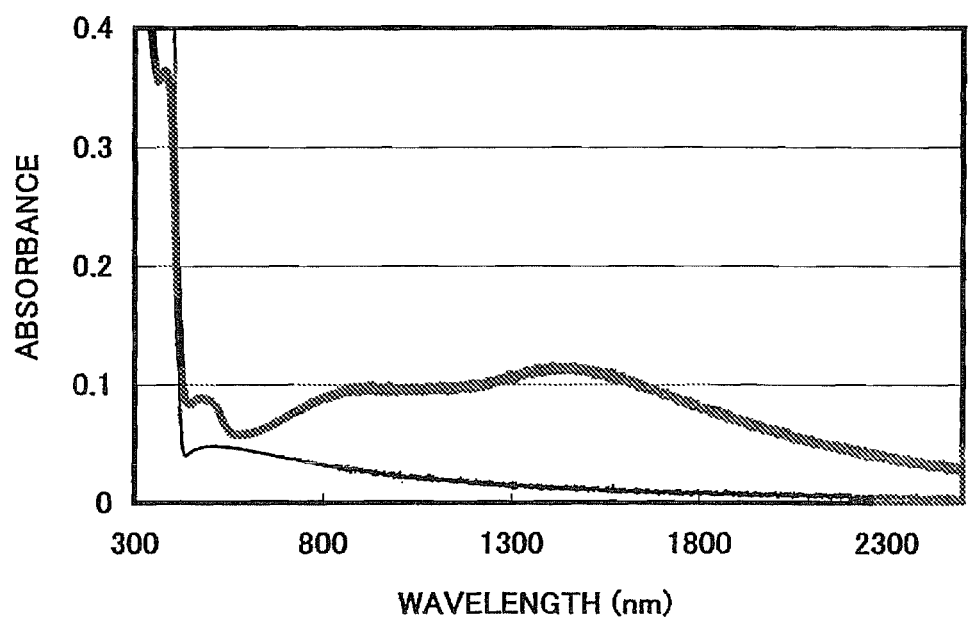
FIG. 45 shows absorption spectra of a thin film of DPA2SF and a thin film of a composite material of DPA2SF and a molybdenum oxide.

An absorption spectrum of DPA2SF and an absorption spectrum of the composite material containing DPA2SF and molybdenum oxide (MoOx) are shown in FIG. 45. Note that in FIG. 45, the thick line shows the spectrum of the composite material, and the thin line shows the spectrum of DPA2SF only. From FIG. 45, it can be seen that the shape of the DPA2SF-only absorption spectrum is different from the shape of the absorption spectrum of the composite material. It is thought that the difference in the absorption spectrums is not something that can also be explained from an absorption spectrum of molybdenum oxide only. It is thought that the difference showed due to DPA2SF interacting with molybdenum oxide. It is thought that the interaction is the giving and receiving of electrons between DPA2SF and molybdenum oxide. As a result of the giving and receiving of electrons, the carrier density inside the composite material increases, so beneficial effects can be obtained. For example, a hole injecting property can be improved. Also, even when a film thickens, a rise in driving voltage is small.

A light-emitting element was formed over a glass substrate. Over the glass substrate, a 110 nm film of ITSO was formed as a first electrode. The ITSO was formed by a sputtering method. Note that in the present invention, the shape of the first electrode was 2 mm×2 mm. Next, as pretreatment for forming a light-emitting element over the first electrode, a surface of the substrate was washed with a porous resin (typically a resin made of PVA (polyvinyl alcohol), nylon, or the like), heat treatment was conducted for 1 hour at 200° C., and UV ozone treatment was conducted for 370 seconds.

Next, a 50 nm co-evaporation film of DPA2SF and molybdenum oxide (MoOx) was formed as a hole injecting layer (DPA2SF:MoOx=4:1). Then, a 10 nm film of NPB was formed as a hole transporting layer. Over this stack of films, a 40 nm co-evaporation film of $Alq_3$ and coumarin 6 was formed as a light-emitting layer. The weight ratio of $Alq_3$ and coumarin 6 was set at 1:0.01. In addition, a 10 nm film of Alq was formed as an electron transporting layer, and a 30 nm co-evaporation film of $Alq_3$ and lithium was formed as an electron injecting layer. The weight ratio of $Alq_3$ and lithium was set at 1:0.01. Lastly, a 200 nm film of Al was formed as a second electrode, thereby completing the element. Note that the films from the hole injecting layer to the second electrode were all formed by a vacuum deposition method using heat resistance.

Figure 46:
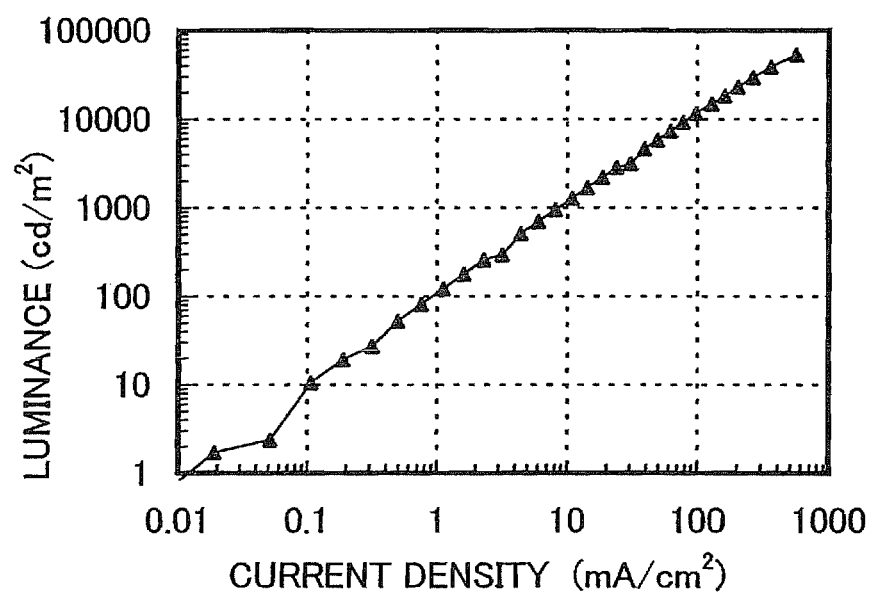
FIG. 46 shows a current density-luminance characteristic of a light-emitting element manufactured in Example 9.
Figure 47:
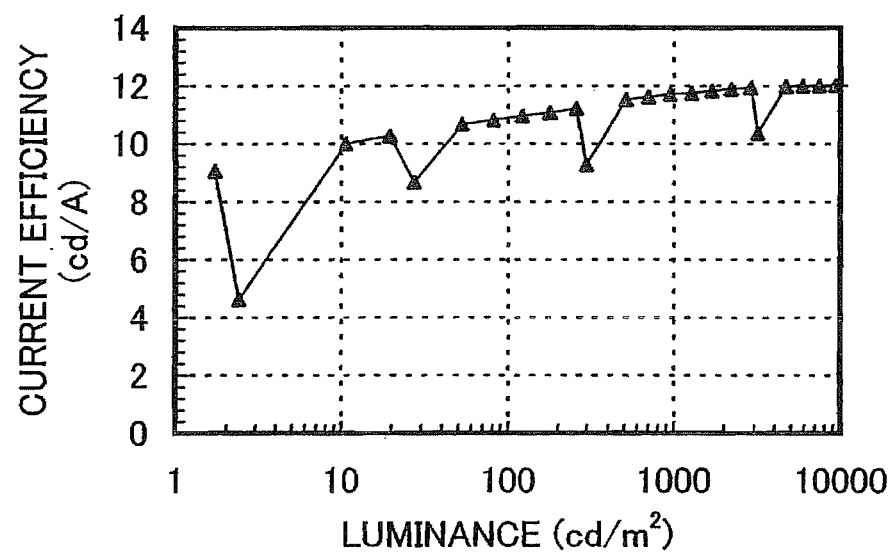
FIG. 47 shows a luminance-current efficiency characteristic of a light-emitting element manufactured in Example 9.
Figure 48:
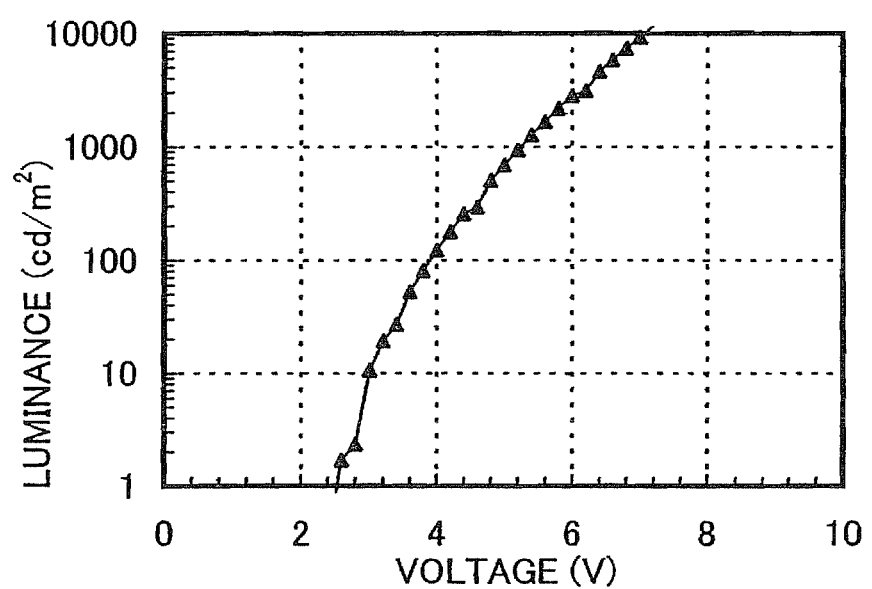
FIG. 48 shows a voltage-luminance characteristic of a light-emitting element manufactured in Example 9.

Current density-luminance characteristics, luminance-current efficiency characteristics and voltage-luminance characteristics of the element manufactured are shown in FIG. 46, FIG. 47 and FIG. 48, respectively. It can be seen that a light-emitting element using a composite material containing a spirofluorene derivative of the present invention and a metal oxide exhibits excellent characteristics. Further, since the light-emitting element manufactured uses the spirofluorene derivative of the present invention, which has a high glass transition temperature (Tg), it has high heat resistance.

Embodiment 10

In this example, a manufacturing method of a light-emitting element having a hole transporting layer formed of two layers, a layer of YGASF and a layer of NPB, is explained. Characteristics of such a light-emitting element are also explained.

A manufacturing method of a light-emitting element of this example will be explained using FIG. 1. A light-emitting element was formed over a glass substrate. Over the glass substrate, a 110 nm film of ITSO was formed as a first electrode 101. The ITSO was formed by a sputtering method, and the shape of the first electrode 101 was made 2 mm×2 mm by etching. Next, as pretreatment for forming a light-emitting element over the first electrode 101, a surface of the substrate was washed with a porous resin (typically a resin made of PVA (polyvinyl alcohol), nylon, or the like), heat treatment was conducted for 1 hour at 200° C., and UV ozone treatment was conducted for 370 seconds.

Next, a formation method of the organic layer 102 will be explained. First, a 50 nm co-evaporation film of NPB and molybdenum oxide was formed as a hole injecting layer. The film was formed with the mass ratio of NPB to molybdenum oxide set at 4:1. Next, a 10 nm film of NPB was formed as a first hole transporting layer. Over this stack of films, a 2 nm film of YGASF was formed as a second hole transporting layer, and a film of 9-[4-(N-carbazolyl)]phenyl-10-phenylanthracene (abbrev.: CzPA) and 9-(4-{N-[4-(9-carbazolyl)phenyl]-N-phenylamino}phenyl)-10-phenylanthracene (abbrev.: YGAPA) was formed as a light-emitting layer, with the mass ratio of CzPA to YGAPA at 1:0.04. In this film, CzPA functions as a host material, and YGAPA functions as a light-emission center material. The light-emitting layer was formed to be 30 nm thick. In addition, a 30 nm film of $Alq_3$ was formed as an electron transporting layer, and a 1 nm film of lithium fluoride was formed as an electron injecting layer. Next, a 200 nm film of Al was formed as a second electrode 103, completing the element. Finally, the element was sealed under a nitrogen atmosphere so that it would not be exposed to the atmosphere (the element of Example 10). Note that the films from the hole injecting layer to the second electrode were all formed by a vacuum deposition method using heat resistance.

As comparative examples, an element (Comparative Example 1 Element) having the same structure as the above element and having a second hole transporting layer formed of 4,4'-bis[N-(9,9-dimethylfluorene-2-yl)-N-phenylamino]biphenyl (abbrev.: DFLDPBi), and an element (Comparative Example 2 Element) having a first hole transporting layer only, and no second hole transporting layer, were manufactured.

Table 1 shows current efficiency, power efficiency, and the like for the element of Example 10, Comparative Example 1 Element, and Comparative Example 2 Element.

TABLE 1

|  | Energy Gap of 2nd Hole Transporting Layer (eV) | Current Efficiency (cd/A) | Power Efficiency (lm/W) |
| --- | --- | --- | --- |
| Embidiment 9 | 3.17 | 4.16 | 2.33 |
| Example 1 | 2.97 | 1.74 | 0.78 |
| Example 2 | — | 1.98 | 1.04 |

※ about 1000 cd

From Table 1 it can be seen that the element of Example 10 shows excellent values for both current efficiency and power efficiency, compared to the elements of the comparative examples.

It is thought that this is due to improvement in light-emitting efficiency. In the element of Example 10, the energy gap of the host material CzPA is 3.0 eV. This is close to the energy gap of the first hole transporting layer, NPB, which is 3.1 eV. By providing YGASF, which has a large energy gap of 3.3 eV, between CzPA and NPB, the transfer of excitation energy from the host CzPA to NPB is suppressed. Therefore, light-emitting efficiency is improved. As for Comparative Example 1 Element, which used DFLDPBi for a second hole transporting layer, it is thought that there were no improvement in its characteristics because DFLDPBi has an energy gap of 3.1 eV, which is the same as the energy gap of the first hole transporting layer, NPB.

Thus, the light-emitting element of this embodiment mode has high light-emitting efficiency. Further, due to improvement in light-emitting efficiency, the same luminance can be obtained with less current than when using conventional elements. Therefore, deterioration of a light-emitting element is suppressed, and the light-emitting element has better reliability. Furthermore, since power efficiency is also improved, the light-emitting element has low power consumption.

Note that in the structure of this embodiment mode, a spirofluorene derivative described in Embodiment Mode 1 may be used for the second hole transporting layer. However, it is necessary to select a material of the first hole transporting layer and the host material appropriately so that the energy gap of the second hole transporting layer is larger than that of the first hole transporting layer, and equal to or larger than that of the host material. Further, the thickness of the second hole transporting layer is 0.1 nm or more and less than 5 nm. Preferably it is 0.5 nm to 3 nm, more preferably, 1 nm to 2 nm.

Reference Example

Since the YGAPA and CzPA used in Example 10 are novel materials, synthesis methods thereof will be described below.

First, a method of synthesis of YGAPA, which is expressed by Structural Formula 116 below, will be explained.

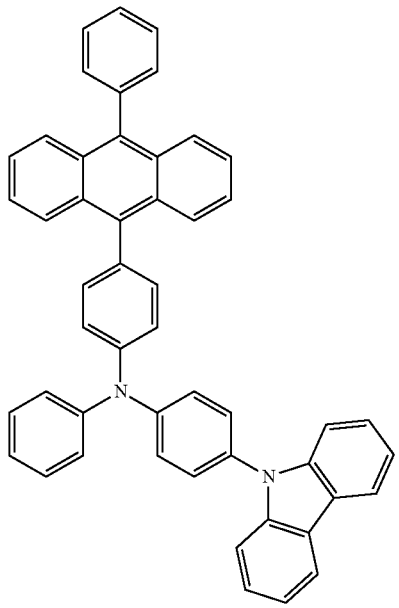

(116)

Step 1: Synthesis of 9-(4-bromophenyl)-10-phenylanthracene (abbrev.: PA (i) Synthesis of 9-phenylanthracene 5.4 g (21.1 mmol) of 9-bromoanthracene, 2.6 g (21.1 mmol) of phenylbromic acid, 60 mg (0.21 mmol) of Pd(OAc)$_2$, 10 ml (20 mmol) of a 2 mol/l potassium carbonate (K$_2$CO$_3$) aqueous solution, 263 mg (0.84 mmol) of tri(orthotolyl)phosphine (P(o-tolyl)$_3$), and 20 ml of 1,2-dimethoxyethane (abbrev.: DME) were mixed, and stirred for 9 hours at 80° C. After the reaction, the solid extracted was recovered by suction filtration. Then it was dissolved in toluene and filtered through Florisil, Celite, and alumina. After the filtrate was washed by water and a saturated saline solution, it was dried with magnesium sulfate. After natural filtration, the filtrate was concentrated, and the target substance of 9-phenylanthracene was obtained in a light brown solid form, weighing 21.5 g in a yield of 85% (synthesis scheme (j-3)).

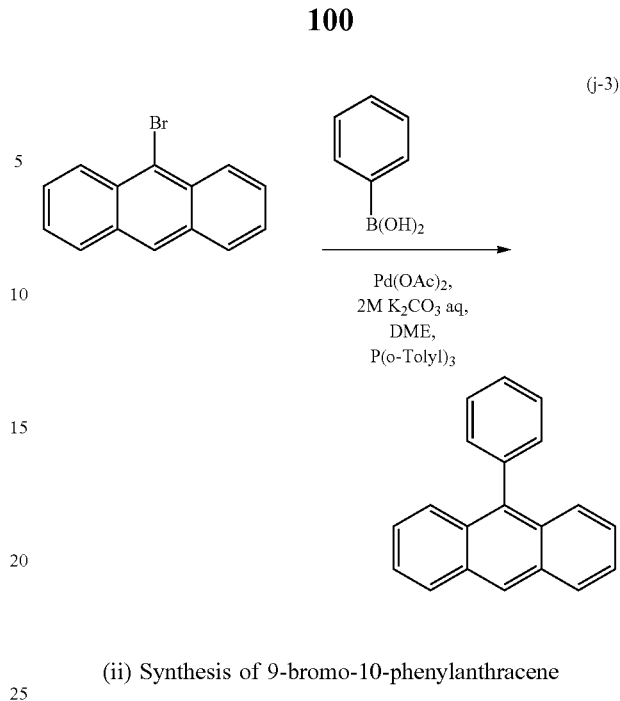

(j-3)

(ii) Synthesis of 9-bromo-10-phenylanthracene 6.0 g (23.7 mmol) of 9-phenylanthracene was dissolved in 80 ml of carbon tetrachloride. A solution of 3.80 g (21.1 mmol) of bromine dissolved in 10 ml of carbon tetrachloride was delivered dropwise into that reaction solution by a dropping funnel. After the dropping was complete, the mixture was stirred for 1 hour at room temperature. After the reaction, a sodium thiosulfate solution was added to stop the reaction. An organic layer was washed with a NaOH solution and a saturated saline solution, and dried with magnesium sulfate. After natural filtration, concentration and dissolving in toluene were conducted. Then, filtration was done through Florisil, Celite and alumina. The filtrate was concentrated, then recrystallized with dichloromethane and hexane. The target substance, 9-bromo-10-phenylanthracene, was obtained in the form of a pale yellow solid, weighing 7.0 g in a yield of 89% (synthesis scheme (j-4)).

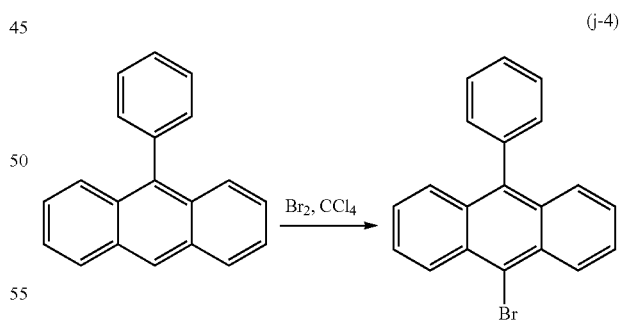

(j-4)

(iii) Synthesis of 9-iodo-10-phenylanthracene 3.33 g (10 mmol) of 9-bromo-10-phenylanthracene was dissolved in 80 ml of tetrahydrofuran (abbrev.: THF). After bringing the temperature to −78° C., 7.5 ml (12.0 mmol) of n-BuLi (1.6M) was added to the reaction solution dropwise with a dropping funnel, and the mixture was stirred for 1 hour. A solution of 5 g (20.0 mmol) of iodine dissolved in 20 ml of THF was added dropwise, and the mixture was stirred for another 2 hours at −78° C. After the reaction, a sodium thiosulfate solution was added and the reaction was stopped. The organic layer was washed with a sodium thiosulfate solution and a saturated saline solution, and dried with magnesium sulfate. After natural filtration, the filtrate was concentrated, and the solid obtained was recrystallized with ethanol. The target substance of 9-iodo-10-phenylanthracene was obtained as a pale yellow solid, weighing 3.1 g in a yield of 83% (synthesis scheme (j-5)).

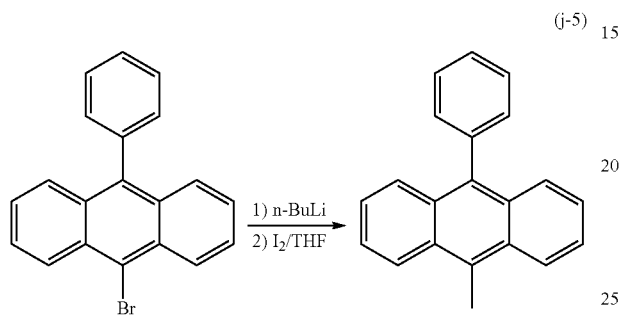

(j-5)

(iv) Synthesis of 9-(4-bromophenyl)-10-phenylanthracene (abbrev.: PA)

1.0 g (2.63 mmol) of 9-iodo-10-phenylanthracene, 542 mg (2.70 mmol) of p-bromophenylboronic acid, 46 mg (0.03 mmol) of Pd(PPh$_3$)$_4$, 3 ml (6 mmol) of 2 mol/L potassium carbonate (K$_2$CO$_3$) solution, and 10 ml of toluene were stirred for 9 hours at 80° C. After the reaction, toluene was added, and the mixture was filtered through Florisil, Celite, and alumina. The filtrate was washed with water and a saturated saline solution, then dried with magnesium sulfate. After natural filtration, the filtrate was concentrated, and recrystallized with chloroform and hexane. The target substance of 9-(4-bromophenyl)-10-phenylanthracene was obtained as a light brown solid, weighing 562 mg in a yield of 45% (synthesis scheme (j-6)).

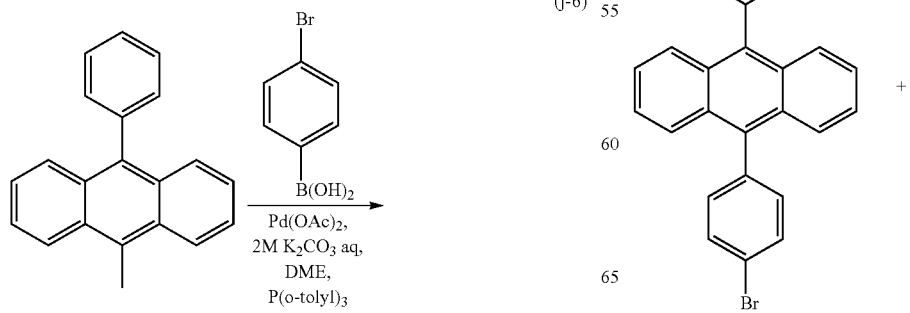

(j-6)

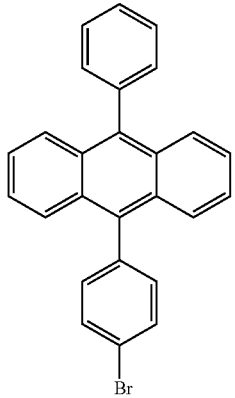

Figure 49A:
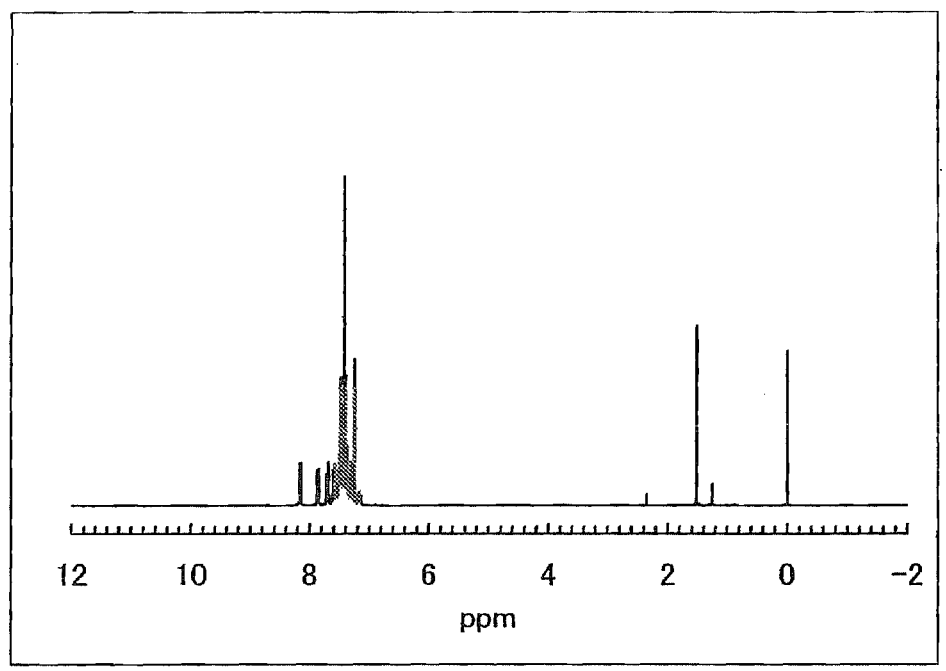
FIGS. 49A and 49B are $^1$H NMR charts of YGAPA.
Figure 49B:
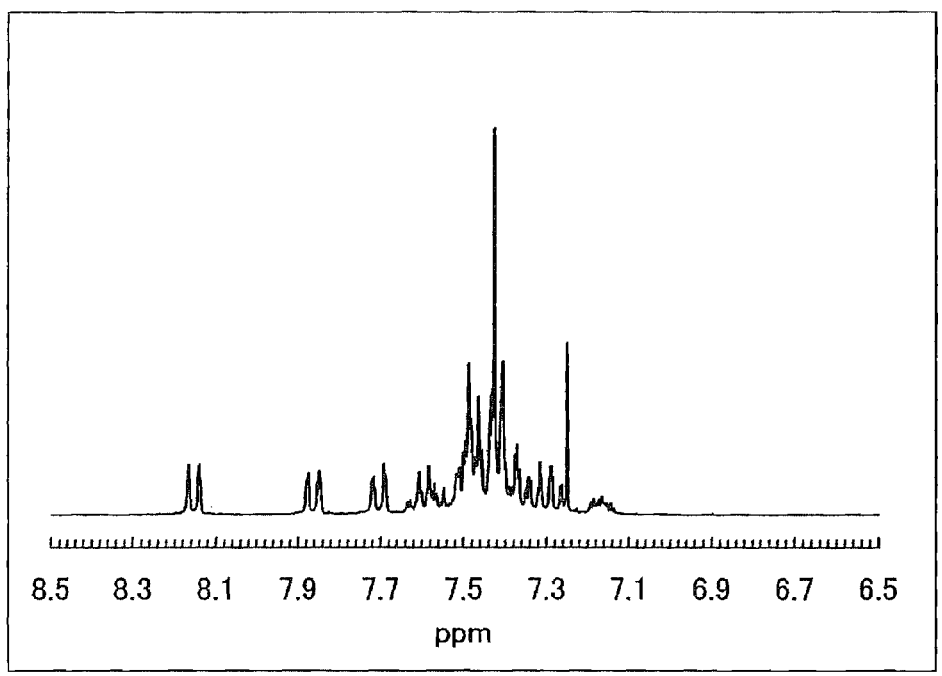

Step 2: Synthesis of YGAPA 409 mg (1.0 mmol) of 9-(4-bromophenyl)-10-phenylanthracene, 339 mg (1.0 mmol) of YGA (the manufacturing method of which was shown in Step 1 of Example 3), 6 mg (0.01 mmol) of Pd(dba)$_2$, 500 mg (5.2 mol) of tert-BuONa, 0.1 ml of P(tert-Bu)$_3$, and 10 ml of toluene were stirred for 4 hours at 80° C. After the reaction, the solution was washed with water. The aqueous layer was extracted with toluene and combined with the organic layer. The layers were washed with a saturated saline solution and dried with magnesium sulfate. After natural filtration and concentration, an oily product was obtained. The oily product was purified by silica gel column chromatography (hexane:toluene=7:3), then recrystallized with dichloromethane and hexane, giving 534 mg of the target product YGAPA as a yellow powdered substance, in a yield of 81% (synthesis scheme (j-7)). This compound was measured with a nuclear magnetic resonance method ($^1$H NMR), and confirmed to be YGAPA. A $^1$H NMR chart of the compound obtained is shown in FIGS. 49A and 49B.

A synthesis scheme of YGAPA (j-7) is shown below.

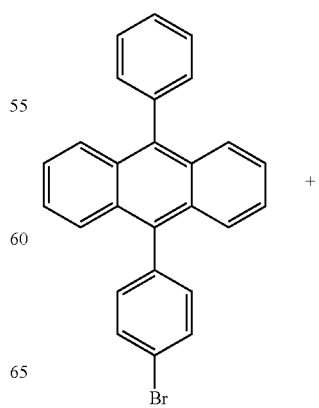

-continued

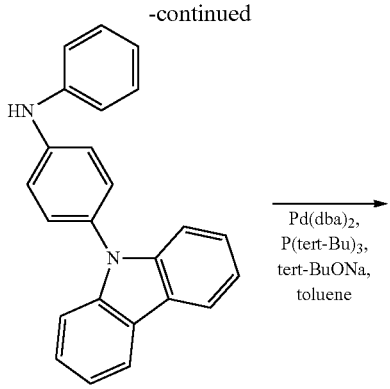

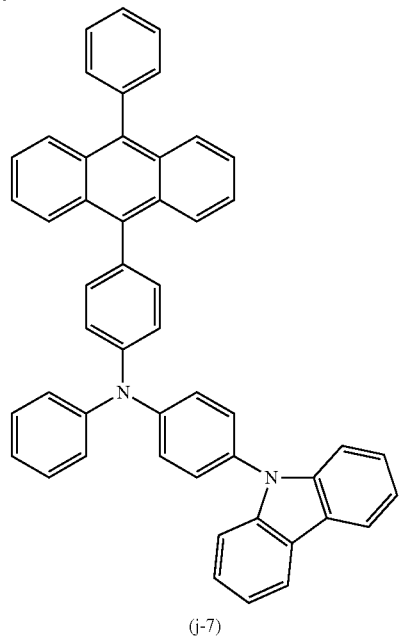

(j-7)

Next, a method of synthesizing CzPA, which is expressed by the Structural Formula 117 below, will be explained.

(117)

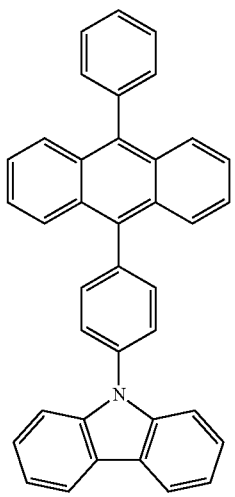

A method of synthesis of CzPA will be explained. A starting material for CzPA is 9-(4-bromophenyl)-10-phenylanthracene, which is obtained in Step 1 of the synthesis of YGAPA. A mixture containing 1.3 g (3.2 mmol) of 9-(4-bromophenyl)-10-phenylanthracene, 578 mg (3.5 mmol) of carbazole, 50 mg (0.017 mmol) of bis(dibenzylideneacetone)palladium(II), 1.0 mg (0.010 mmol) of t-butoxysodium, 0.1 mL of tri(t-butylphosphine), and 30 mL of toluene, was heated under reflux for 10 hours at 110° C. After the reaction, the reaction solution was washed with water. The aqueous layer was extracted with toluene, and combined with the organic layer. The layers were washed with a saturated saline solution, then dried with magnesium sulfate. After natural filtration, the filtrate was concentrated, and an oily product was obtained. The oily product was purified by silica gel column chromatograghy (hexane: toluene=7:3) and recrystallized with dichloromethane and hexane, giving 1.5 g of the target product of CzPA in a yield of 93%. Sublimation purification was conducted for 20 hours on 5.50 g of the CzPA obtained, at 270° C., under an argon air current (current speed 3.0 ml/min), at a pressure of 6.7 Pa. 3.98 g was recovered, in a yield of 72%. This compound was confirmed to be CzPA by a nuclear magnetic resonance method (NMR). $^1$H NMR of the CzPA is as follows: (300 MHz, CDCl$_3$); δ=8.22 (d, J=7.8 Hz, 2H), 7.86-7.82 (m, 3H), 7.61-736 (m, 20H).

A synthesis scheme (k-1) of CzPA obtained from 9-phenyl-10-(4-bromophenyl)anthracene is shown below.

(k-1)

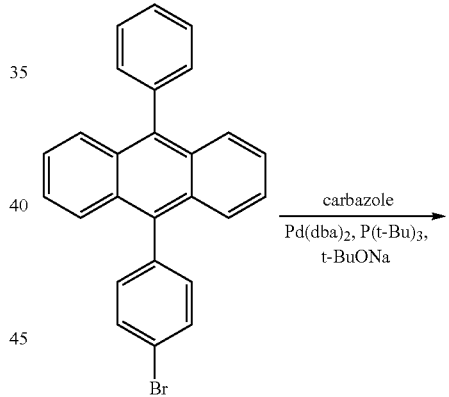

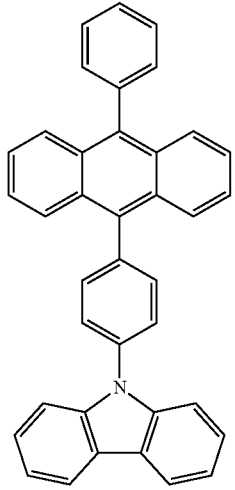

What is claimed is:

1. A semiconductor device comprising:
an element comprising a material having a molecular weight 678,
wherein the material having the molecular weight 678 consists of a first part of a molecular weight 510 and a second part of a molecular weight 168, and
wherein the first part is bonded to the second part by a single bond.

2. The semiconductor device according to claim 1, wherein the element is provided over a glass substrate.

3. The semiconductor device according to claim 1, wherein the element is provided over an insulating film comprising silicon nitride.

4. The semiconductor device according to claim 1, wherein the material having the molecular weight 678 is represented by Structural Formula 27,

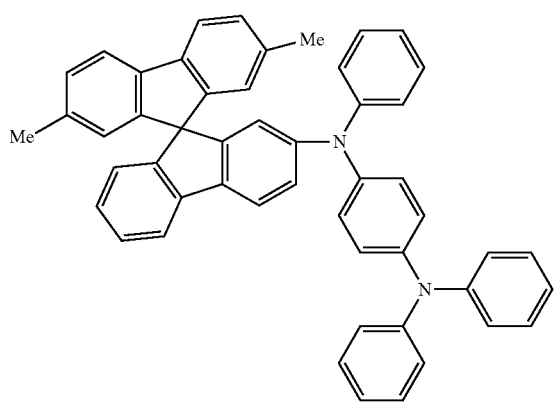

(27)

5. The semiconductor device according to claim 1, wherein the element is a light-emitting element.

6. A semiconductor device comprising:
an element comprising a first electrode, a second electrode over the first electrode, a layer comprising a material between the first electrode and the second electrode,
wherein the material has a molecular weight 678,
wherein the material consists of a first part of a molecular weight 510 and a second part of a molecular weight 168, and
wherein the first part is bonded to the second part by a single bond.

7. The semiconductor device according to claim 6, wherein the element is provided over a glass substrate.

8. The semiconductor device according to claim 6, wherein the element is provided over an insulating film comprising silicon nitride.

9. The semiconductor device according to claim 6, wherein the first electrode is an anode and the second electrode is a cathode.

10. The semiconductor device according to claim 6, wherein the first electrode comprises at least one of ITO and silver.

11. The semiconductor device according to claim 6, wherein the second electrode comprises at least one of magnesium and silver.

12. The semiconductor device according to claim 6, wherein the material is represented by Structural Formula 27,

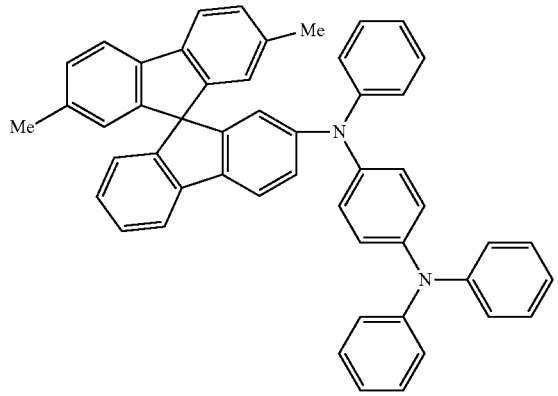

(27)

13. The semiconductor device according to claim 6, wherein the element is a light-emitting element.

14. A semiconductor device comprising:
a transistor over a substrate;
an element electrically connected to the transistor, the element comprising a first electrode, a second electrode over the first electrode, and a layer comprising a material interposed therebetween; and
wherein the material has a molecular weight 678,
wherein the material consists of a first part of a molecular weight 510 and a second part of a molecular weight 168, and
wherein the first part is bonded to the second part by a single bond.

15. The semiconductor device according to claim 14, wherein the substrate is a glass substrate.

16. The semiconductor device according to claim 14, wherein the transistor comprises a crystalline semiconductor film.

17. The semiconductor device according to claim 14, wherein the transistor comprises a gate electrode comprising molybdenum.

18. The semiconductor device according to claim 14, wherein the element is provided over an insulating film comprising silicon nitride.

19. The semiconductor device according to claim 14, wherein the first electrode is an anode and the second electrode is a cathode.

20. The semiconductor device according to claim 14, wherein the first electrode comprises at least one of ITO and silver.

21. The semiconductor device according to claim 14, wherein the second electrode comprises at least one of magnesium and silver.

22. The semiconductor device according to claim 14, wherein the material is represented by Structural Formula 27, (27)

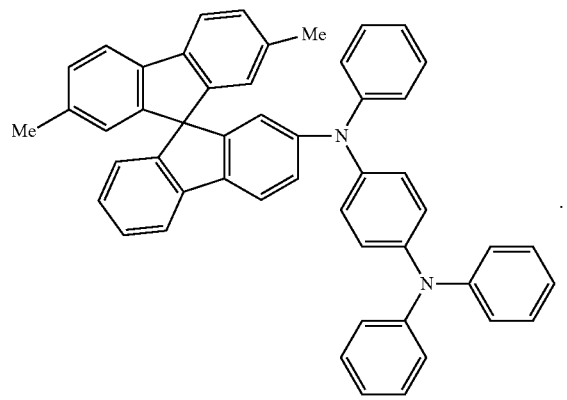

(27)

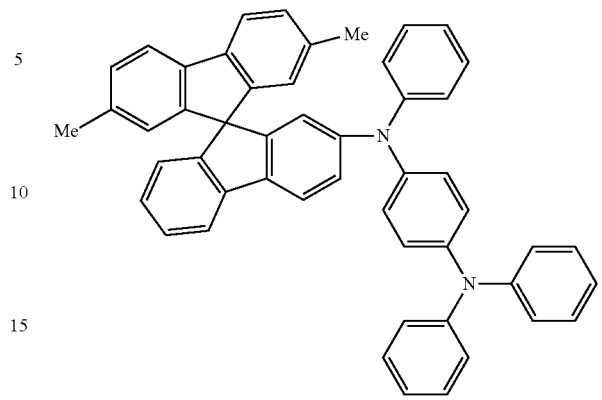

23. The semiconductor device according to claim 14, wherein the element is a light-emitting element.

24. A semiconductor device comprising:

an element comprising a material represent by Structural Formula 27

25. The semiconductor device according claim 24, wherein the element comprises a first electrode, a second electrode over the first electrode, and a layer between the first electrode and the second electrode, and wherein the layer comprises the material.

26. The semiconductor device according claim 24, further comprising:

a transistor;

wherein the transistor is electrically connected to the element, wherein the element comprises a first electrode, a second electrode over the first electrode, and a layer between the first electrode and the second electrode, and wherein the layer comprises the material.

* * * * *